United States Patent
Gray et al.

(10) Patent No.: US 12,181,352 B2
(45) Date of Patent: Dec. 31, 2024

(54) INSOLE XYZ FORCE DETECTION SYSTEM

(71) Applicant: SIGMASENSE, LLC., Wilmington, DE (US)

(72) Inventors: Michael Shawn Gray, Dripping Springs, TX (US); Kevin Joseph Derichs, Buda, TX (US); Richard Stuart Seger, Jr., Belton, TX (US); Timothy W. Markison, Mesa, AZ (US)

(73) Assignee: SIGMASENSE, LLC., Austin, TX (US)

( * ) Notice: Subject to any disclaimer, the term of this patent is extended or adjusted under 35 U.S.C. 154(b) by 417 days.

(21) Appl. No.: 17/575,594

(22) Filed: Jan. 13, 2022

(65) Prior Publication Data

US 2022/0390297 A1 Dec. 8, 2022

Related U.S. Application Data

(60) Provisional application No. 63/202,251, filed on Jun. 3, 2021.

(51) Int. Cl.
*G01L 1/14* (2006.01)
*A43B 3/44* (2022.01)
(Continued)

(52) U.S. Cl.
CPC .............. *G01L 1/146* (2013.01); *A43B 3/44* (2022.01); *A61B 5/1038* (2013.01);
(Continued)

(58) Field of Classification Search
CPC ............ A63B 2220/13; A63B 2220/56; A63B 2220/58; A63B 2220/836; A63B 2220/89;
(Continued)

(56) References Cited

U.S. PATENT DOCUMENTS 3,184,739 A 5/1965 Frederick
3,795,911 A 3/1974 Hammack
(Continued)

FOREIGN PATENT DOCUMENTS

CN 103995626 A 8/2014
CN 104182105 A 12/2014
(Continued)

OTHER PUBLICATIONS

"F-Scan System." Tekscan, Inc. https://www.tekscan.com/products-solutions/systems/f-scan-system. Accessed Aug. 18, 2017.
(Continued)

*Primary Examiner* — Brandi N Hopkins
(74) *Attorney, Agent, or Firm* — GARLICK & MARKISON; Timothy W. Markison

(57) ABSTRACT

A low power force detection system includes variable capacitors, a drive sense module, and a processing module. A drive sense circuit of the drive sense module is operable to provide an analog and frequency domain signal to a variable capacitor. The drive sense circuit is further operable to detect a characteristic of the variable capacitor based on the analog and frequency domain signal and to generate a representative signal of the characteristic. The processing module is operable to generate a digital value based on the representative and to write the digital value to memory.

23 Claims, 41 Drawing Sheets
(26 of 41 Drawing Sheet(s) Filed in Color)

(51) Int. Cl.
*A43B 13/00* (2006.01)
*A61B 5/00* (2006.01)
*A61B 5/103* (2006.01)

(52) U.S. Cl.
CPC .......... *A61B 5/6807* (2013.01); *A61B 5/7225* (2013.01); *A61B 2562/0247* (2013.01); *A61B 2562/046* (2013.01)

(58) Field of Classification Search
CPC ...... A63B 2225/02; G16H 40/67; A43B 3/44; G01L 5/0052; G01L 5/161; G01L 5/164; G01L 5/165; G01L 5/167; G01L 1/146; A61B 5/1038; A61B 5/6807; A61B 5/7225; A61B 2562/0247; A61B 2562/046
See application file for complete search history.

(56) References Cited

U.S. PATENT DOCUMENTS

| | | |
|---|---|---|
| 3,953,856 A | 4/1976 | Hammack |
| 4,992,797 A | 2/1991 | Gjessing |
| 5,247,307 A | 9/1993 | Gandar |
| 5,410,314 A | 4/1995 | Frush |
| 5,437,178 A | 8/1995 | Esin et al. |
| 5,925,001 A | 7/1999 | Hoyt |
| 6,218,972 B1 | 4/2001 | Groshong |
| 6,222,481 B1 | 4/2001 | Abrahamson |
| 6,665,013 B1 | 12/2003 | Fossum et al. |
| 7,394,046 B2 | 7/2008 | Olsson |
| 7,476,233 B1 | 1/2009 | Wiener et al. |
| 7,528,755 B2 | 5/2009 | Hammerschmidt |
| 7,648,441 B2 | 1/2010 | Silk |
| 7,717,962 B2 | 5/2010 | Wilson |
| 7,911,339 B2 | 3/2011 | Vock |
| 8,011,229 B2 | 9/2011 | Lieberman |
| 8,031,094 B2 | 10/2011 | Hotelling |
| 8,089,289 B1 | 1/2012 | Kremin et al. |
| 8,113,843 B2 | 2/2012 | Naya |
| 8,279,180 B2 | 10/2012 | Hotelling et al. |
| 8,280,681 B2 | 10/2012 | Vock |
| 8,375,784 B2 | 2/2013 | Bamberg |
| 8,384,551 B2 | 2/2013 | Ross |
| 8,467,979 B2 | 6/2013 | Sobolewski |
| 8,537,110 B2 | 9/2013 | Kruglick |
| 8,547,114 B2 | 10/2013 | Kremin |
| 8,587,535 B2 | 11/2013 | Oda et al. |
| 8,625,726 B2 | 1/2014 | Kuan |
| 8,657,681 B2 | 2/2014 | Kim |
| 8,686,862 B2 | 4/2014 | Dunham |
| 8,692,675 B2 | 4/2014 | Agrawal |
| 8,784,115 B1 | 7/2014 | Chuang |
| 8,821,417 B2 | 9/2014 | McGregor |
| 8,870,795 B2 | 10/2014 | Kim |
| 8,966,400 B2 | 2/2015 | Yeap |
| 8,968,218 B2 | 3/2015 | Wukasch |
| 8,982,097 B1 | 3/2015 | Kuzo et al. |
| 9,081,437 B2 | 7/2015 | Oda |
| 9,201,547 B2 | 12/2015 | Elias |
| 9,256,281 B2 | 2/2016 | Ur |
| 9,349,301 B2 | 5/2016 | Ur |
| 9,352,207 B2 | 5/2016 | Balakrishnan |
| 9,393,697 B1 | 7/2016 | Beardsley |
| 9,756,895 B2 | 9/2017 | Rice |
| 9,763,489 B2 | 9/2017 | Amos |
| 9,810,591 B2 | 11/2017 | Walker |
| 9,810,709 B2 | 11/2017 | Balakrishnan |
| 9,962,111 B2 | 5/2018 | Balakrishnan |
| 10,007,335 B2 | 6/2018 | Lee |
| 10,070,682 B2 | 9/2018 | Rubin |
| 10,307,081 B2 | 6/2019 | Nino |
| 2003/0052657 A1 | 3/2003 | Koernle et al. |
| 2004/0138575 A1 | 7/2004 | Ueyama |
| 2005/0049816 A1 | 3/2005 | Oda |
| 2005/0235758 A1 | 10/2005 | Kowal et al. |
| 2007/0068244 A1 | 3/2007 | Billing |
| 2007/0112285 A1 | 5/2007 | Dar |
| 2007/0142955 A1 | 6/2007 | Lin |
| 2007/0173903 A1 | 7/2007 | Goren |
| 2007/0246334 A1 | 10/2007 | Elkins |
| 2007/0247306 A1 | 10/2007 | Case |
| 2008/0082025 A1 | 4/2008 | Hughes |
| 2008/0108913 A1 | 5/2008 | Lengsfeld |
| 2008/0243265 A1 | 10/2008 | Lanier |
| 2008/0285805 A1 | 11/2008 | Luinge |
| 2008/0287832 A1 | 11/2008 | Collins |
| 2009/0069898 A1 | 3/2009 | Wilson |
| 2009/0235739 A1 | 9/2009 | Morris Bamberg |
| 2009/0240171 A1 | 9/2009 | Morris Bamberg |
| 2010/0041959 A1 | 2/2010 | Iwata |
| 2011/0054359 A1 | 3/2011 | Sazonov |
| 2011/0063154 A1 | 3/2011 | Hotelling et al. |
| 2011/0087445 A1 | 4/2011 | Sobolewski |
| 2011/0119027 A1 | 5/2011 | Zhu |
| 2011/0131838 A1 | 6/2011 | Pas |
| 2011/0152695 A1 | 6/2011 | Granqvist |
| 2011/0251520 A1 | 10/2011 | Shieh |
| 2011/0267219 A1 | 11/2011 | Kisliansky |
| 2011/0298745 A1 | 12/2011 | Souchkov |
| 2011/0304497 A1 | 12/2011 | Molyneux |
| 2012/0059235 A1 | 3/2012 | Davies |
| 2012/0092169 A1 | 4/2012 | Kaiser |
| 2012/0095356 A1 | 4/2012 | Oleson |
| 2012/0234111 A1 | 9/2012 | Molyneux |
| 2012/0253234 A1 | 10/2012 | Yang |
| 2012/0278031 A1 | 11/2012 | Oda |
| 2012/0291563 A1 | 11/2012 | Schrock |
| 2013/0041617 A1 | 2/2013 | Pease |
| 2013/0110011 A1 | 5/2013 | McGregor |
| 2013/0190903 A1 | 7/2013 | Balakrishnan |
| 2013/0278447 A1 | 10/2013 | Kremin |
| 2014/0024972 A1 | 1/2014 | Greene |
| 2014/0174205 A1 | 6/2014 | Clarke |
| 2014/0222173 A1 | 8/2014 | Giedowyn |
| 2014/0327644 A1 | 11/2014 | Mohindra |
| 2015/0091847 A1 | 4/2015 | Chang |
| 2015/0133754 A1 | 5/2015 | Freeman |
| 2015/0157272 A1 | 6/2015 | Balakrishnan |
| 2015/0289820 A1 | 10/2015 | Miller |
| 2015/0313308 A1 | 11/2015 | Rice |
| 2015/0346889 A1 | 12/2015 | Chen |
| 2016/0058326 A1 | 3/2016 | Winfree |
| 2016/0143562 A1 | 5/2016 | Ashby |
| 2016/0174899 A1 | 6/2016 | Besnard |
| 2016/0188049 A1 | 6/2016 | Yang et al. |
| 2016/0287937 A1 | 10/2016 | Fitzgerald |
| 2016/0324445 A1 | 11/2016 | kim |
| 2016/0338411 A1 | 11/2016 | Liu |
| 2016/0037534 A1 | 12/2016 | Czaja |
| 2016/0345664 A1 | 12/2016 | Kohatsu |
| 2016/0351771 A1 | 12/2016 | Schneider |
| 2016/0370854 A1 | 12/2016 | Steele |
| 2016/0375346 A1 | 12/2016 | Czaja |
| 2017/0164684 A1 | 6/2017 | Vock |
| 2017/0225033 A1 | 8/2017 | Czaja |
| 2017/0265560 A1 | 9/2017 | Beers |
| 2018/0049670 A1 | 2/2018 | Markison |
| 2018/0049671 A1 | 2/2018 | Markison |
| 2018/0049703 A1 | 2/2018 | Markison |
| 2018/0157354 A1 | 6/2018 | Blondin et al. |
| 2018/0256071 A1 | 9/2018 | Mathieu |
| 2018/0275824 A1 | 9/2018 | Li |
| 2020/0158770 A1* | 5/2020 | Huynh .................. G01R 29/26 |

(56) References Cited

U.S. PATENT DOCUMENTS

2020/0375496 A1* 12/2020 Nino ............... A63F 13/50
2022/0151332 A1* 5/2022 Gray ............... A61B 5/7225

FOREIGN PATENT DOCUMENTS

| CN | 104536627 A | 4/2015 |
|----|-------------|--------|
| CN | 107771273 A | 3/2018 |
| EP | 2284637 A1  | 2/2011 |

OTHER PUBLICATIONS

Munk-Stander, Jacob. "Evaluation of Piezoelectric Film Sensors for In-Shoe Pressure Measurement." Technical Report No. 06/04. Dept. of Computer Science, University of Copenhagen, Denmark. Feburary 16, 2006. 21 pages.
Rampp, A., Barth, J., Schulein, S., Gar . . . mann, K. G., Klucken, J., & Eskofier, B. M. (2014). Inertial sensor-based stride parameter calculation from gait sequences in geriatric patients. IEEE transactions on biomedical engineering, 62(4), 1089-1097. (Year: 2014).
Willson, J. D., & Kemozek, T. W. (1999). Plantar loading and cadence alterations with fatigue. Medicine and science in sports and exercise, 31(12), 1828-1833. (Year: 1999).
European Patent Office; Extended European Search Report; Application No. 19853507.2; Jun. 13, 2023; 7 pgs.
Baker; How delta-sigma ADCs work, Part 1; Analog Applications Journal; Oct. 1, 2011; 6 pgs.
Brian Pisani, "Digital Filter Types in Delta-Sigma ADCs", Application Report SBAA230, May 2017, pp. 1-8, Texas Instruments Incorporated, Dallas, Texas.

* cited by examiner medial side view cross-section
medial side view

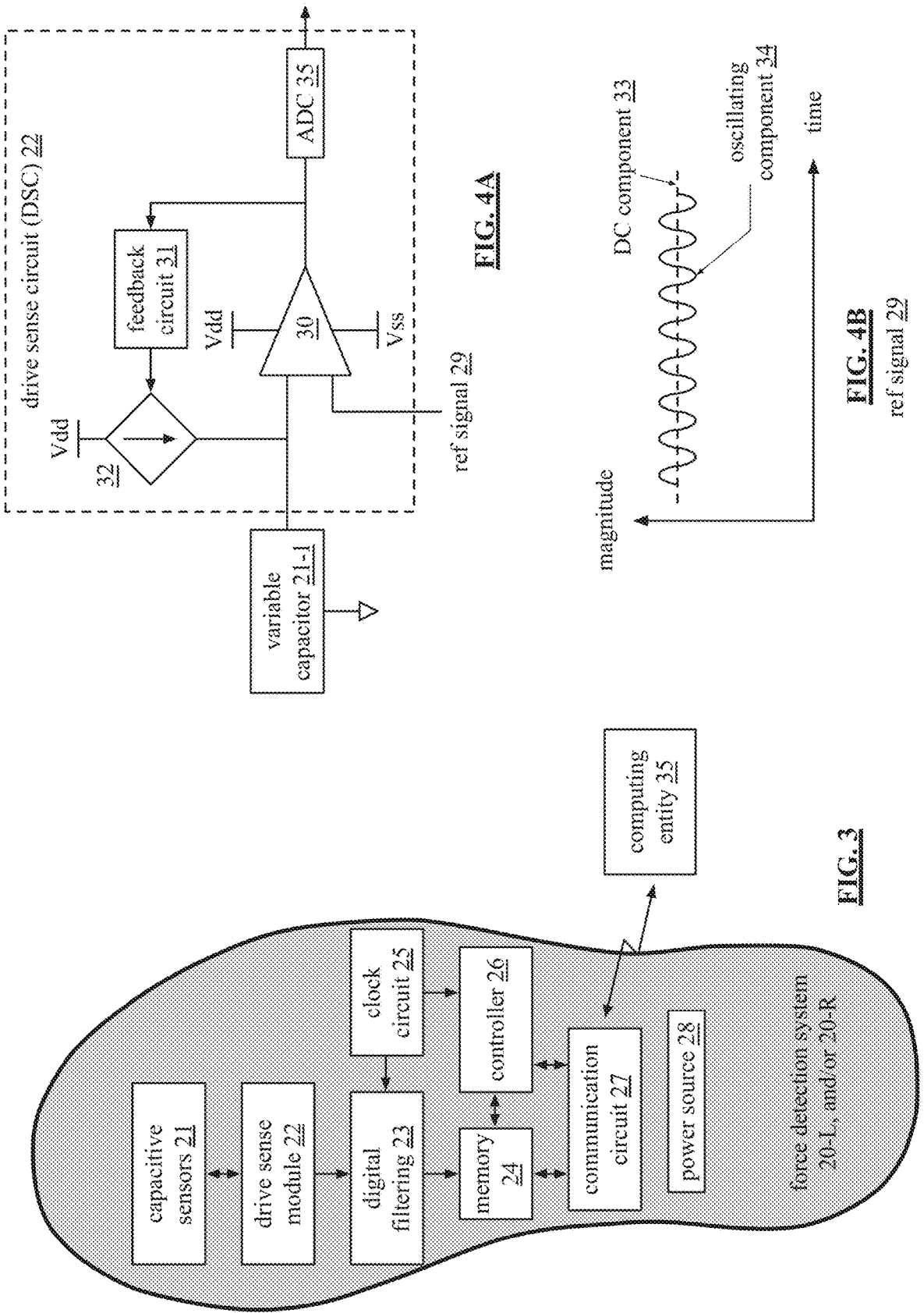

computing device 40 computing device 40 computing device 40 computing device 40

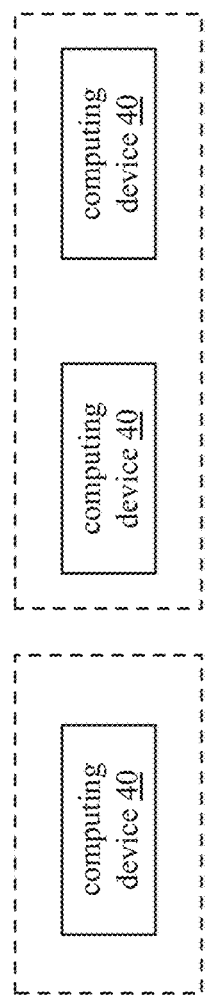
FIG. 5E
computing entity 35
FIG. 5F
computing entity 35
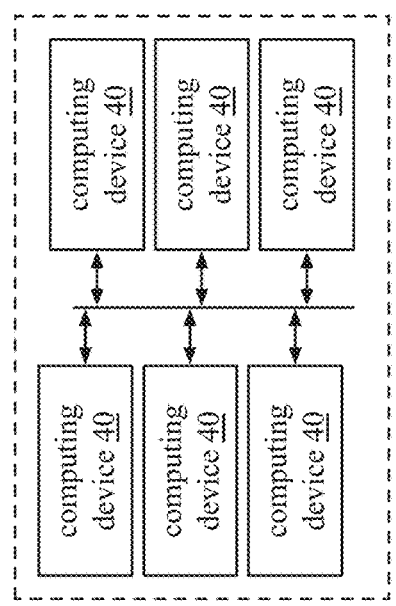
FIG. 5G
computing entity 35
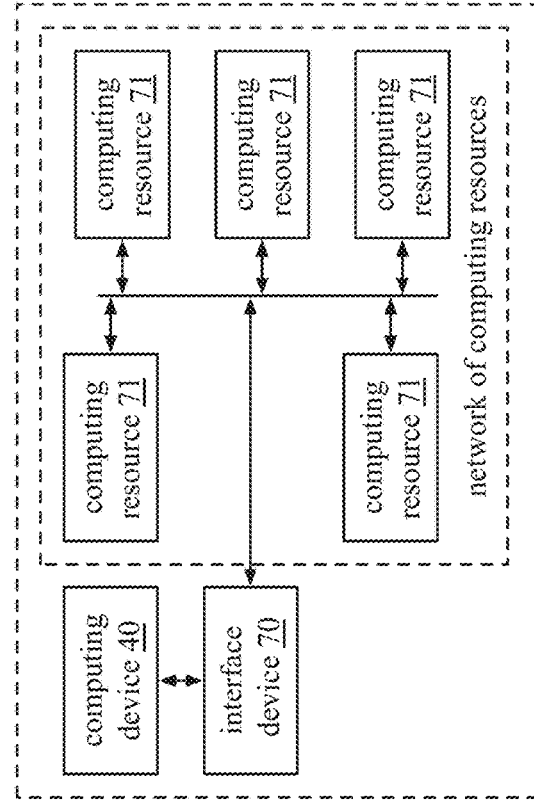
FIG. 5I
computing entity 35
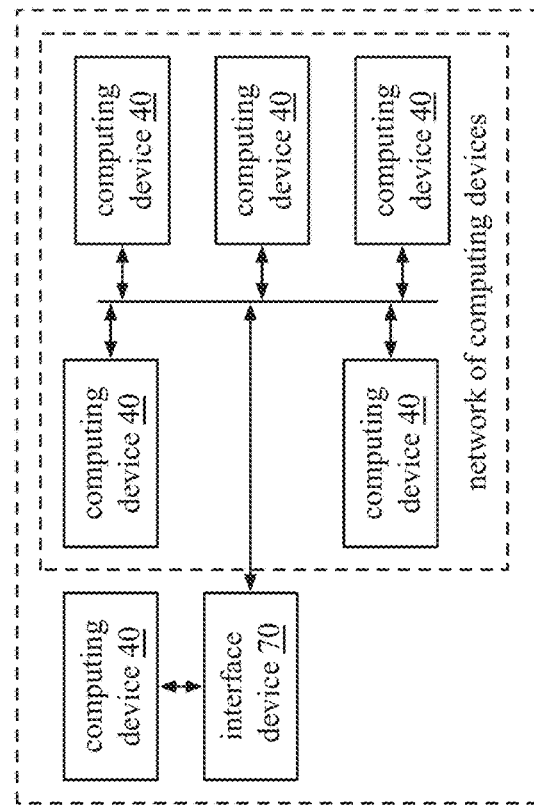
FIG. 5H
computing entity 35

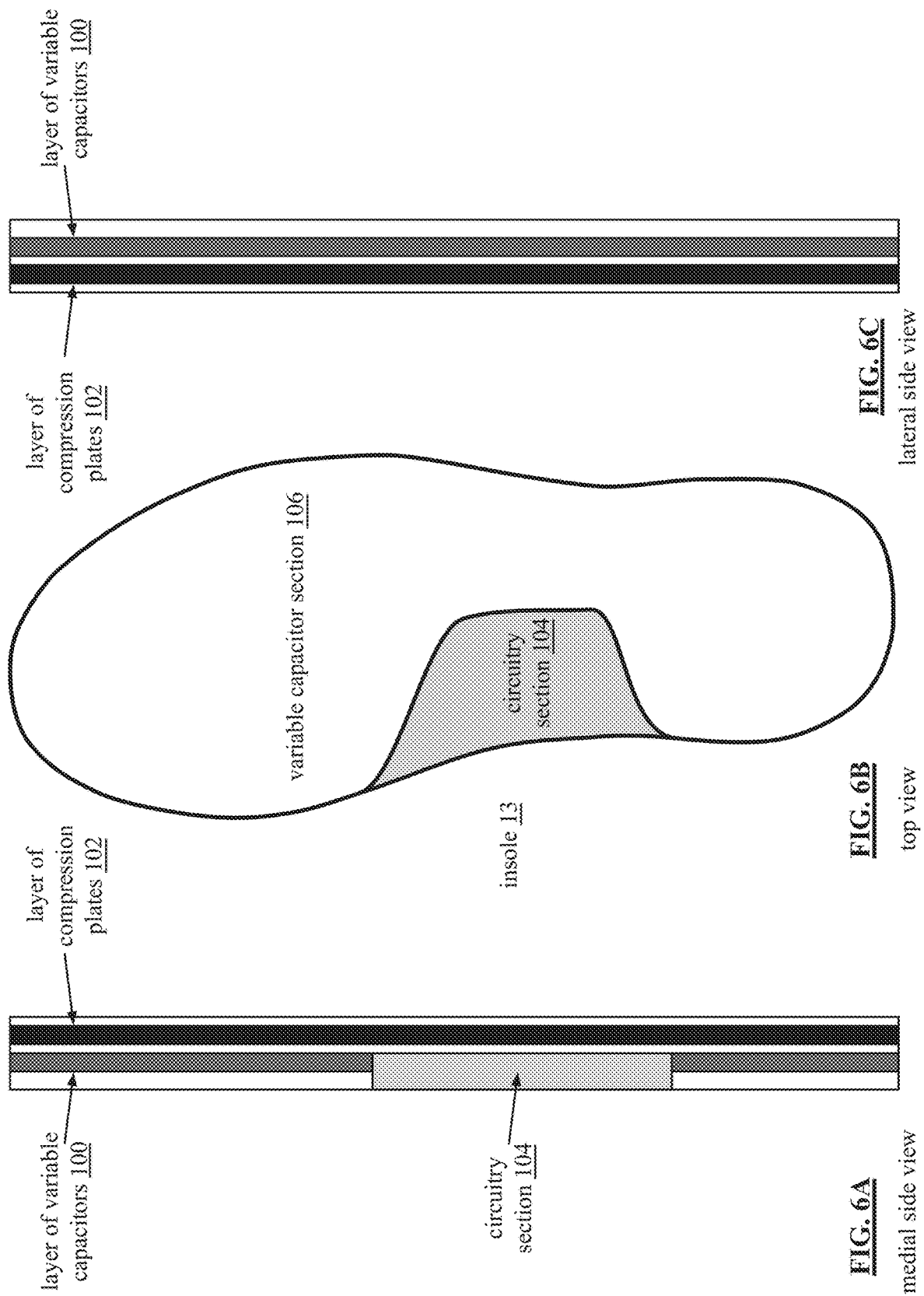

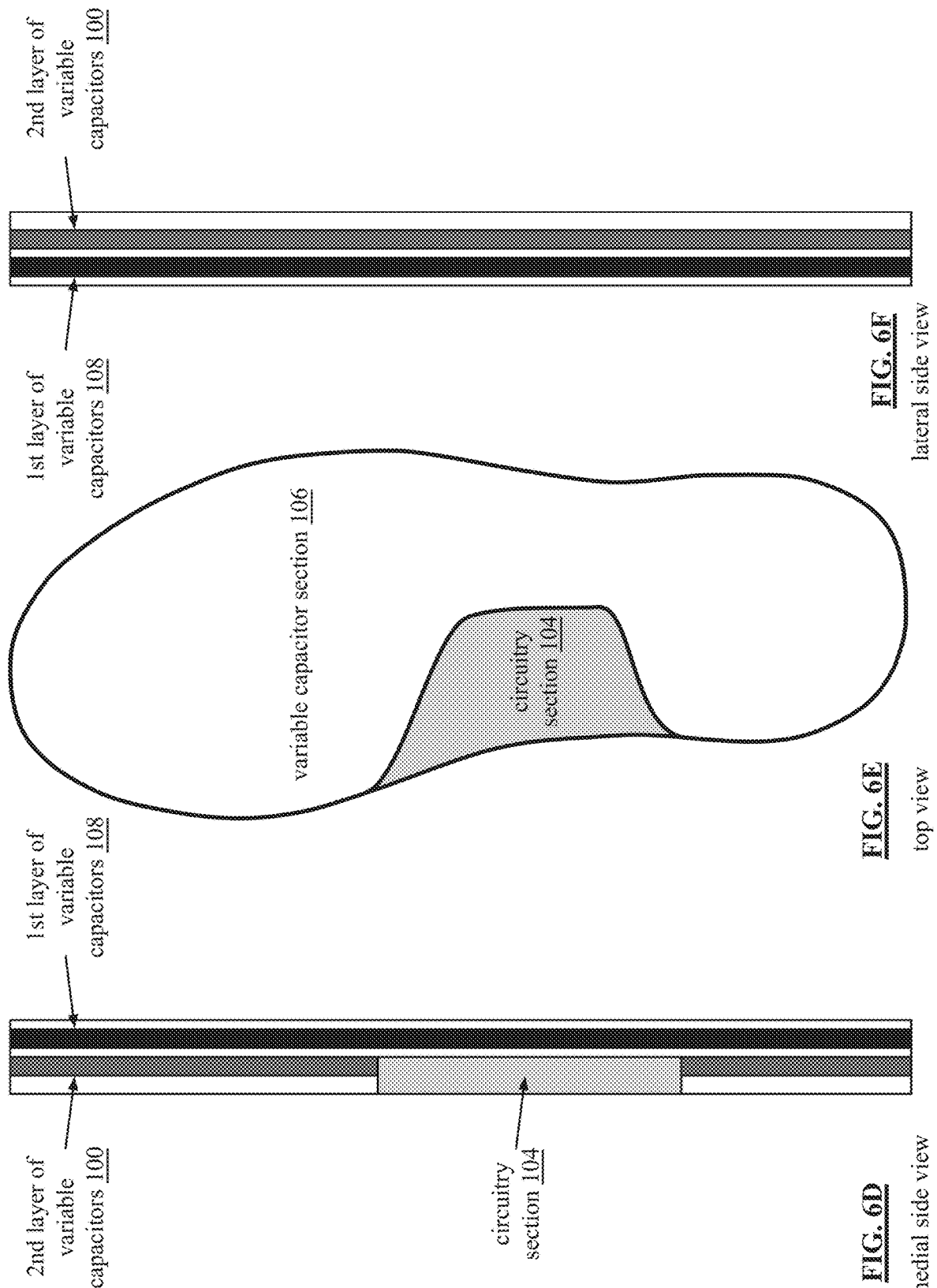

lateral side view top view medial side view

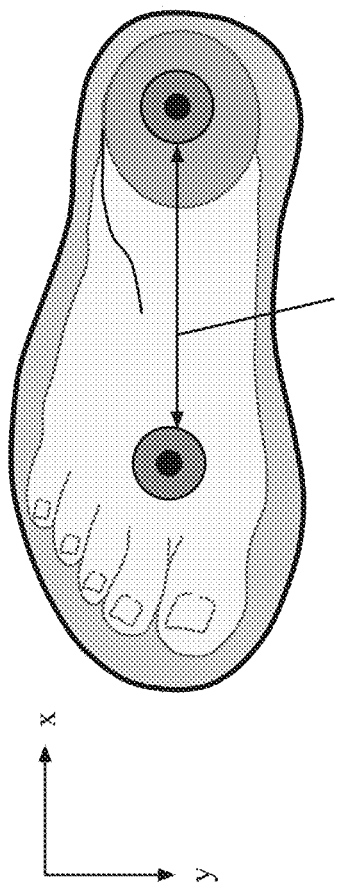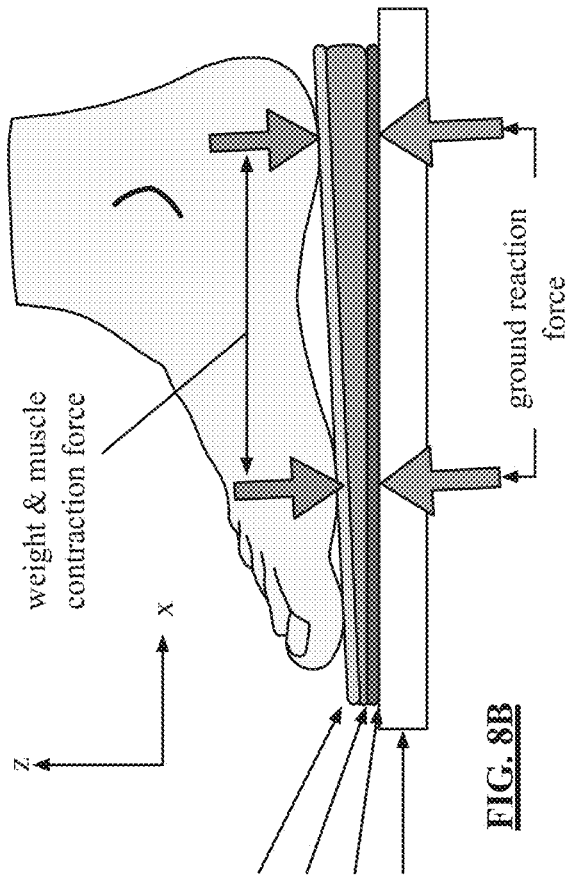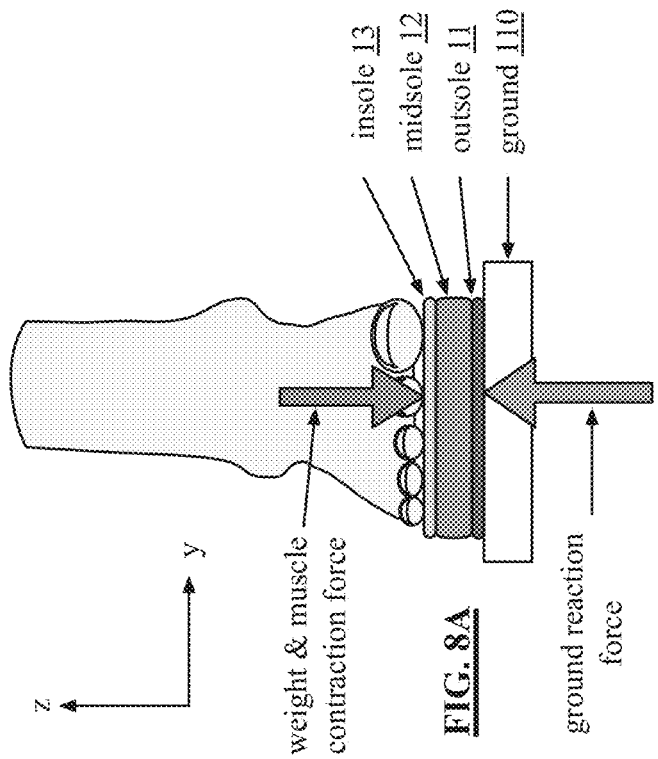
FIG. 8C
FIG. 8B
FIG. 8A

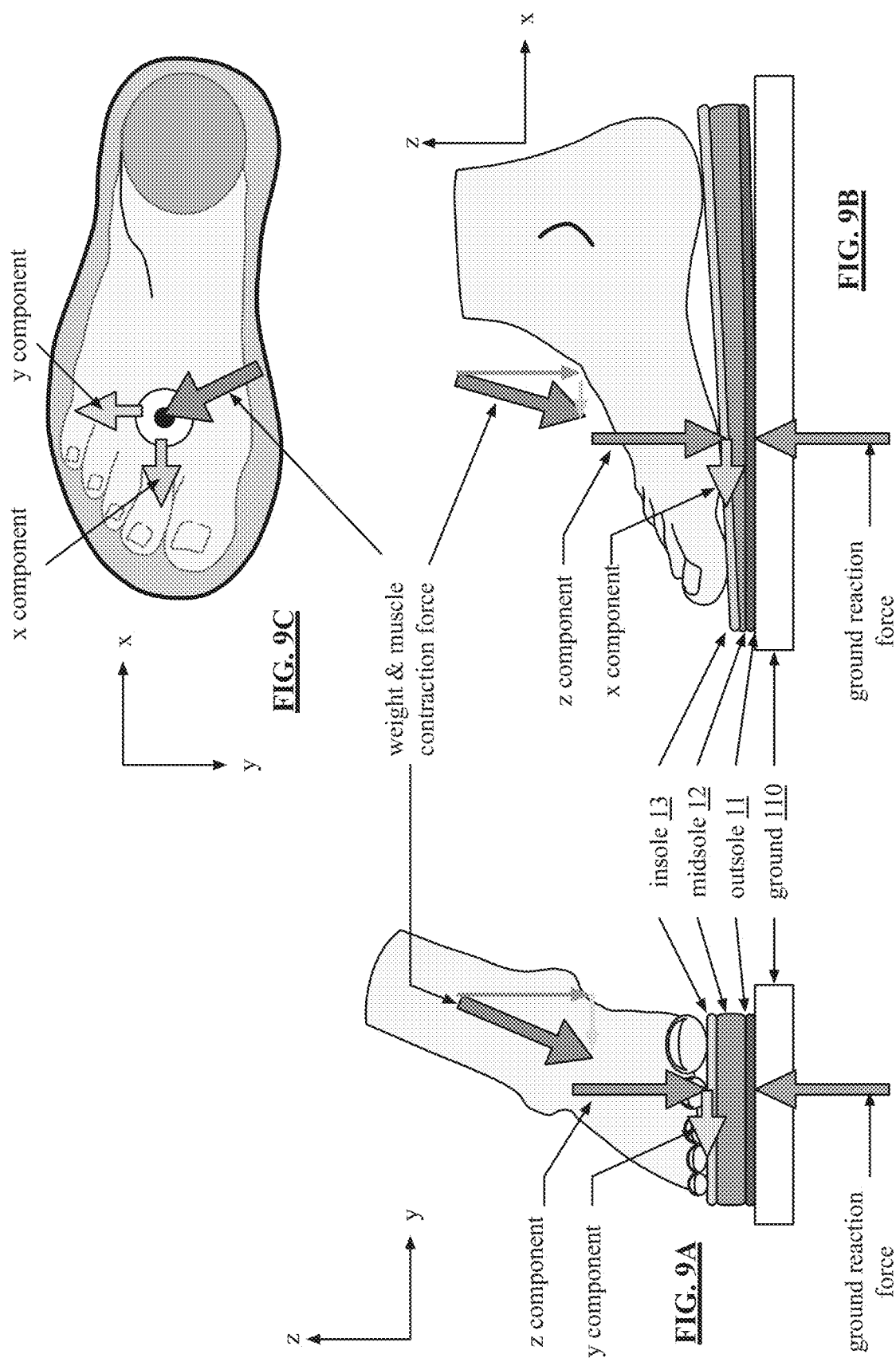

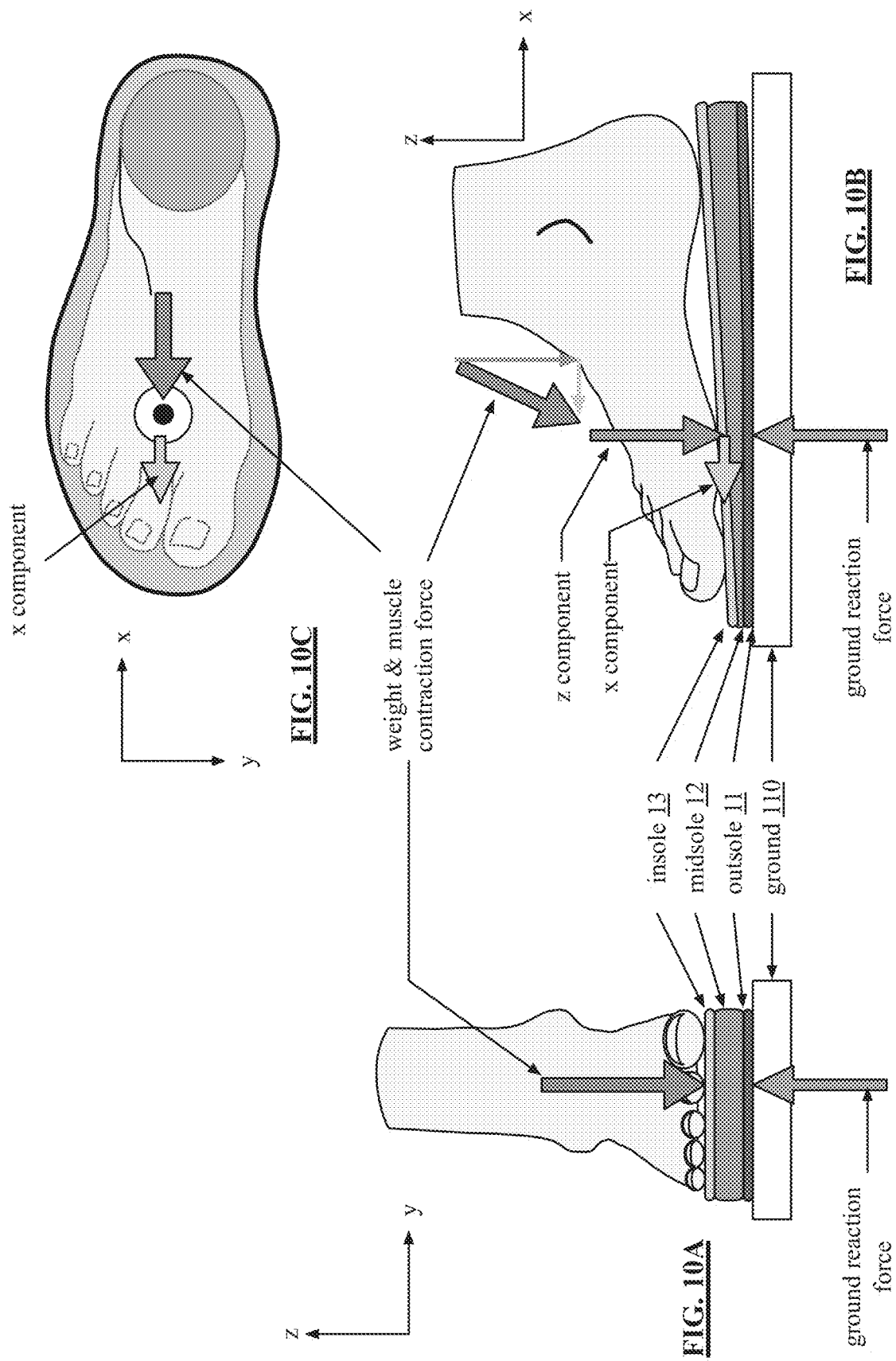

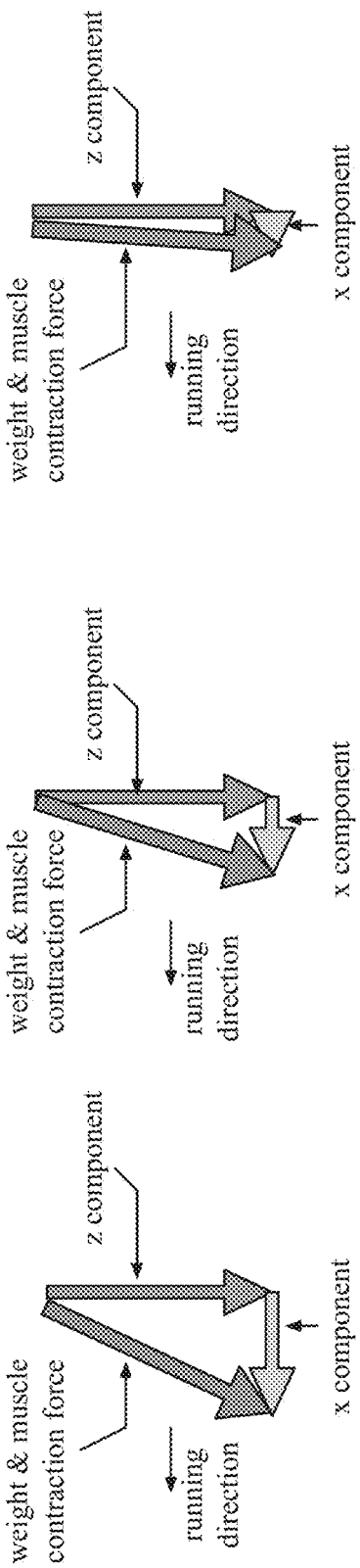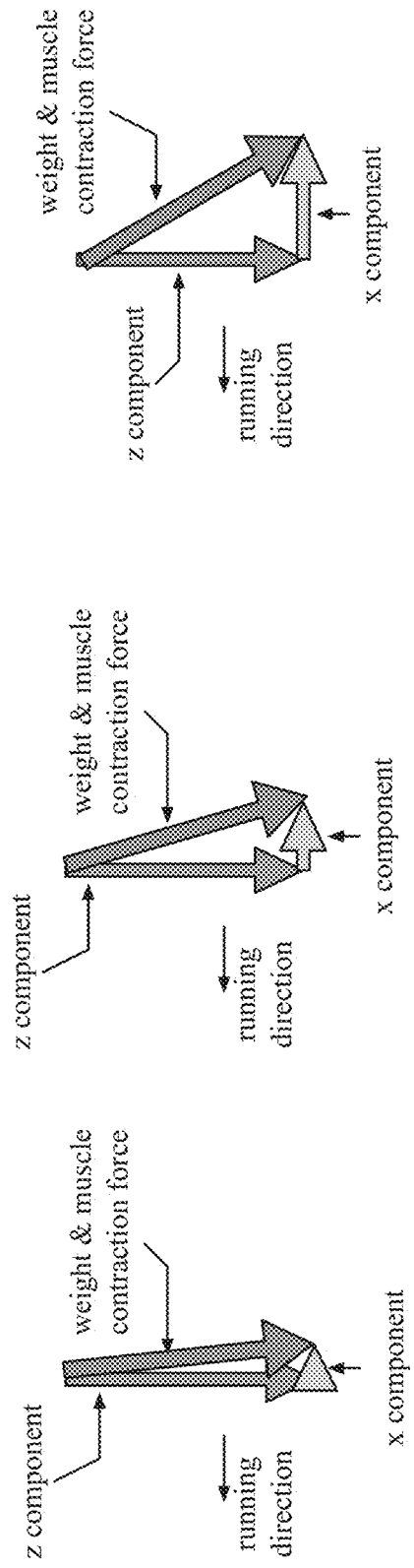

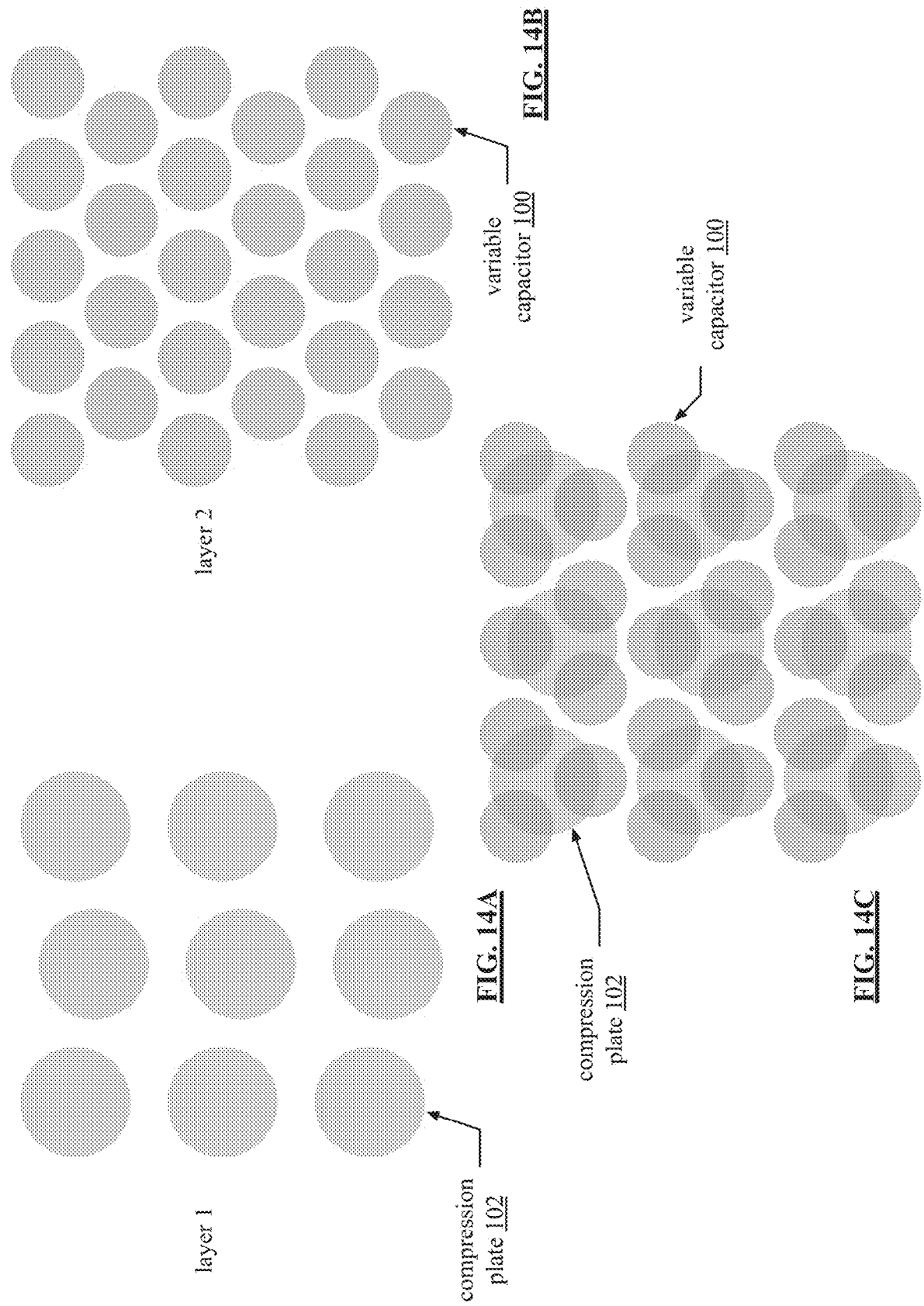

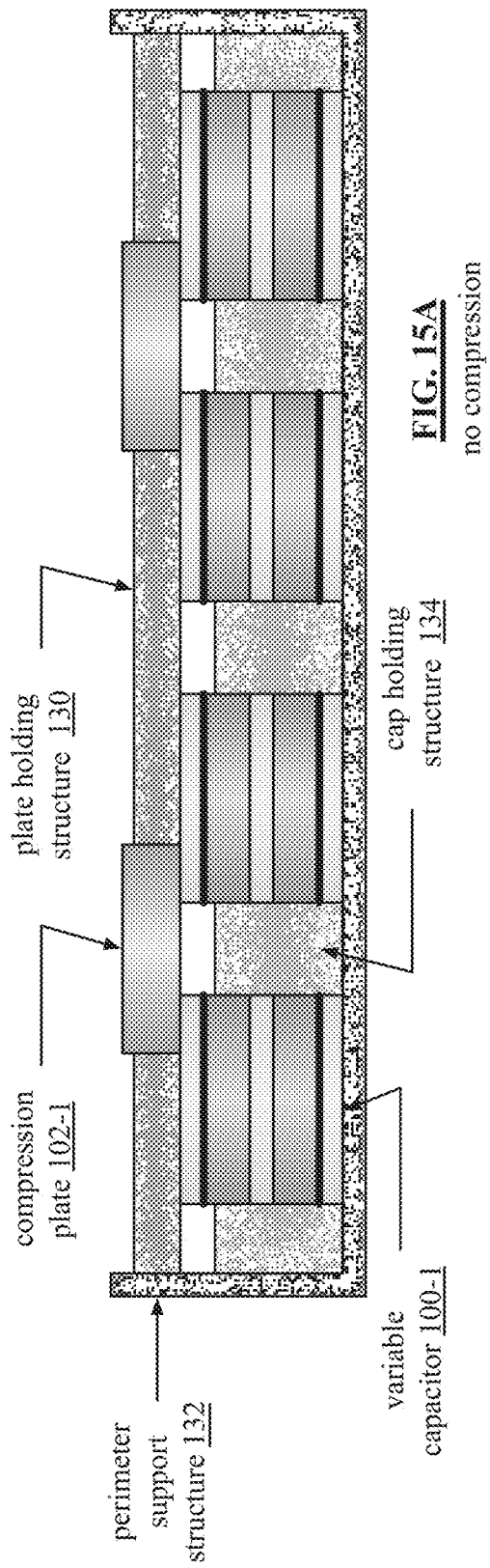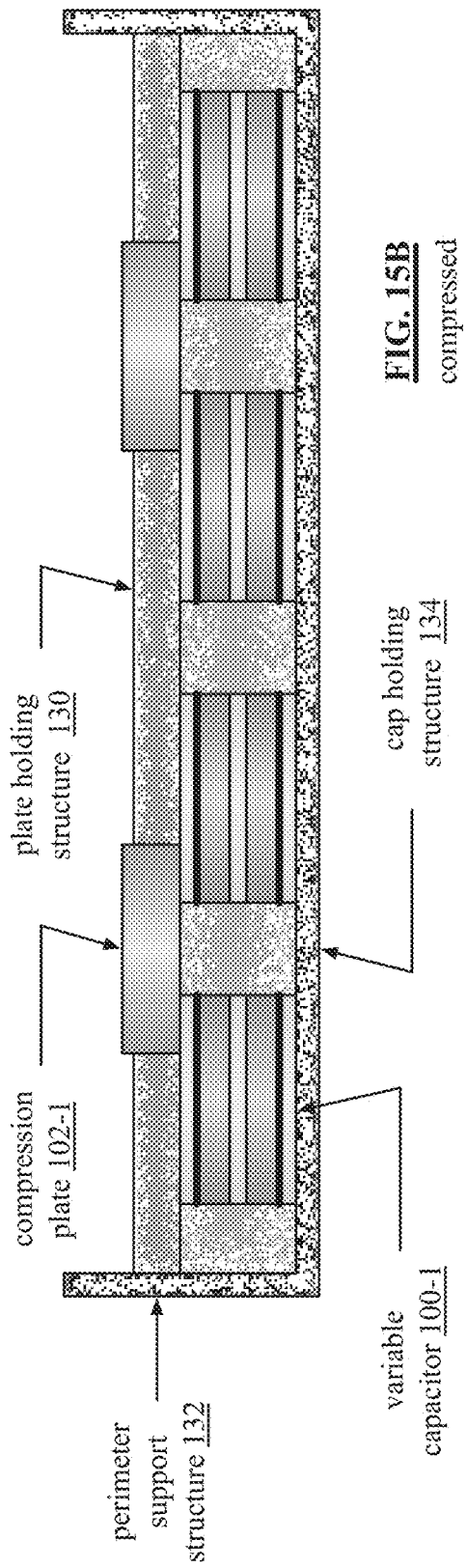

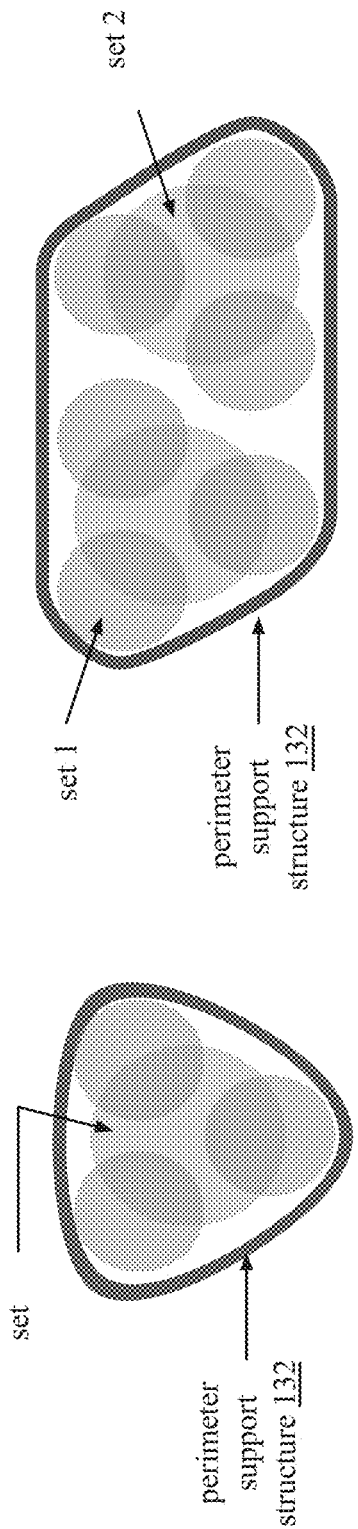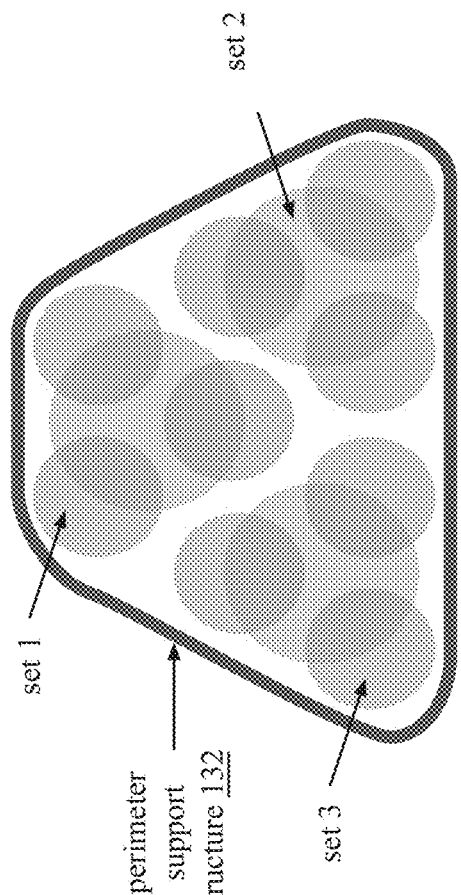

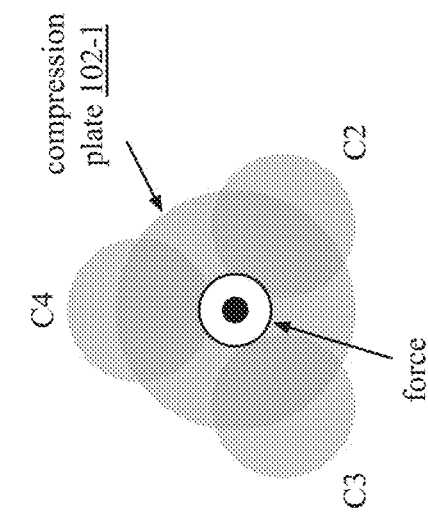
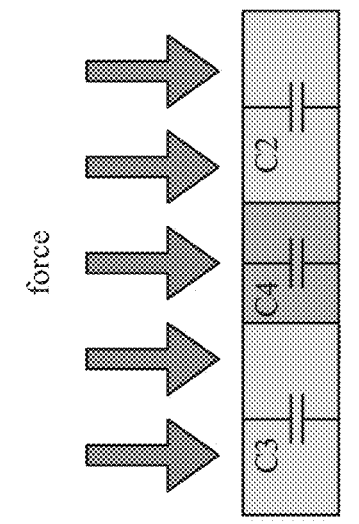
FIG. 17
FIG. 18A
top view
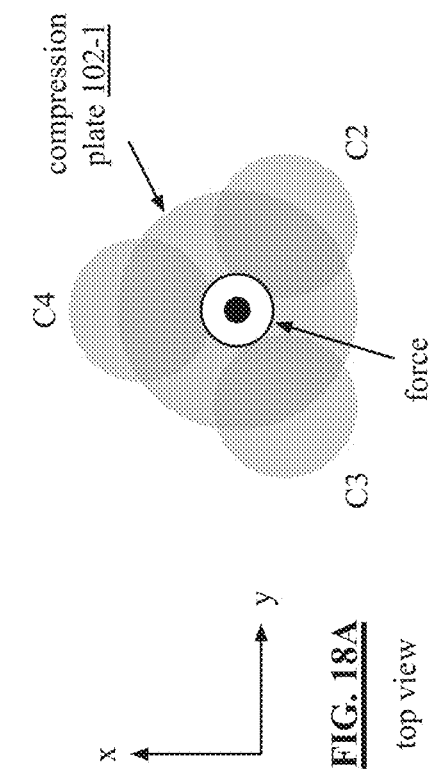
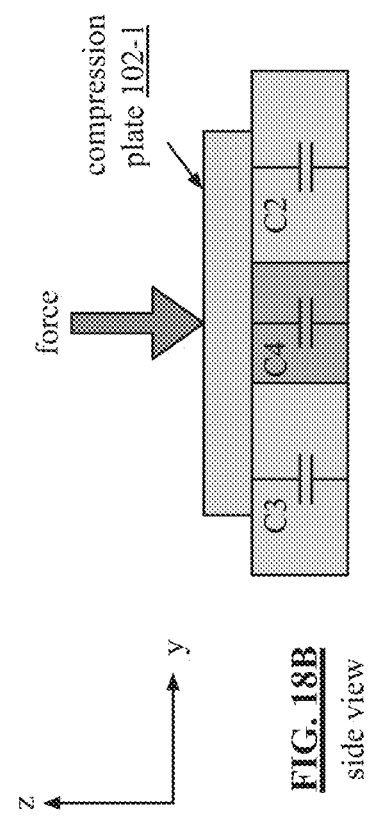
FIG. 18B
side view
FIG. 18C
side view

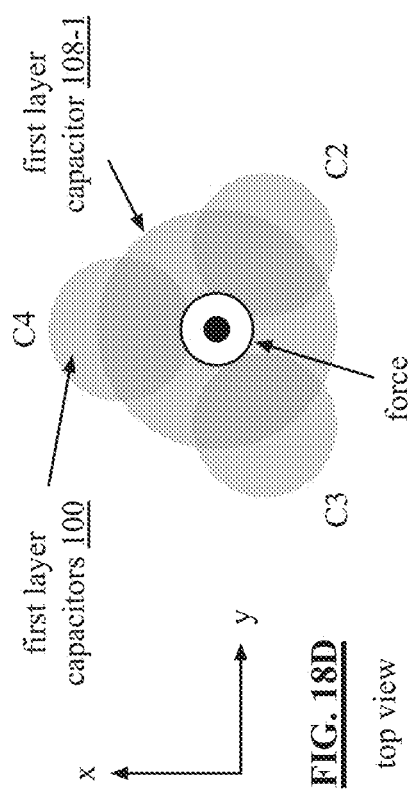
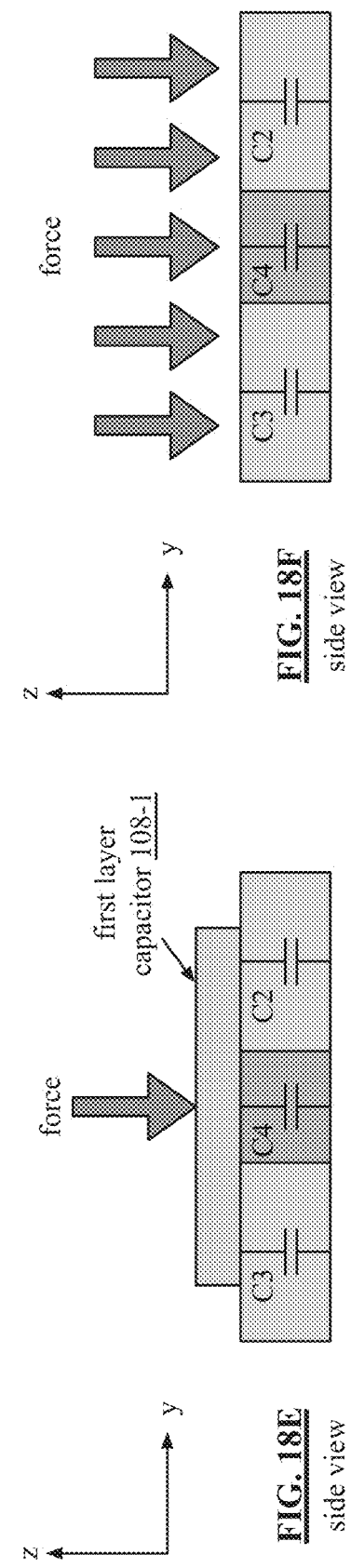
FIG. 18D
top view
FIG. 18E
side view
FIG. 18F
side view

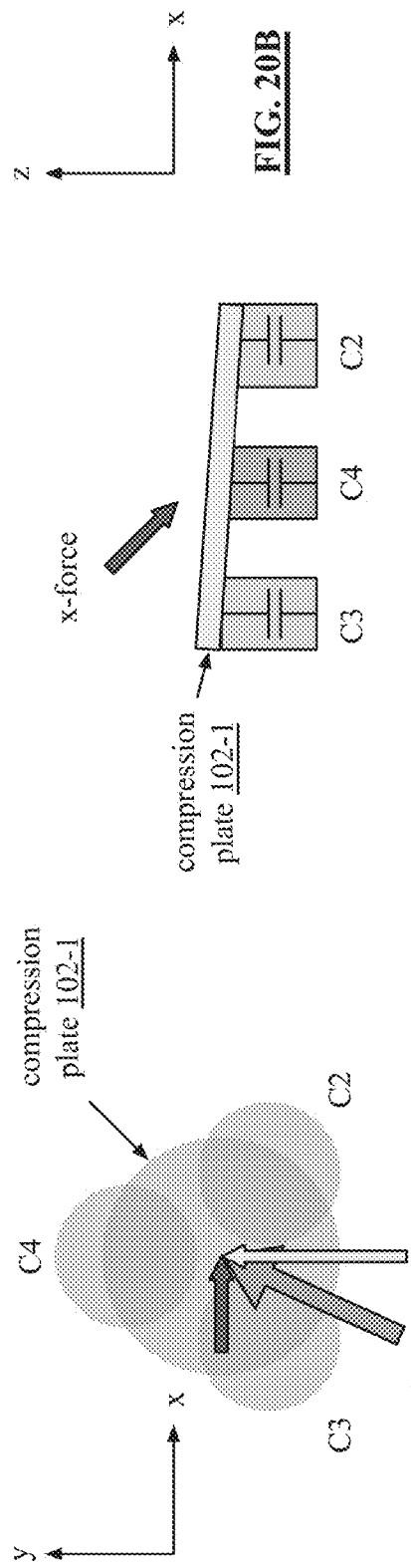
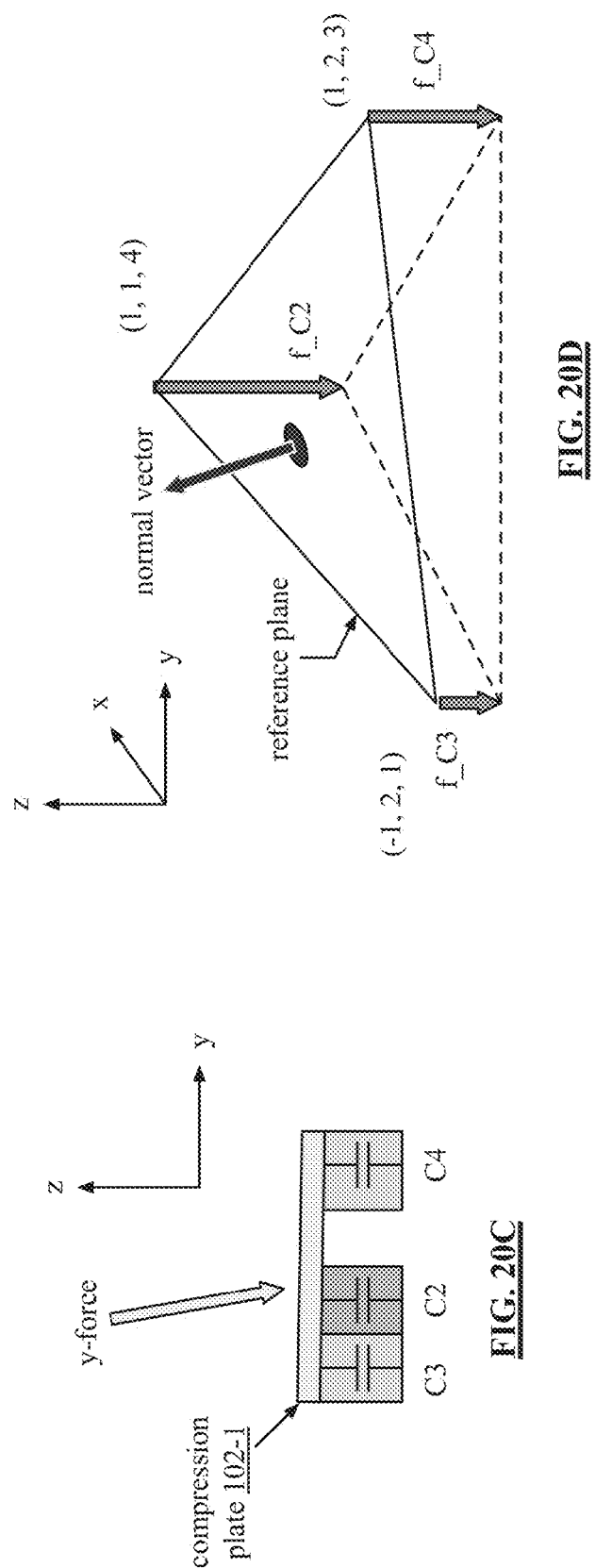
FIG. 20A
FIG. 20B
FIG. 20C
FIG. 20D

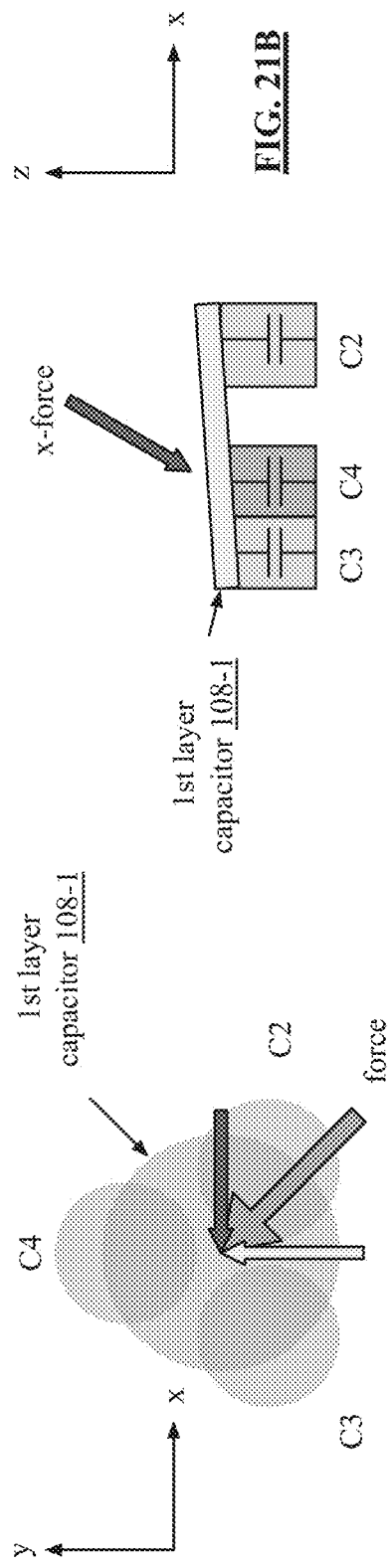
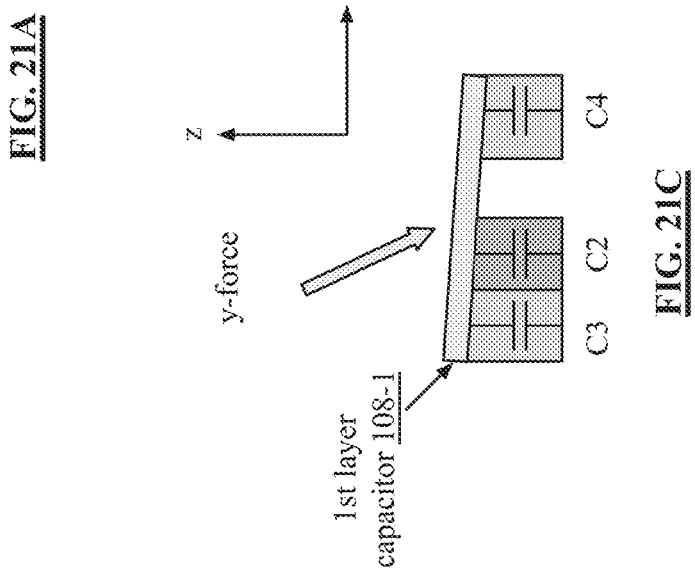
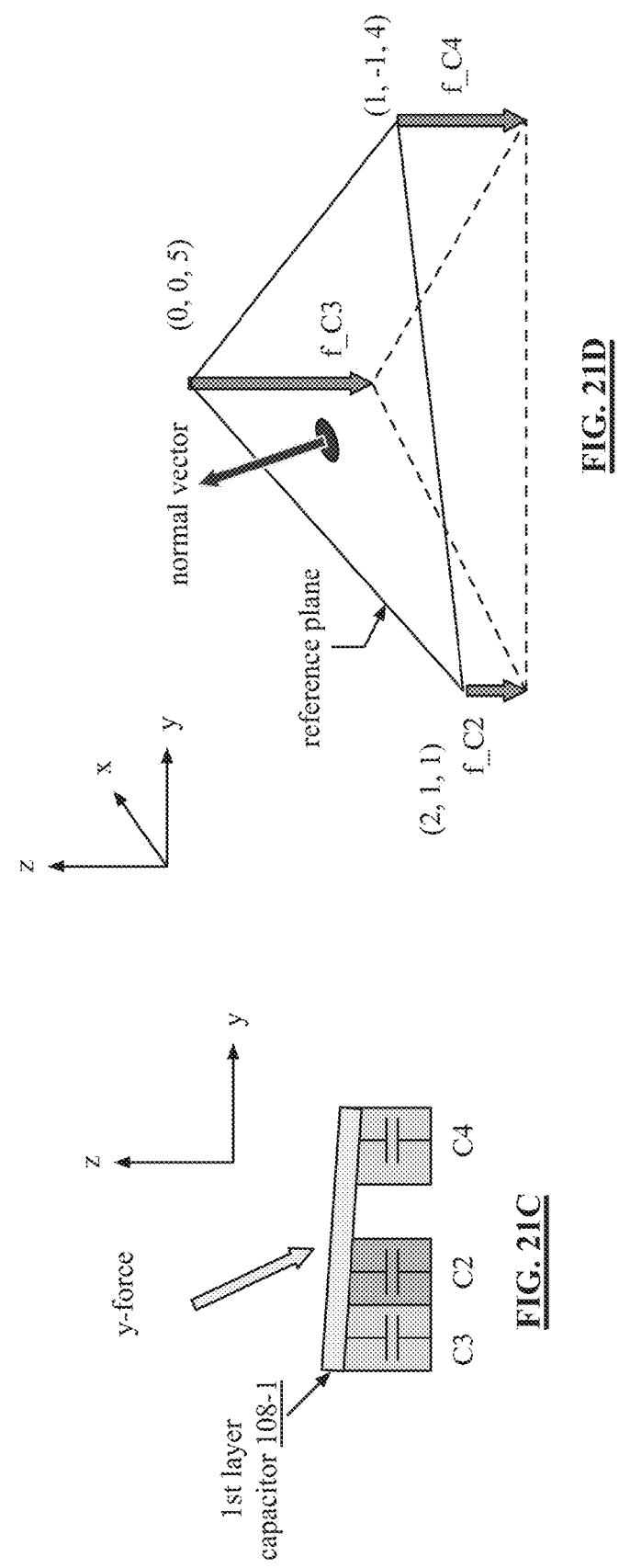
FIG. 21A
FIG. 21B
FIG. 21C
FIG. 21D

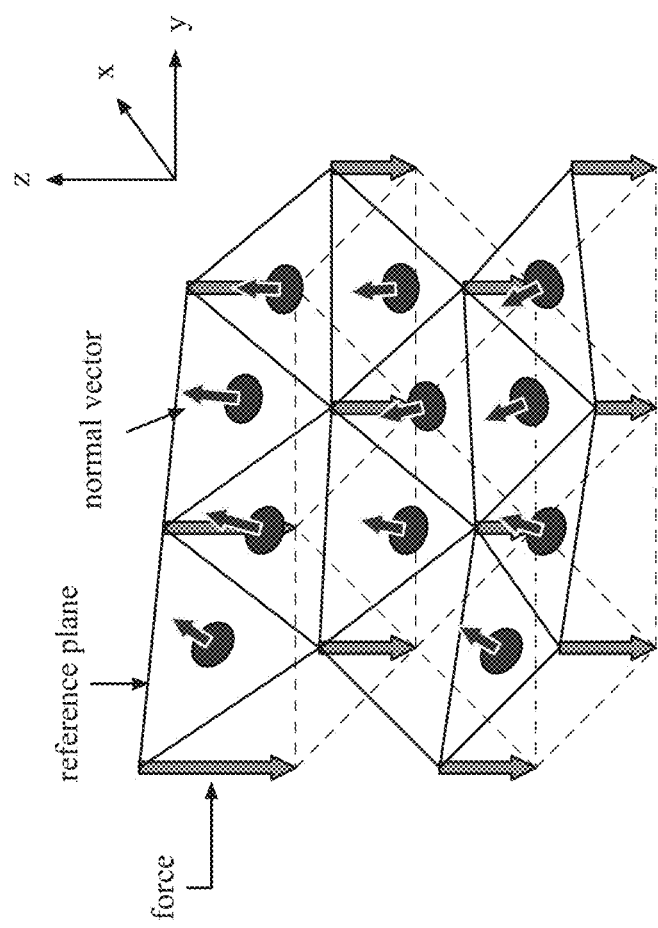
FIG. 22B
force pattern
FIG. 22C
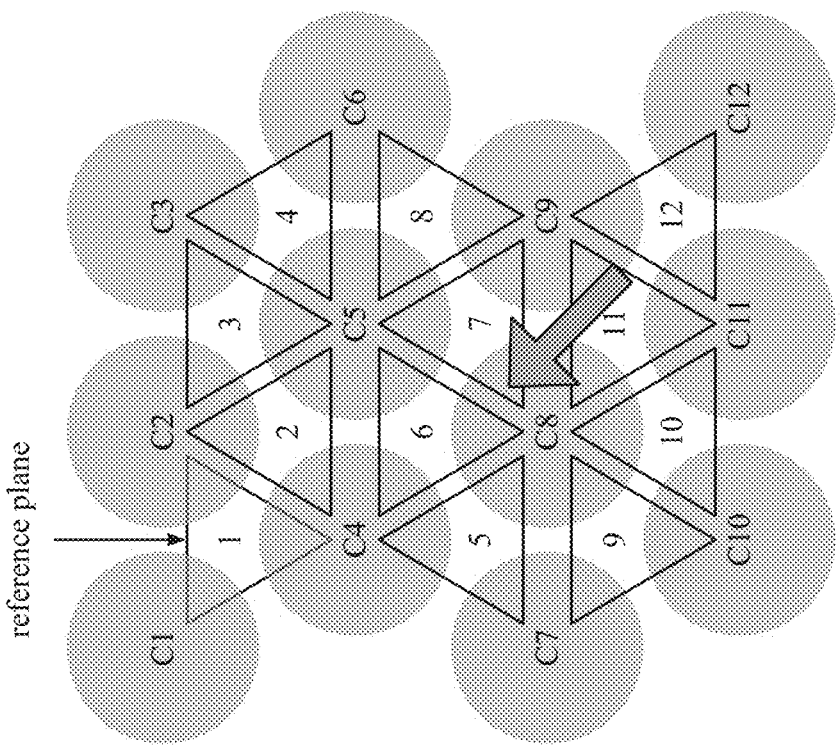
FIG. 22A red = TC2 cell  green = TC6 cell
blue = TC3 cell  black = TC7 cell

| row-column | capacitors | r-c score |
|---|---|---|
| 1-3 | C5, C7 | 16 |
| 1-4 | C5, C6 | 8 |
| 1-5 | C9, C11 | 4 |
| 1-6 | C9, C10 | 12 |
| 2-3 | C8, C7 | 8 |
| 2-4 | C8, C6 | 4 |
| 2-5 | C12, C11 | 2 |
| 2-6 | C12, C10 | 6 |
| 3-3 | C21, C23 | 4 |
| 3-4 | C21, C22 | 2 |
| 3-5 | C25, C27 | 1 |
| 3-6 | C25, C26 | 3 |
| 4-3 | C24, C23 | 12 |
| 4-4 | C24, C22 | 6 |
| 4-5 | C28, C27 | 3 |
| 3-6 | C28, C26 | 9 |

TC2 score = 16 + 8 + 8 + 4 = 36
TC3 score = 4 + 12 + 2 + 6 = 24
TC6 score = 4 + 2 + 12 + 6 = 24
TC7 score = 1 + 3 + 3 + 9 = 16

| row # | rank | | column # 3 | 4 | 5 | 6 |
|---|---|---|---|---|---|---|
| | | rank | 4 | 2 | 1 | 3 |
| 1 | 4 | | 16 | 8 | 4 | 12 |
| 2 | 2 | | 8 | 4 | 2 | 6 |
| 3 | 1 | | 4 | 2 | 1 | 3 |
| 4 | 3 | | 12 | 6 | 3 | 9 |

FIG. 26D top view side view side view select coverage of foot area full coverage of foot area key pressure points of foot area

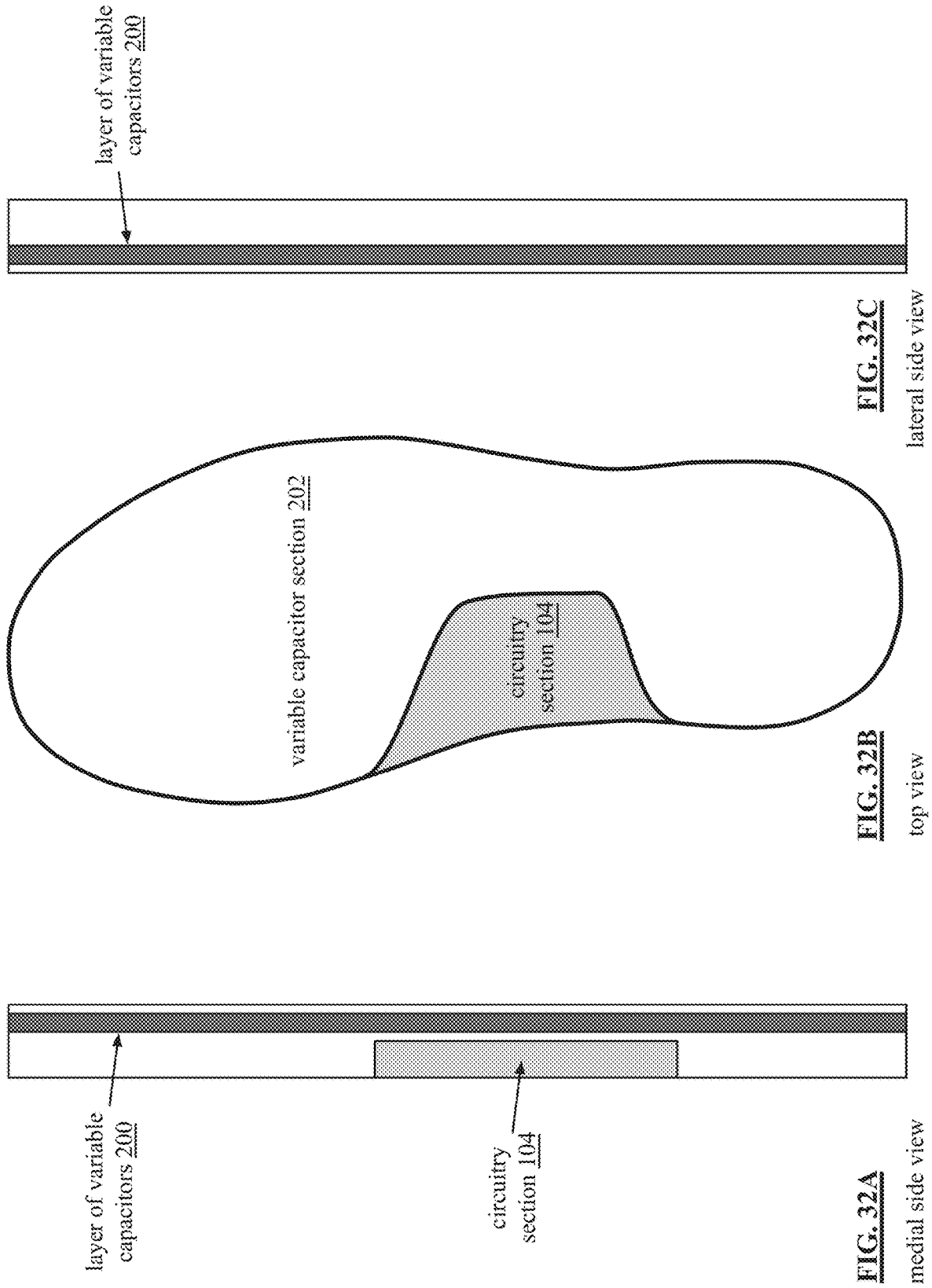

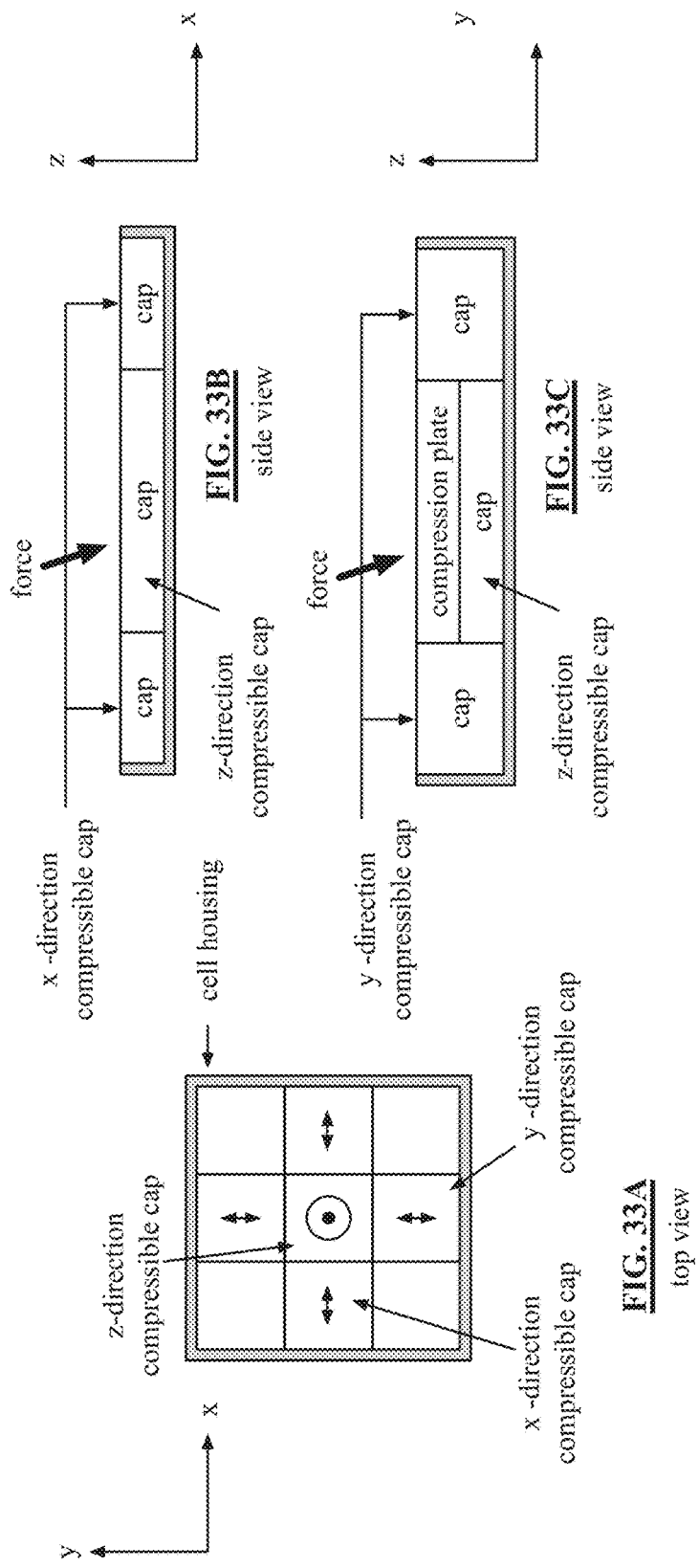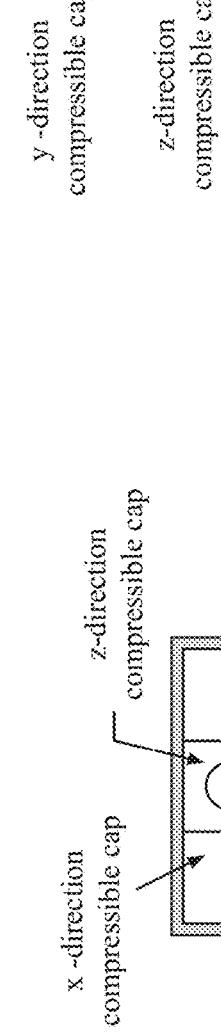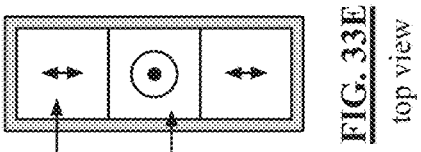

INSOLE XYZ FORCE DETECTION SYSTEM

CROSS-REFERENCE TO RELATED APPLICATIONS

The present U.S. Utility Patent application claims priority pursuant to 35 U.S.C. § 119(e) to U.S. Provisional Application No. 63/202,251, entitled "Insole XYZ Force Detection System", filed Jun. 3, 1921, which is hereby incorporated herein by reference in its entirety and made part of the present U.S. Utility Patent Application for all purposes.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

BACKGROUND OF THE INVENTION

Technical Field of the Invention

This disclosure relates generally to athletic data gathering and analysis and more particularly to force data.

Description of Related Art

Technology is being used more and more to monitor a person's physical activities, rest patterns, diet, and vital signs. Some of this technology is wearable. For example, there are wrist wearable devices to monitor the number of steps a person takes in a day, the approximate distance traveled, heart rate, and/or sleep patterns. As another example, there are chest straps that communicate wirelessly with a module for monitoring heart rate.

As yet another example, there are shoe insert systems to monitor forces of the foot during walking. One such system includes a flexible circuit board insert that includes a resistive sensor grid that is hard wired to a module that straps to the ankle. The two ankle modules are then hard wired to another module that straps to the waist. The waist module collects the data and communicates it to a computer via a wired or wireless connection.

Another technology for monitoring foot force is to use a pressure sensitive mat on which a person stands to perform a physical activity (e.g., golf). The mat detects variations in foot forces during the execution of the physical activity, which is then analyzed to evaluate the performance of the physical activity.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

FIG. 3 is a schematic block diagram of an embodiment of force detection system that is capable of communicating with a computing device;

FIG. 4A is a schematic block diagram of an embodiment of a drive sense circuit coupled to a variable capacitor and to an ADC;

FIG. 4B is a schematic block diagram of an example of a reference signal;

FIGS. 5E-5I are schematic block diagrams of embodiments of computing entities;

FIGS. 6A-6C are schematic block diagrams of an embodiment of force detection system that includes a layer of variable capacitors, a layer of compression plates, and a circuitry section;

FIGS. 6D-6F are schematic block diagrams of another embodiment of force detection system that includes a layer of variable capacitors, a layer of compression plates, and a circuitry section;

FIGS. 8A-8C are schematic block diagrams of an example of force applied by a foot to the force detection system;

FIGS. 9A-9C are schematic block diagrams of another example of force applied by a foot to the force detection system;

FIGS. 10A-10C are schematic block diagrams of another example of force applied by a foot to the force detection system;

FIGS. 11A-11F are schematic block diagrams of another example of forces applied by a foot to the force detection system when a person is running;

FIGS. 14A-14C are schematic block diagrams of an example of a layer of variable capacitors and a layer of compression plates of a force detection system;

FIGS. 15A-15E are schematic block diagrams of an example of a layer of variable capacitors and a layer of compression plates of a force detection system with and without compression of the capacitors;

FIG. 17 is a schematic block diagram of an example of a graph that depicts capacitance variance with respect to compression of a of variable capacitor;

FIGS. 18A-18C are schematic block diagrams of examples of an impact force applied to a cell of a force detection system, wherein the cell includes a compression plate and one or more variable capacitors;

FIGS. 18D-18F are schematic block diagrams of examples of an impact force applied to a cell of a force detection system (e.g., a first layer capacitor and three second layer capacitors);

FIGS. 20A-20D are schematic block diagrams of another example of determining a normal vector of a reference plane of a cell of a force detection system in response to an impact force;

FIGS. 21A-21D are schematic block diagrams of another example of determining a normal vector of a reference plane of a cell of a force detection system in response to an impact force;

FIGS. 22A-22C are schematic block diagrams of an example of determining a plurality of normal vectors of a plurality of reference planes of a plurality of cells of a force detection system in response to an impact force;

FIGS. 26A-26D are schematic block diagrams of an example of determining one or more normal vectors in response to an impact force;

FIGS. 32A-32C are schematic block diagrams of another embodiment of force detection system that includes a layer of variable capacitors, a layer of compression plates, and a circuitry section; and FIGS. 33A-33E are schematic block diagrams of an example of a capacitor cell of the force detection system of FIGS. 32A-32C.

DETAILED DESCRIPTION OF THE INVENTION

Figure 1A:
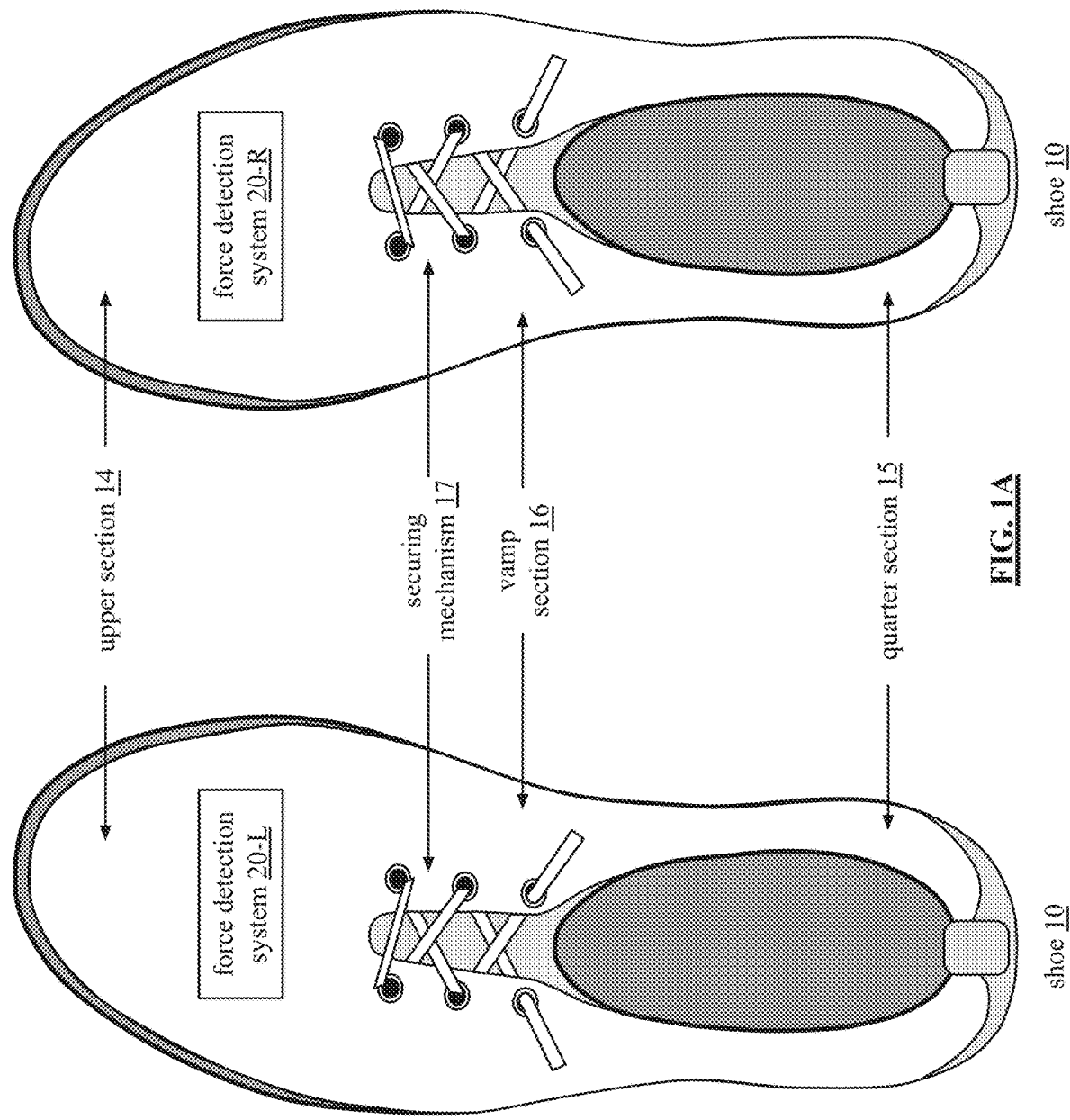
FIG. 1A is a top side view diagram of an embodiment of shoes that include a force detection system.

FIG. 1A is a top side view diagram of an embodiment of shoes 10 that include a force detection system 20. Each shoe includes an upper section 14, a vamp section 16, a quarter section 15, a securing mechanism 17, and at least a portion of the force detection system 20. For example, the left shoe includes a left shoe portion of the force detection system 20-L and the right shoe includes a right shoe portion of the force detection system 20-R.

The upper section 14 includes the vamp section 16, which covers at least a portion of a midfoot area of the shoe, and the quarter section 15, which is the rear portion of the shoe. The vamp section and the quarter section may be constructed from one or more the same materials or one or more of different materials. The materials include, but is not limited to, a leather, a molded plastic, a molded carbon fiber, a polyurethane (PU), a thermoplastic polyurethane (TPU), a faux leather, a PU leather, cloth, etc. In a specific example, the vamp section and the quarter section are constructed of leather. In another specific example, the vamp section is constructed for leather and the quarter section is constructed of a PU leather.

The securing mechanism 17 functions to tighten the shoe 10 around a foot when placed in the shoe 10. The securing mechanism 17 may be implemented in a variety of ways and positioned within the vamp section 16 is a variety of locations. For example, the securing mechanism 17 includes eyelets and a shoelace that is positioned approximately along a center line of the vamp section 16. With respect to FIG. 1A, the center line is approximately along a midline between a medial edge of the shoe and a lateral edge of the shoe running the length of the vamp section 16. In another example, the securing mechanism 17 includes Velcro™ straps. In another embodiment, the securing mechanism 17 includes a Boa' structure.

The force detection system 20 is included in one or both shoes. In general, the force detection system 20 provides X, Y, and/or Z force data of a foot within the shoe with respect to the ground. The force data can be used to evaluate human movement, which includes athletic movement. For a body to move, it applies a force on the ground and the ground pushes back with an equal and opposite force. The ground pushing back is called ground reaction force, which traverses through the shoes.

The direction and magnitude of ground reaction force effect human movement, especially athletic movements. Performance of almost every athletic movement is improved by increasing power and/or increasing consistency. Power is a function of energy divided by time. Energy is a function of force excreted over a distance. Thus, power is a function of force exerted over a distance in a given time frame. As such, power is increased by increasing the force, increasing the distance, and/or reducing the time frame.

For an athletic movement, the force is ground reaction force. As such, an athlete's power is a function of the ground reaction force being used to move the body, and may further includes moving an object (e.g., a club, a bat, a ball, a racket, etc.), over a distance in a given time frame. Thus, improving ground reaction force for the same distance and time of movement, improves an athlete's power. Accordingly, determining the magnitude of ground reaction force during an athletic movement is an important data point for improving athletic performance.

In athletics, consistency involves being able to move the body in a nearly identical matter time after time. The direction of the ground reaction force effects an athlete's consistency. Ideally, an athlete wants the direction of the ground reaction force to be parallel to the line of the legs. In the ideal case, there is no wasted force, all of it is going into the body. It also keeps the body in the properly alignment for the athletic movement (e.g., a golf swing).

The more the direction of the ground reaction force deviates from parallel to the leg, the more of it is wasted and the more the athlete has to compensate for the deviation. Having to compensate for ground reaction force's angle deviation adds an extra element to the athletic movement, which too must be executed nearly identical time after time to achieve the desired athletic consistency. Thus, determining the direction of ground reaction force during an athletic movement is an important data point for improving athletic performance.

Commercially available foot force systems suffer from one or more of the following. (a) Due to the bulk of the system, it cannot be used in game or in practice. It has to be used in a lab setting. (b) The force sensors break down too quickly for elite athletes. When an athlete jumps, they can have a landing impact of six times their body weight. For a professional football player that weighs over three hundred pounds, that's a landing force per jump of almost one ton. Most sensors are design for a walking impact of about two times the body weight, hence they fail quickly when used by elite athletes. (c) The batteries of a system need to be recharged too frequently. Most athletes, especially at the elite level, won't recharge the batteries on a regular basis (e.g., daily, every other day, multiple times per day, etc.). (d) The system only provides Z force information; there is no angular information, only magnitude information in the Z direction. (e) The system has a low sampling rate (e.g., a few hundred Hertz), thus high-speed data is often missed or incomplete. For example, the foot strike of a sprinter happens in 10's of milliseconds; with a 200 Hertz sampling rate, that's one sample per 5 milliseconds, thus, very few samples will be captured for each foot strike, which will miss the granularity and force transition of a foot strike.

The force detection system 20 is a force system that can be used in game and/or in practice. A capacitor-based sensor array allows for hundreds to thousands of hours of reliable use. The force detection system is ultra-low power such that the batteries can be charged infrequently. The force detection system provides X, Y, and Z force data such that direction and magnitude of ground reaction force can be determined and evaluating with respect to athletic performance. The force detection system is capable of sampling data in the thousands to tens of thousands of Hertz so a significant number of data points is obtained for each foot strike.

Figure 1B:
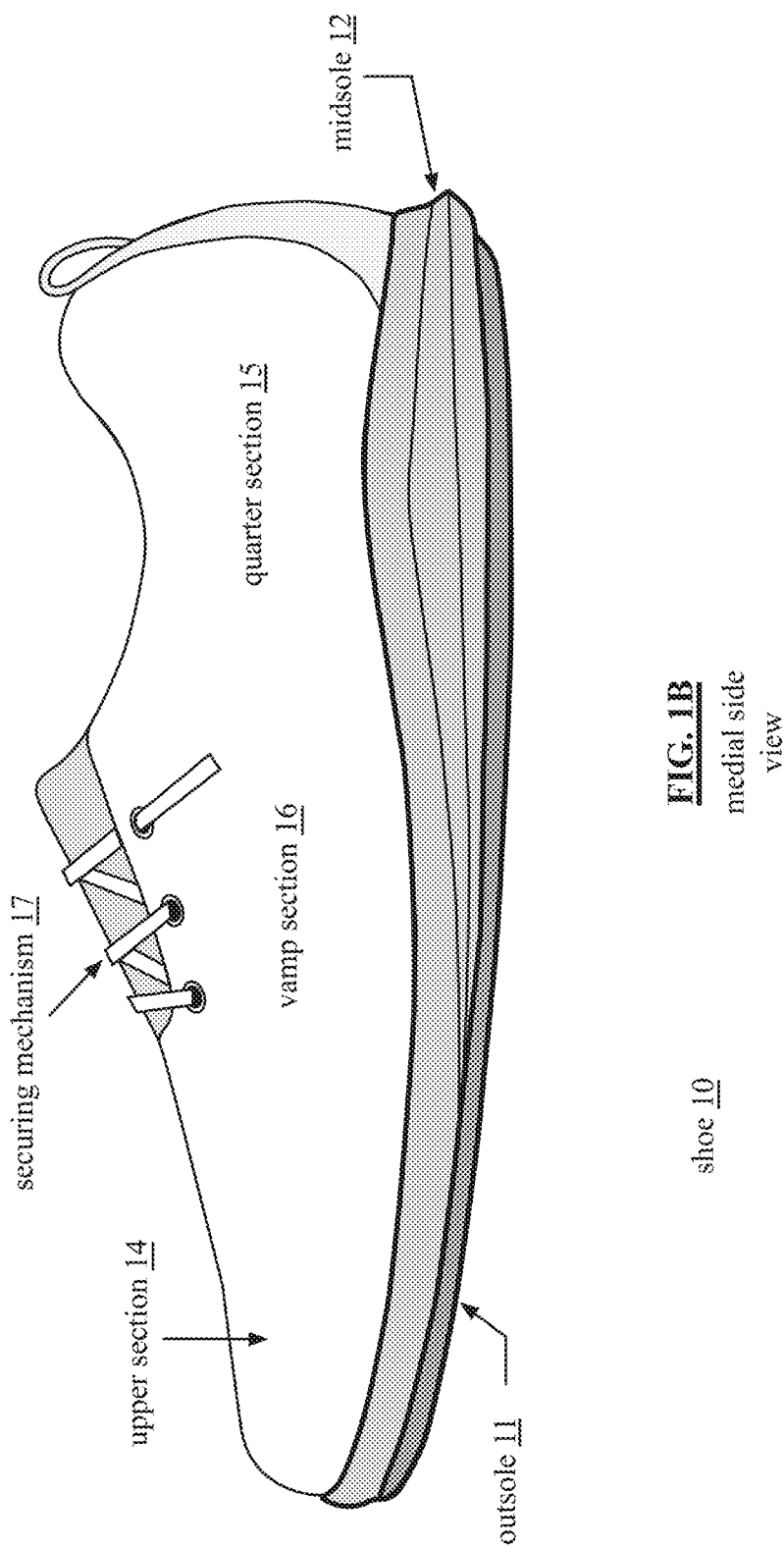
FIG. 1B is a medial side view diagram of an embodiment of a shoe of FIG. 1A.

FIG. 1B is a medial side view diagram of an embodiment of a shoe 10 of FIG. 1A. In this view, the shoe 10 is further shown to include a midsole 12 and an outsole 11. The midsole 12 is constructed of one or more materials that include, but is not limited to, Ethylene-vinyl acetate (EVA), poly (ethylene-vinyl acetate) (PEVA), rubber, carbon fiber, cork, etc.

The outsole 11 is constructed of one or more materials that include, but is not limited to, rubber, EVA, PEVA, TPU, carbon fiber, plastic, etc. For an athletic shoe, the outsole 11 includes a tread pattern for a particular sport. For example, the tread pattern for a baseball shoe includes plastic and/or metal cleats arranged to provide traction for running, throwing, hitting, and/or fielding in grass, in dirt, and/or on artificial surface. As another example, a training shoe will have a tread pattern for weightlifting, cardio activities, etc. that occur on a gym floor (e.g., wood, concrete, carpet, etc.).

Figure 2:
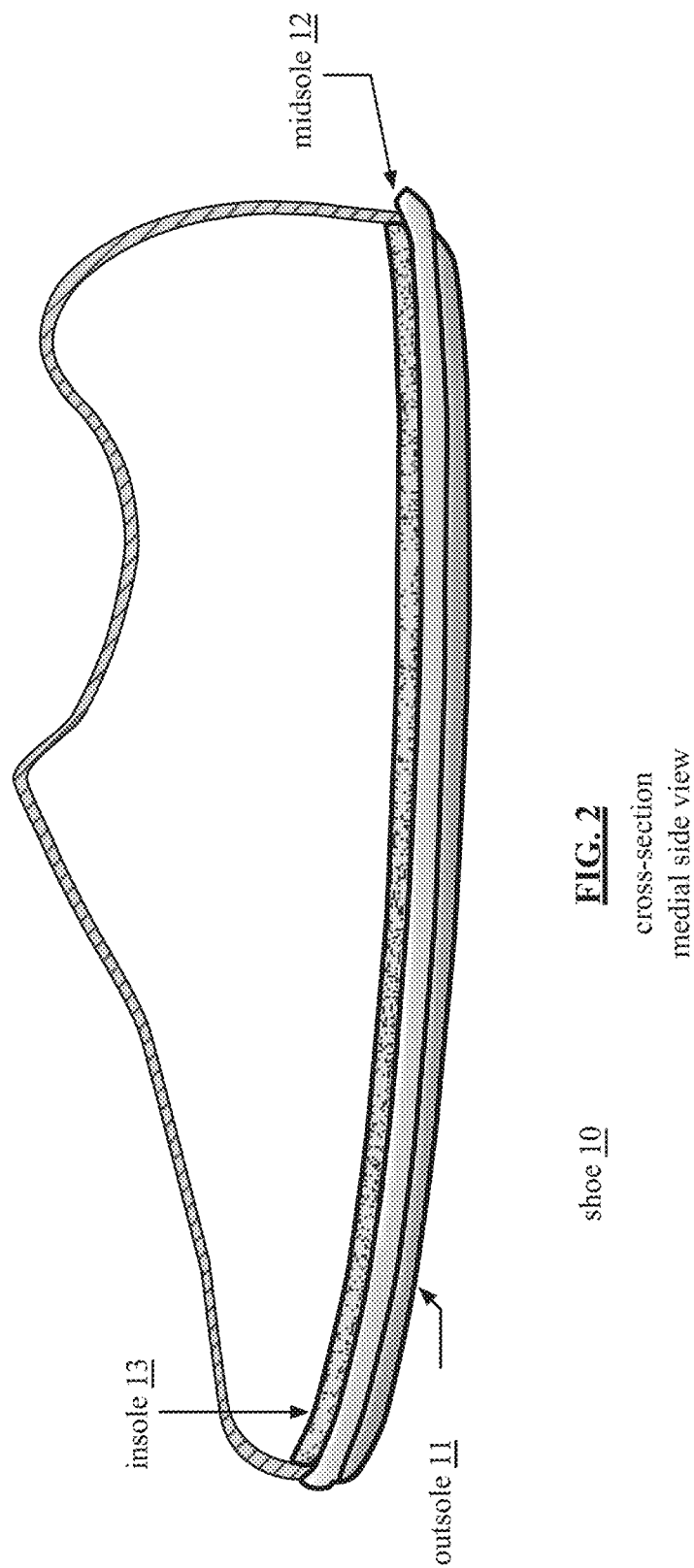
FIG. 2 is a schematic block diagram of a cross-section an embodiment of a shoe including a force detection system.

FIG. 2 is a schematic block diagram of a cross-section an embodiment of a shoe 10. As shown, the sole of the shoe 10 includes the outsole 11, the midsole 12, and/or an insole 13. The force detection system 20, or portion thereof, may be housed in the insole, the midsole, and/or the outsole. For example, pressure sensors are housed in the insole and the circuitry is housed in the midsole.

FIG. 3 is a schematic block diagram of an embodiment of force detection system 20, 20-L, and/or 20-R that is capable of communicating with a computing entity 35. A computing entity 35 includes one or more computing devices 40 as shown in one or more of FIGS. 5E through 5I. The computing device 40 is implemented as shown in one or more of FIGS. 5A through 5F.

The force detection system 20 includes capacitor sensors 21, a drive sense module 22, digital filtering circuit 23, memory 24, a clock circuit 25, a controller 26, a communication circuit 27, and a power source 28. The capacitor sensors 21 are positioned within the shoe to sense pressure between a foot and the ground through the shoe. A force detection system 20 may include a few capacitor sensors per shoe to scores of capacitor sensors per shoe. Various embodiments of the capacitor sensors and their positioning are discussed with reference to one or more of FIGS. 12-31, 33, and 34.

The drive sense module 22 includes a plurality of drive sense circuits, where a drive sense circuit is coupled to one or more capacitor sensors 21 (e.g., variable capacitors). The drive sense circuit 22 provides power to a capacitor sensor and senses capacitance changes of the sensor 21 due to pressure applied on the capacitor. An embodiment of the drive sense circuit 22 is described in greater detail with reference to FIG. 4A.

The digital filtering circuit 23, which may be implemented by a processing module, converts digital signals it receives from a drive sense circuit 22 into a digital value that is representative of a characteristic of the variable capacitor (e.g., impedance, capacitance, impedance change, capacitance change, etc.). The digital filtering circuit 23 provides a digital value per sampling of the capacitor sensor 21 to the memory 24 for storage therein.

The memory 24 includes volatile and/or non-volatile memory. The memory also stores operational instructions to enable the system 20 to sense and store data. The operational instructions may further include an instruction set regarding the processing of stored capacitance data to produce force data. Examples of converting capacitance data into force data will described with reference to one or more of the subsequent figures.

The controller 26, which, in an embodiment, is implemented via a processing module as defined herein, coordinates the operation of the force detection system 20. For example, the controller executes the operational instructions that enable operation of the system. In addition, the controller 26 enables the clock circuit 25 to generate a sampling clock, a real-time clock, and digital clock.

The sampling clock includes a crystal oscillator, or the like, to provide a reference clock and further includes one or more phased locked loops (PLL) to generate the desired clock signals. For example, the clock circuit generates the sampling clock to establish a rate for sampling the capacitor sensors. The sampling rate may equal the sampling clock, it may be a multiple of the sampling clock, or a fraction of the sampling clock.

The digital clock is used by the controller 26 and memory 24. Depending on the amount of data to be stored and/or processed, the digital clock can be set at a few MHz or hundreds of MHz or higher. It can also be adjustable to balance power consumption with data storage and/or data processing efficiency.

The controller uses the real-time clock to timestamp the data being stored in memory. The real time clock is synced with a reference real time clock so that the foot force data and can time aligned with a recording of body movements.

The controller 26 instructs the communication circuit 27 to output stored data from the memory 24 to the computing entity. The communication circuit 27 is a wired and/or wireless transceiver. For example, a wired communication circuit 27 is an I²C (inter integrated circuit) communication unit, an SPI (serial peripheral interface) communication unit, a CAN (controller area network) communication unit, a USB (universal serial bus) communication unit, a UART (universal asynchronous receiver/transmitter) communication unit, an IEEE 1394 communication unit, etc. As another example, a wireless communication circuit 27 is a Bluetooth communication unit, a wireless local area network communication unit, a Zigbee communication unit, a Z-wave communication unit, a low power wireless personal area network, a radio frequency identification (RFID) communication unit, a near field communication unit, etc.

The power source 28 includes one or more batteries and provides power to the other components of the system 20. The power source 28 may further include a power supply, a battery charger, a power harvesting circuit, and/or a power management module. The power supply functions to convert the battery voltage into one or more DC voltages ranging from 0.5 volts to 5 volts or more. The power supply may be implemented in a variety of ways. As an example, the power supply is a linear regulator. As another example, the power supply is a buck power supply. As another example, the power supply is a boost power supply.

The power harvesting circuit may be implemented in a variety of ways and may include a variety of implementations. In an example, the power harvesting circuit functions to generate a DC voltage from one or more radio frequency (RF) signals, such as a cell phone signal, a Bluetooth signal, an RFID signal, etc. In another example, the power harvesting circuit functions to generate a DC voltage from compression of a piezoelectric material in the shoe and the wearer applies force on the shoe. In another example, the power harvesting circuit functions to generate a DC voltage from heat of the wearer.

FIG. 4A is a schematic block diagram of an embodiment of a drive sense circuit 22 coupled to a variable capacitor 21-1 of the capacitive sensors 21. The drive sense circuit (DSC) 22 includes an operational amplifier (op amp) 30, a feedback circuit 31, a dependent current source, and an analog-to-digital converter (ADC) 35. The op amp 30 receives a reference signal 29, which as shown in FIG. 4B, includes a DC component 33 and an oscillating component 34.

The magnitude and frequency of the oscillating component 34 vary depending on the desired resolution of sensing capacitance differences and on achieving minimal power consumption. For example, since power equals voltage times current, minimal voltage and minimal current are needed for minimal power consumption. Voltage is tied to the granularity of sensing capacitance change and current is tied to the impedance of the capacitor and the voltage. With high signal-to-noise (SRN) of the drive sense circuit and subsequent filtering, micro-voltages of change can be detected. To have a current in the micro-amps, the frequency of the oscillating component is determined to provide an impedance of the capacitor that produces a micro-volt scale change from a micro-amp scale current source.

Returning to FIG. 4A, the op amp 30 ideally functions to force the voltages on its inputs to be the same. Thus, the voltage on the input coupled to the variable capacitor 21-1 is the same as the voltage of the reference signal 29. Since no current flows into an op amp 30, the current produced by dependent current source 32 flows into the variable capacitor 21-1. As the impedance of the variable capacitor changes, the dependent current source 32, based on a signal from the feedback circuit 31, produces a varying current to keep the voltage of the variable capacitor matching that of the reference signal 29.

The feedback circuit 31, which includes one or more components to provide a loop gain of unit to open loop, scales the output of the op amp 30 to provide the control signal to the dependent current source 32. The output of the op amp 30 is a voltage that represents the impedance of the variable capacitor 21-1 and changes of the impedance. With the force detection system 20, the variable capacitor changes it capacitance based on pressure. In an embodiment, as pressure on the capacitor increases, its capacitance increases (e.g., plates get closer together and/or dielectric changes), which decreases the capacitor's impedance. In another embodiment, as pressure on the capacitor decreases, its capacitance decreases (e.g., plates get further apart and/or dielectric changes), which increases the capacitor's impedance.

The analog to digital converter (ADC) 23 converts the output of the op amp 30 into unfiltered digital values. For a sigma delta ADC, the digital values are a stream of one-bit digital values. The digital filtering circuit 23, which, in an embodiment, includes a bandpass filter and a decimation filter, converts the stream of one-bit digital values into digital words at a desired sampling rate. The digital words are stored in the memory 24.

Figure 5A:
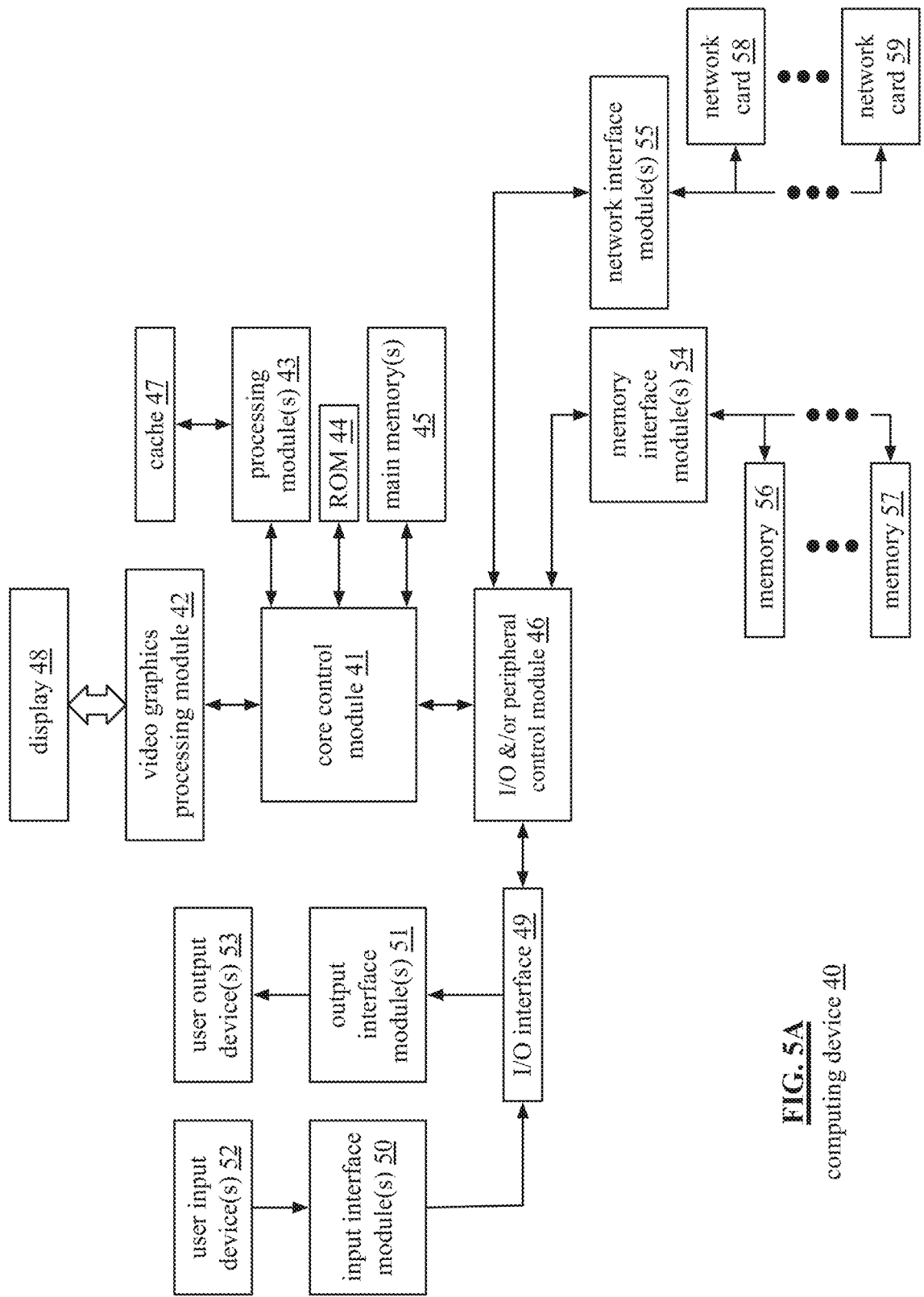
FIGS. 5A-5D are schematic block diagrams of embodiments of computing devices.

FIG. 5A is a schematic block diagram of an embodiment of a computing device 40 that includes a plurality of computing resources. The computing resource include a core control module 41, one or more processing modules 43, one or more main memories 45, a read only memory (ROM) 44 for a boot up sequence, cache memory 47, a video graphics processing module 42, a display 48 (optional), an Input-Output (I/O) peripheral control module 46, an I/O interface module 49 (which could be omitted), one or more input interface modules 50, one or more output interface modules 51, one or more network interface modules 55, and one or more memory interface modules 54. A processing module 43 is described in greater detail at the end of the detailed description section and, in an alternative embodiment, has a direction connection to the main memory 45. In an alternate embodiment, the core control module 41 and the I/O and/or peripheral control module 46 are one module, such as a chipset, a quick path interconnect (QPI), and/or an ultra-path interconnect (UPI).

Each of the main memories 45 includes one or more Random Access Memory (RAM) integrated circuits, or chips. For example, a main memory 45 includes four DDR4 (4$^{th}$ generation of double data rate) RAM chips, each running at a rate of 2,400 MHz. In general, the main memory 45 stores data and operational instructions most relevant for the processing module 43. For example, the core control module 41 coordinates the transfer of data and/or operational instructions between the main memory 45 and the memory 56-57. The data and/or operational instructions retrieve from memory 56-57 are the data and/or operational instructions requested by the processing module or will most likely be needed by the processing module. When the processing module is done with the data and/or operational instructions in main memory, the core control module 41 coordinates sending updated data to the memory 56-57 for storage.

The memory 56-57 includes one or more hard drives, one or more solid state memory chips, and/or one or more other large capacity storage devices that, in comparison to cache memory and main memory devices, is/are relatively inexpensive with respect to cost per amount of data stored. The memory 56-57 is coupled to the core control module 41 via the I/O and/or peripheral control module 46 and via one or more memory interface modules 54. In an embodiment, the I/O and/or peripheral control module 46 includes one or more Peripheral Component Interface (PCI) buses to which peripheral components connect to the core control module 41. A memory interface module 54 includes a software driver and a hardware connector for coupling a memory device to the I/O and/or peripheral control module 46. For example, a memory interface 54 is in accordance with a Serial Advanced Technology Attachment (SATA) port.

The core control module 41 coordinates data communications between the processing module(s) 43 and the network(s) 14 via the I/O and/or peripheral control module 46, the network interface module(s) 55, and a network card 58 or 59. A network card 58 or 59 includes a wireless communication unit or a wired communication unit. A wireless communication unit includes a wireless local area network (WLAN) communication device, a cellular communication device, a Bluetooth device, and/or a ZigBee communication device. A wired communication unit includes a Gigabit LAN connection, a Firewire connection, and/or a proprietary computer wired connection. A network interface module 55 includes a software driver and a hardware connector for coupling the network card to the I/O and/or peripheral control module 46. For example, the network interface module 55 is in accordance with one or more versions of IEEE 802.11, cellular telephone protocols, 10/100/1000 Gigabit LAN protocols, etc.

The core control module 41 coordinates data communications between the processing module(s) 43 and input device(s) 52 via the input interface module(s) 50, the I/O interface 49, and the I/O and/or peripheral control module 46. An input device 52 includes a keypad, a keyboard, control switches, a touchpad, a microphone, a camera, etc. An input interface module 50 includes a software driver and a hardware connector for coupling an input device to the I/O and/or peripheral control module 46. In an embodiment, an input interface module 50 is in accordance with one or more Universal Serial Bus (USB) protocols.

The core control module 41 coordinates data communications between the processing module(s) 43 and output device(s) 53 via the output interface module(s) 51 and the I/O and/or peripheral control module 46. An output device 53 includes a speaker, auxiliary memory, headphones, etc. An output interface module 51 includes a software driver and a hardware connector for coupling an output device to the I/O and/or peripheral control module 46. In an embodiment, an output interface module 46 is in accordance with one or more audio codec protocols.

The processing module 43 communicates directly with a video graphics processing module 42 to display data on the display 48. The display 48 includes an LED (light emitting diode) display, an LCD (liquid crystal display), and/or other type of display technology. The display has a resolution, an aspect ratio, and other features that affect the quality of the display. The video graphics processing module 42 receives data from the processing module 43, processes the data to produce rendered data in accordance with the characteristics of the display, and provides the rendered data to the display 48.

Figure 5B:
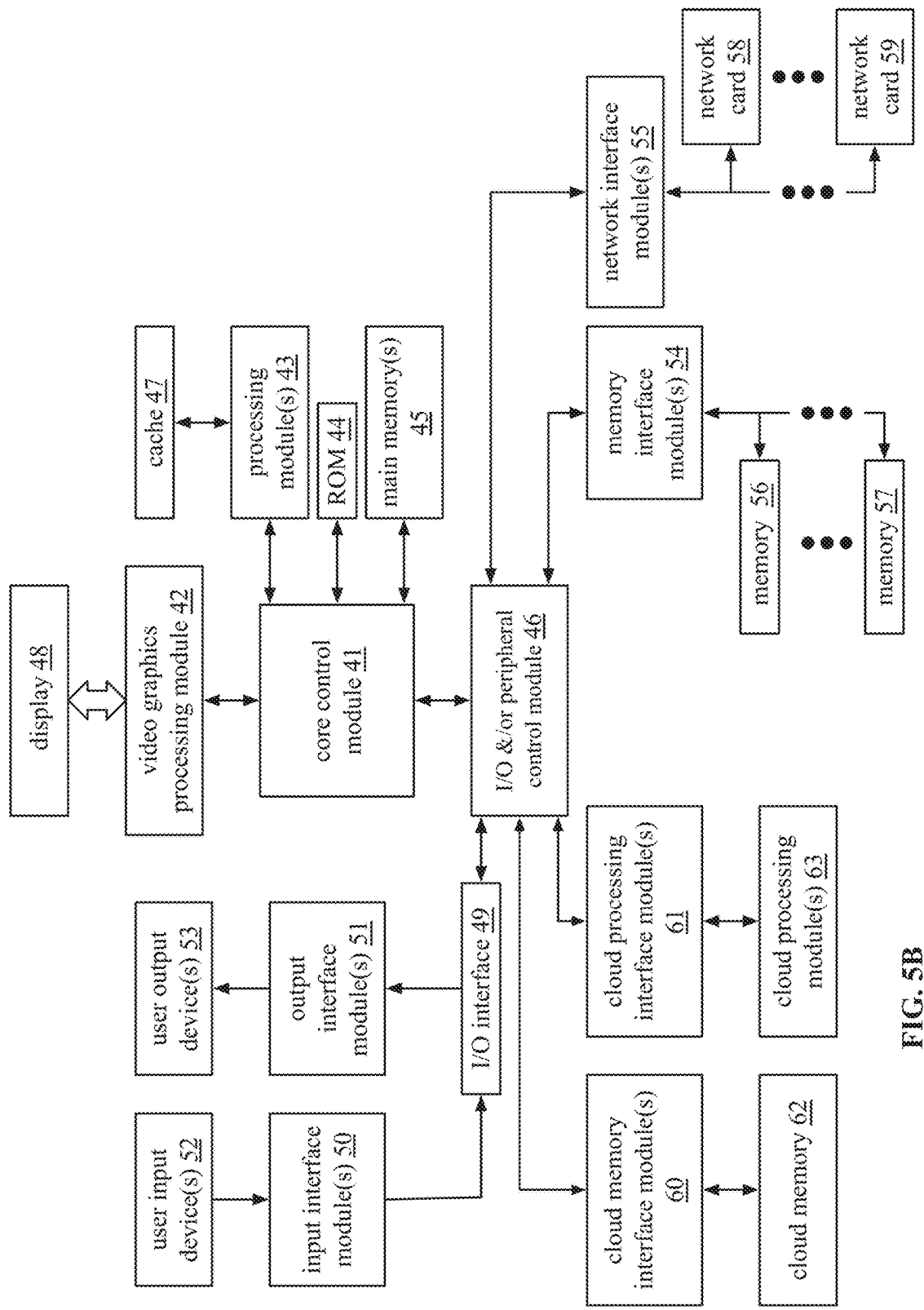

FIG. 5B is a schematic block diagram of an embodiment of a computing device 40 that includes a plurality of computing resources similar to the computing resources of FIG. 2A with the addition of one or more cloud memory interface modules 60, one or more cloud processing interface modules 61, cloud memory 62, and one or more cloud processing modules 63. The cloud memory 62 includes one or more tiers of memory (e.g., ROM, volatile (RAM, main, etc.), non-volatile (hard drive, solid-state, etc.) and/or backup (hard drive, tape, etc.)) that is remoted from the core control module and is accessed via a network (WAN and/or LAN). The cloud processing module 63 is similar to processing module 43 but is remoted from the core control module and is accessed via a network.

Figure 5C:
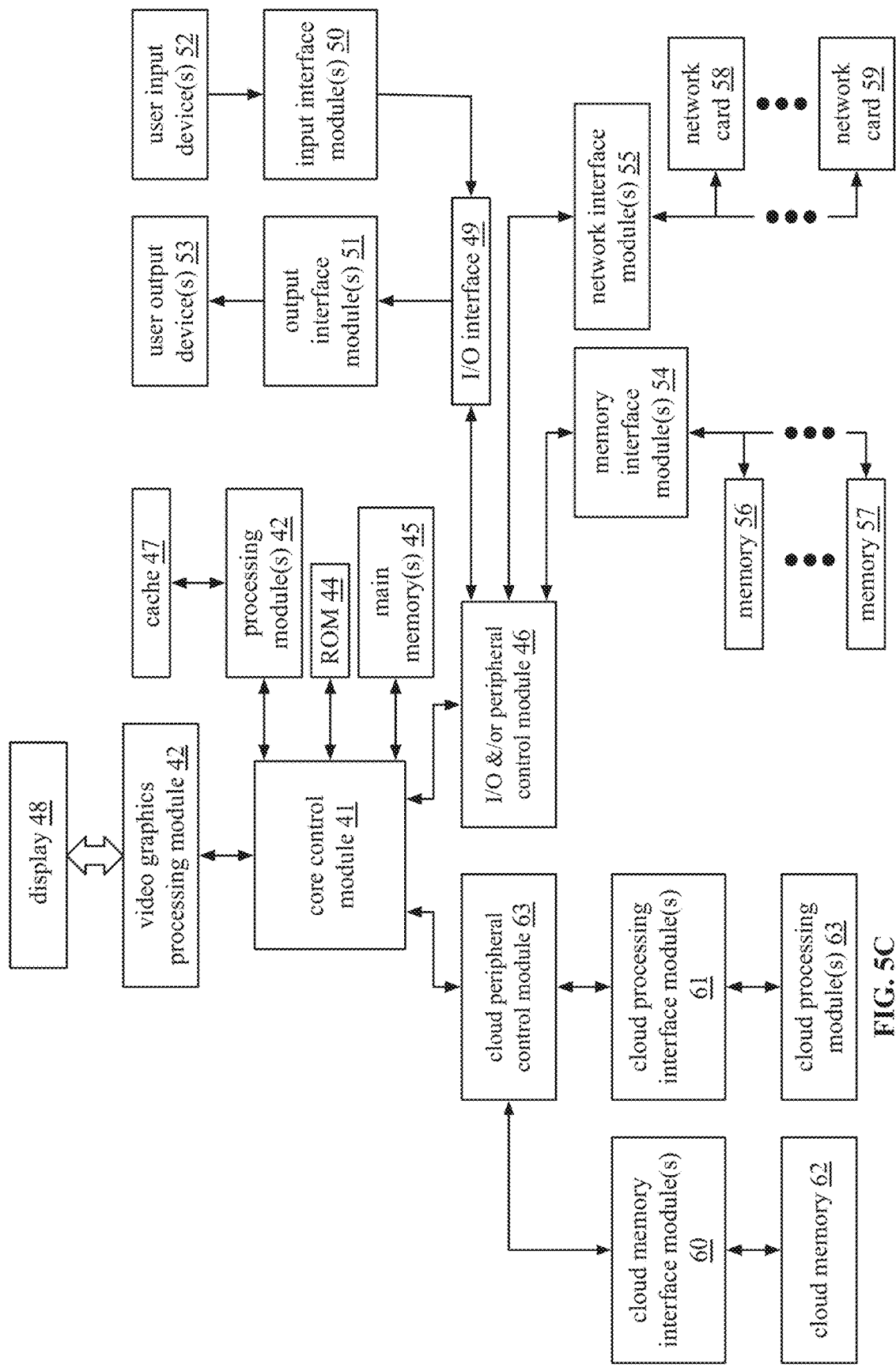

FIG. 5C is a schematic block diagram of an embodiment of a computing device 40 that includes a plurality of computing resources similar to the computing resources of FIG. 2B with a change in how the cloud memory interface module(s) 60 and the cloud processing interface module(s) 61 are coupled to the core control module 41. In this embodiment, the interface modules 60 and 61 are coupled to a cloud peripheral control module 63 that directly couples to the core control module 41.

Figure 5D:
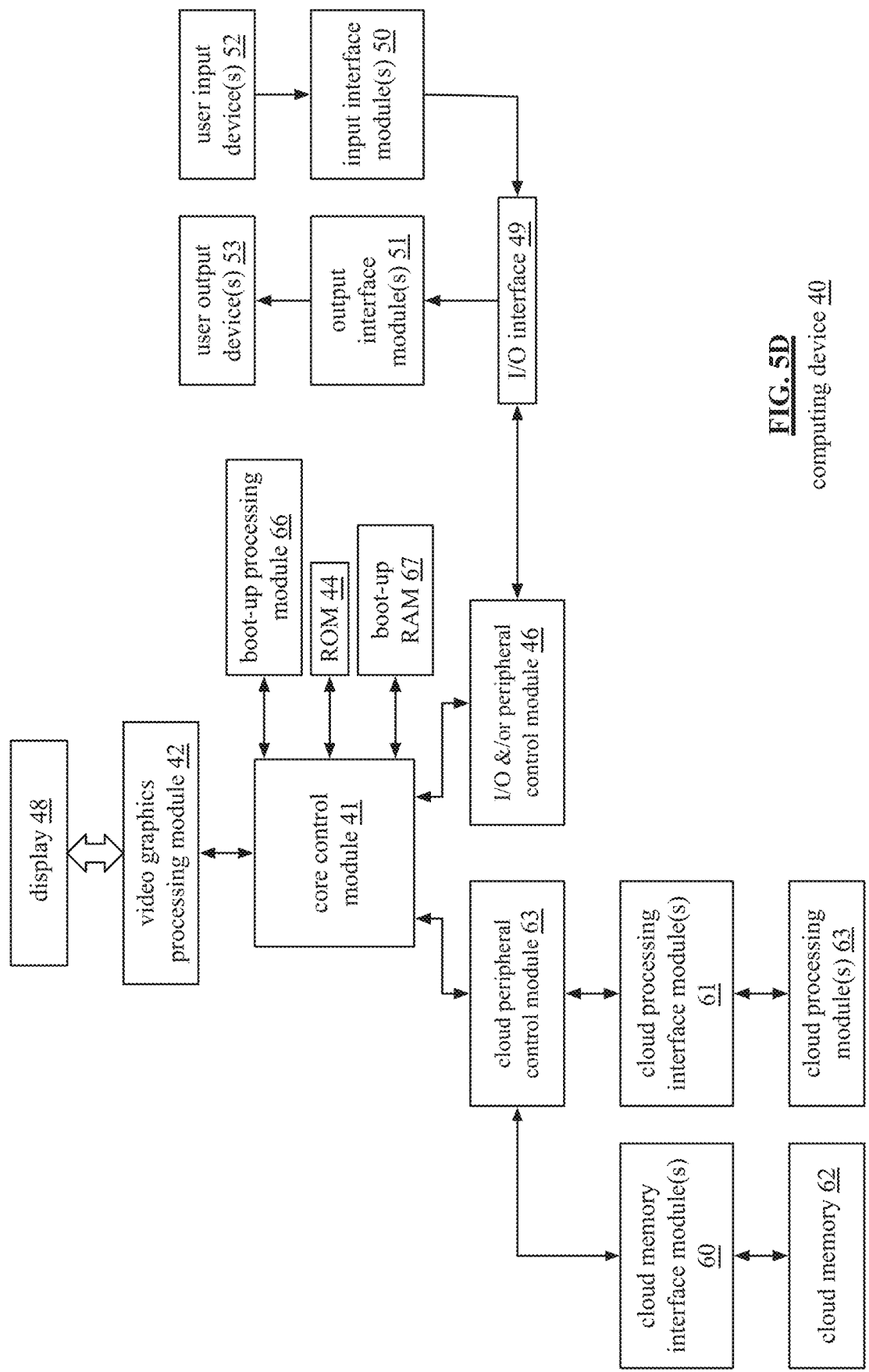

FIG. 5D is a schematic block diagram of an embodiment of a computing device 40 that includes a plurality of computing resources, which includes include a core control module 41, a boot up processing module 66, boot up RAM 67, a read only memory (ROM) 45, a video graphics processing module 42, a display 48 (optional), an Input-Output (I/O) peripheral control module 46, one or more input interface modules 50, one or more output interface modules 51, one or more cloud memory interface modules 60, one or more cloud processing interface modules 61, cloud memory 62, and cloud processing module(s) 63.

In this embodiment, the computing device 40 includes enough processing resources (e.g., module 66, ROM 44, and RAM 67) to boot up. Once booted up, the cloud memory 62 and the cloud processing module(s) 63 function as the computing device's memory (e.g., main and hard drive) and processing module.

FIG. 5E is schematic block diagram of an embodiment of a computing entity 16 that includes a computing device 40 (e.g., one of the embodiments of FIGS. 2A-2D). A computing device may function as a user computing device, a server, a system computing device, a data storage device, a data security device, a networking device, a user access device, a cell phone, a tablet, a laptop, a printer, a game console, a satellite control box, a cable box, etc.

FIG. 5F is schematic block diagram of an embodiment of a computing entity 16 that includes two or more computing devices 40 (e.g., two or more from any combination of the embodiments of FIGS. 2A-2D). The computing devices 40 perform the functions of a computing entity in a peer processing manner (e.g., coordinate together to perform the functions), in a master-slave manner (e.g., one computing device coordinates and the other support it), and/or in another manner.

FIG. 5G is schematic block diagram of an embodiment of a computing entity 16 that includes a network of computing devices 40 (e.g., two or more from any combination of the embodiments of FIGS. 2A-2D). The computing devices are coupled together via one or more network connections (e.g., WAN, LAN, cellular data, WLAN, etc.) and preform the functions of the computing entity.

FIG. 5H is schematic block diagram of an embodiment of a computing entity 16 that includes a primary computing device (e.g., any one of the computing devices of FIGS. 2A-2D), an interface device (e.g., a network connection), and a network of computing devices 40 (e.g., one or more from any combination of the embodiments of FIGS. 2A-2D). The primary computing device utilizes the other computing devices as co-processors to execute one or more the functions of the computing entity, as storage for data, for other data processing functions, and/or storage purposes.

FIG. 5I is schematic block diagram of an embodiment of a computing entity 16 that includes a primary computing device (e.g., any one of the computing devices of FIGS. 2A-2D), an interface device (e.g., a network connection) 70, and a network of computing resources 71 (e.g., two or more resources from any combination of the embodiments of FIGS. 2A-2D). The primary computing device utilizes the computing resources as co-processors to execute one or more the functions of the computing entity, as storage for data, for other data processing functions, and/or storage purposes.

FIGS. 6A-6C are a medial side, top view, and lateral side view diagrams of an embodiment of force detection system 20 implemented in the sole of a shoe. The force detection system 20 includes a layer of variable capacitors 100, a layer of compression plates 102, and a circuitry section 104. The layer of variable capacitors 100 and the layer of compression plates 102 are positioned within the variable capacitor section 106.

The circuitry section 104 includes the circuit components of the force detection system 20 as shown in FIG. 3, excluding the capacitor sensors 21. The circuit components may be discrete components and/or included in an integrated circuit (IC). For example, the drive sense circuits and digital filtering circuitry are implemented as an integrated circuit. The circuitry components, as ICs and/or discrete components, are mounted on one or more circuit boards (e.g., rigid and/or flexible) that fit within the circuitry section 104.

The capacitor sensors 21 include the layer of variable capacitors 100 and the layer of compression plates 102. The compression plates are positioned closer to the foot than the variable capacitors. When a force is applied to a compression plate as a result of a person wearing a shoe, the compression plate pushes on a set of variable capacitors. The magnitude and angle of the force applied to the compression plate is calculable based on the changes to the capacitances of the set of variable capacitors. One or more examples will be described with reference to at least one subsequent figure.

FIGS. 6D-6F are a medial side, top view, and lateral side view diagrams of an embodiment of force detection system 20 implemented in the sole of a shoe. The force detection system 20 includes a first layer of variable capacitors 100, a second layer of variable capacitors 108, and a circuitry section 104. The first and second layers of variable capacitors 100 and 108 are positioned within the variable capacitor section 106. The circuitry section 104 includes the circuit components of the force detection system 20 as shown in FIG. 3, excluding the capacitor sensors 21, as previously discussed.

The capacitor sensors 21 include the first and second layers of variable capacitors 100 and 108. The first layer of variable capacitors is positioned closer to the foot than the first layer of variable capacitors. When a force is applied to a variable capacitor of the first layer as a result of a person wearing a shoe, the first layer variable capacitor pushes on a set of second layer variable capacitors. The magnitude and angle of the force applied to the first layer variable capacitor is calculable based on the changes to the capacitances of the first layer variable capacitor and set of second layer variable capacitors. One or more examples will be described with reference to at least one subsequent figure.

Figure 7C:
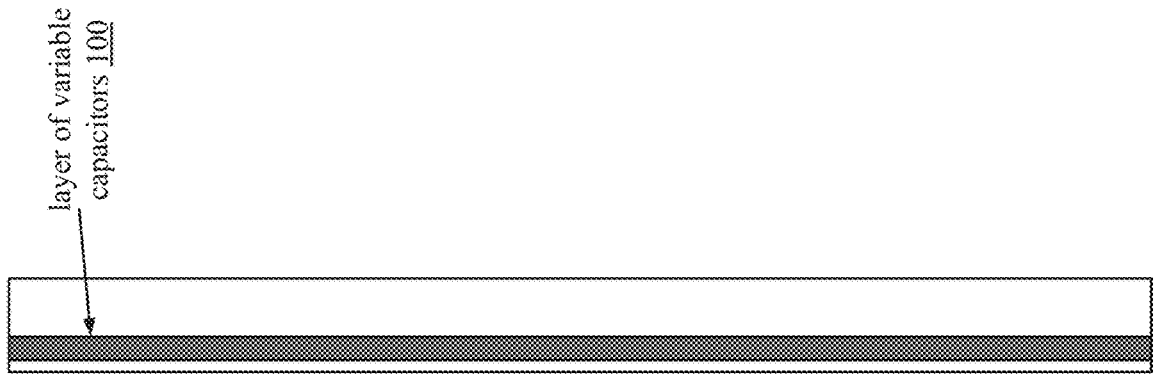
FIGS. 7A-7C are schematic block diagrams of an embodiment of force detection system that includes a layer of variable capacitors and a circuitry section.
Figure 7B:
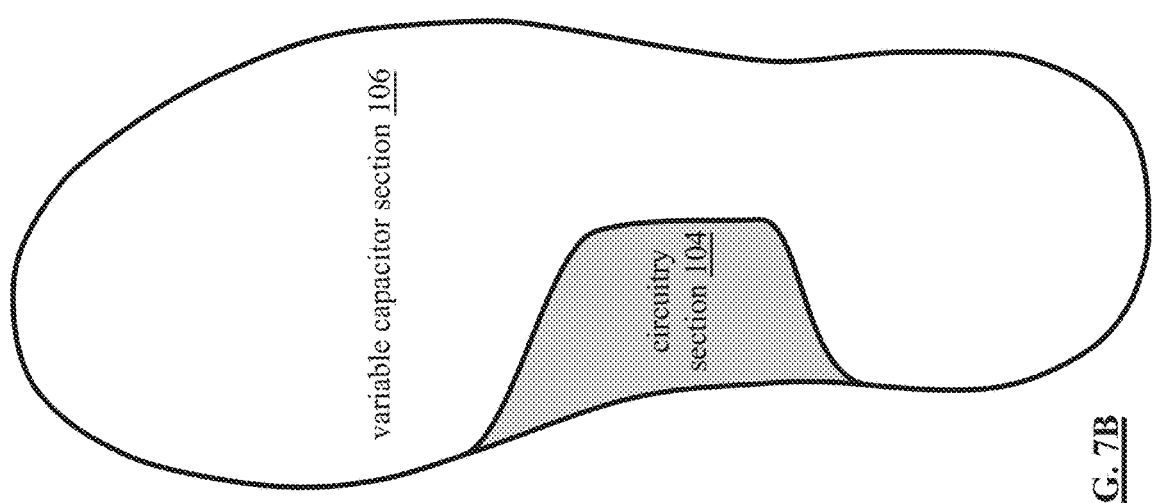
Figure 7A:
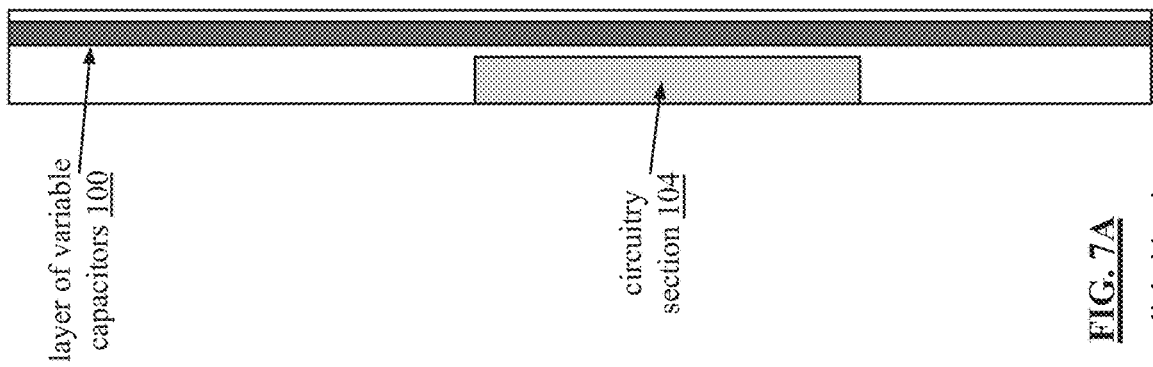

FIGS. 7A-7C are a medial side, top view, and lateral side view diagrams of an embodiment of force detection system 20 implemented in the sole of a shoe. The force detection system 20 includes a layer of variable capacitors 100 and a circuitry section 104. The layer of variable capacitors 100 is positioned within the variable capacitor section 106. The circuitry section 104 includes the circuit components of the force detection system 20 as shown in FIG. 3, excluding the capacitor sensors 21, as previously discussed.

The capacitor sensors 21 include the layer of variable capacitors 100. When a force is applied to a set of variable capacitors as a result of a person wearing a shoe, the set of variable capacitors are compressed. The magnitude and angle of the force applied to the set of variable capacitors is calculable based on the changes to the capacitances of the set of variable capacitors. One or more examples will be described with reference to at least one subsequent figure.

FIGS. 8A-8C are front, side, and top views of an example of force applied by a foot to the force detection system 20 when a wearer is standing. With a wearer standing, the force applied to the shoe is normal to the ground in the front view and in the top view, and it's distributed between the forefoot and the heel. The force applied to the shoe is weight & muscle contraction of the wearer and is represented by a red arrow. With the wearer standing, there is little to no muscle contraction force, thus the force is primarily a weight force.

The weight force traverses through the insole 13, the midsole 12, and the outsole 11 of a shoe to the ground 110. The ground pushes back with an equal and opposite force with ground reaction force, which is represented by a green arrow. To help illustrate the mirroring nature of the weight and muscle contraction force and the ground reaction force, the complementary colors of green and red are used.

In the side view of FIG. 8, the midsole 12 includes an angular section that slopes upward from the toes to the heel. The angular section shifts, from the side view perspective, how the weight and muscle contraction force traverses through the shoe to the ground 110. As shown, the red weight and muscle contraction force is at an angle to ground. The angle of the force is orthogonal to the angle of the midsole 12. The green ground reaction force is equal and opposite to the weight and muscle contraction force and includes a commentary angle.

With the force detection system 20 implemented in the sole of the shoe (e.g., in the insole, midsole, and/or outsole), the magnitude and direction of the weight and muscle contraction force and the ground reaction force can be determined. This is a vast improvement over conventional foot force analysis systems that only measure the normalized magnitude of the force (i.e., the resulting Z component of the force), not the true magnitude of the force. Examples of computing the magnitude and direction of the forces will be discussed with reference to one or more subsequent figures.

FIGS. 9A-9C are front, side, and top views of an example of force applied by a foot to the force detection system 20 when a wearer is executed a lateral push-off. A wide variety of athletes execute a lateral push-off in playing their respective sport. For example, a golfer executes a lateral push-off on the back leg during the backswing and down swing and then on the front leg during the follow through. A baseball player goes through a similar lateral push-off for hitting and for pitching. A tennis player uses a lateral push-off to hit a tennis ball, but also to stop or change directions while running. A football player, a soccer player, an ice hockey player, and a skier all use a lateral push-off to stop and/or to change direction of movement.

In this example, the majority of the weight and muscle contraction force is in the ball of the foot with none shown in the heel section. Note that some athletes may executed a lateral push-off with up to half of their weight in the heel section.

For a lateral push-off the weight and muscle contraction force, as represented by the red arrow, traverses down the leg towards the foot. For an athletic movement, the athlete is contracting his or her muscles, which adds up to six times the athlete's body weight to the overall weight and muscle contraction force. Assuming the shoe is firmly planted on the ground (i.e., no roll over or slipping), the weight and muscle contraction force is divided into perpendicular force components as represented by the blue arrows and parallel force components as represented by the yellow arrows in the y direction and orange arrows in the x direction at the foot and into the shoe.

Within the shoe, the perpendicular Z force component traverses through the shoe to the ground. The ground produces the ground reaction force, which is represented by the green arrow, that is equal to and opposite of the perpendicular Z force. In this example, the ground reaction force is not equal to and opposite of the weight and muscle contraction force, but of the perpendicular Z component, which is less than the weight and muscle contraction force. The magnitude of the perpendicular Z component is calculated the cosine of φ times the magnitude of the weight and muscle contraction force. "φ" represents the angle of the weight and muscle contraction force with respect the slopes of the sole in the y direction and in the x direction. In this example, the sole has no medial to lateral slope and has a slight toe to heel slope.

The horizontal y component, as expressed by the yellow arrow in the front view and top view, is parallel to the surface of the sole and to the ground. If the shoe does not include a mechanism to apply a force that is equal and opposite of the horizontal y component, the foot will move laterally within the shoe, which increases the angle and reduces the ground reaction force.

The horizontal x component, as expressed by the orange arrow in the side view and top view, is parallel to the surface of the sole and at a slight angle to the ground. If the shoe does not include a mechanism to apply a force that is equal and opposite of the horizontal x component, the foot will move linearly within the shoe, which increases the angle and further reduces the ground reaction force.

The force detection system 20 is operable to detect the magnitude and angles of the ground reaction force, the perpendicular Z force component, the horizontal Y force component, and the horizontal X force component. From these data points, the weight and muscle contraction force can be calculated.

FIGS. 10A-10C are front, side, and top views of an example of force applied by a foot to the force detection system 20 when a wearer is running and the foot is impacting the ground. In an efficient sprint, the first contact of the landing foot should almost be directly underneath the athlete. The athlete pulls his or her leg back after initial contact of the foot until the foot is released from the ground. How the foot engages the ground and the duration of ground impact effect the efficiency of running.

In this example, the weight and muscle contraction force is shown for an inefficient runner since the contact point with the ground is in front of the body as evidenced by the angle of the force. Further, the example illustrates the weight and muscle contraction force only has an angle in the linear direction and not one in the lateral to medial direction.

The weight and muscle contraction force, as represented by the red arrow, traverses down the leg towards the foot. For a stride impact when running, the athlete is contracting his or her muscles and landing on the ground, which adds up to six times the athlete's body weight to the overall weight and muscle contraction force. Assuming the shoe is firmly planted on the ground (i.e., no roll over or slipping), the weight and muscle contraction force is divided into perpendicular force components as represented by the blue arrows and parallel X force components as represented by the orange arrow in the x direction at the foot and into the shoe.

Within the shoe, the perpendicular Z force component traverses through the shoe to the ground. The ground produces the ground reaction force, which is represented by the green arrow, that is equal to and opposite of the perpendicular Z force. In this example, the ground reaction force is not equal to and opposite of the weight and muscle contraction force, but of the perpendicular Z component, which is less than the weight and muscle contraction force. The magnitude of the perpendicular Z component is calculated the cosine of φ times the magnitude of the weight and muscle contraction force. "φ" represents the angle of the weight and muscle contraction force with respect the slopes of the sole in the x direction. In this example, the sole has no medial to lateral slope and has a slight toe to heel slope.

The horizontal x component, as expressed by the orange arrow in the side view and top view, is parallel to the surface of the sole and at a slight angle to the ground. If the shoe does not include a mechanism to apply a force that is equal and opposite of the horizontal x component, the foot will move linearly within the shoe, which increases the angle and further reduces the ground reaction force.

The force detection system 20 is operable to detect the magnitude and angles of the ground reaction force, the perpendicular Z force component, the horizontal Y force component (if any), and the horizontal X force component. From these data points, the weight and muscle contraction force can be calculated.

FIGS. 11A-11F are schematic block diagrams of another example of forces applied by a foot to the force detection system when a person is running. In the examples of FIGS. 11A through 11F, the relationship between the weight and muscle contraction force, the z force component, and the x force component vary based on where the foot to ground contact is for a stride.

In FIG. 11A, the foot is making initial contact with the ground for a given stride. This is similar to the foot-ground connection discussed with reference to FIGS. 10A-10C. In the remaining figures, the foot-ground contact varies as the runner executes the stride. Within each figure, the relationship between weight and muscle contraction force, the Z force component, and the X force component varies.

With the high sampling rate of the force detection system 20 (e.g., 5 KHz or more), dozens to hundreds of samples are obtained for a single foot strike. This provides a level of granularity to better understand how the foot engages with the ground during a running. It further enables identifying efficiencies and inefficiencies in running. With inefficiencies identified, corrective measures can be determined to improve a runner's form and/or running efficiency.

Figure 12:
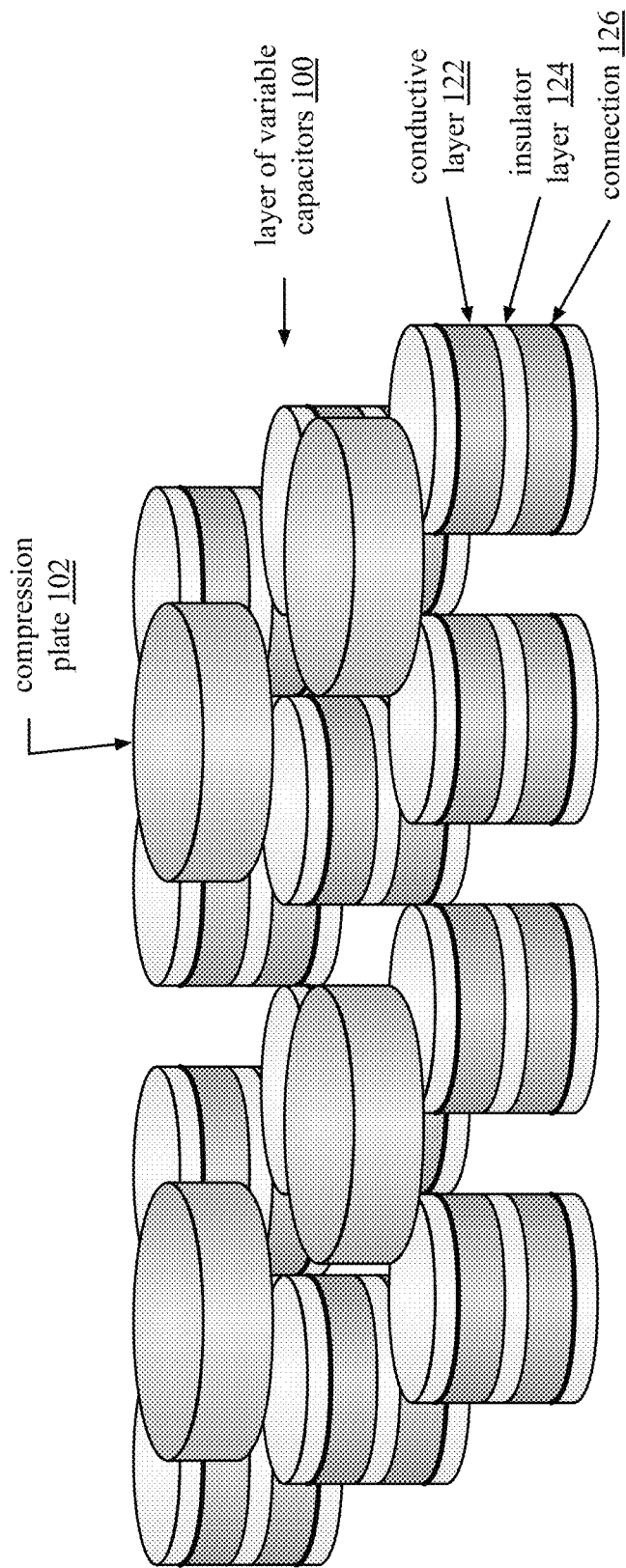
FIG. 12 is a schematic block diagram of another embodiment of a layer of variable capacitors and a layer of compression plates of a force detection system.

FIG. 12 is a schematic block diagram of another embodiment of a layer of variable capacitors and a layer of compression plates of a force detection system 20. In this example, the compression plates 102 are represented by green discs. A variable capacitor includes one or more conductive layers, two or more insulating layers, and two connections (i.e., capacitor plates). In this example, the insulating layers are represented as yellow disc shapes, the conductive layers are represented as blue disc shapes, and the connectors are represented as black ring-like, or plate-like, shapes.

The compression plates 102 may be comprised of one or more materials to form a rigid structure. For example, the compression plates are comprised of plastic. As another example, the compression plates are comprised of fiberglass. As another example, the compression plates are comprised of carbon fiber. As yet another example, the compression plates are comprised on a metal.

The dimensions of a compression plate will vary depending on the material, or materials, it is comprised of, the size of the variable capacitors, the distance between the variable capacitors, the number of variable capacitors it overlaps, and a maximum force load. For example, the thickness of a compression plate, which should be in the range of a few microns to a few millimeters, is based on the rigidity of the material, the maximum force load, and a flexion range of the compression plate under a force load. Ideally, the flexion of the compression plate should be negligible with respect to the compression range of the variable capacitors. In the ideal case, the flexion of the compression plate can be ignored when calculating the applied force; the calculations will be based on the compression of the variable capacitors. If the flexion of the compression plate is not negligible, the flexion should be factored into the calculations of the applied force, which makes the calculations more complex than in the ideal case.

The perimeter dimension of a compression plate should be comparable to the perimeter of the variable capacitors the compression plate overlaps. For example, a compression plate, which overlaps three variable capacitors having a circular shape from a top perspective, has a circular shape with a diameter in the range of 1.25 times to 2.25 times the diameter of a variable capacitor. As another example, a compression plate, which overlaps three variable capacitors having a circular shape from a top perspective, has a rounded equilateral triangular shape with each of a base dimension and of a height dimension of 1.25 times to 2.25 times the diameter of a variable capacitor.

For a variable capacitor, the number of conductive layers and the number of insulator layers depend on the desired capacitance range, desired thickness of the layer of capacitors, and the materials of composition. A variable capacitor may be fabricated in a variety of ways. For example, a variable capacitor is fabricated from a Z electrometric conductor (ZEC). In another example, a variable capacitor is fabricated from one or more dielectric elastomers. The capacitance value and the range of capacitance values varies based on the materials used and their compression ratio. The materials include acrylates, silicones, polyurethanes (PU), rubbers, latex rubbers, acrylonitrile butadiene rubbers, olefinic, polymer foams, fluorinated and styrenic copolymers, etc.

The equation for a parallel capacitor is:

$$C = \epsilon_0 \epsilon_r \frac{A}{d}$$

Where C is the capacitance, $\epsilon_0$ is the permittivity of a vacuum, $\epsilon_r$ is the relative permittivity, A is the area of the plates, and d is the distance between the plates. The relative permittivity can range from 1 to 10 or more.

In an example, a variable capacitor is formed with a compressible dielectric material layer between two conductive plates that are separated by a distance from each other. The variable capacitor may further include two non-compressive insulting layers. The dielectric material has a relative permittivity of 2.8 and is compresses by 50% from no compression to fully compressed, which occurs at 825 kg (kilograms) of force.

For this example, the two conductive plates have an area of 71.26 millimeters squared (mm²) (i.e., ⅜ inch diameter) and the uncompressed distance between the plates of 0.79 mm (i.e., 1/32 of an inch). In the uncompressed state, the variable capacitor has a capacitance value of 2.25 pico Farads (pF). When the distance between the plates compresses by 50%, the variable capacitor has a capacitance of 4.45 pF. To increase the capacitance, the variable capacitor includes 4 conductive, or dielectric layers, separated by insulating layer and are coupled in parallel to provide a compressed capacitance of 8.9 pF and a compressed capacitance of 17.8 pF. With a four conductive layer variable capacitance, it's total thickness would be about 3.5 to 4.3 mm thick; less than the thickness of a conventional insole.

For a weight sensing range of 0 kg to 825 kg, the variable capacitor will correspondingly range from no compression to fully compressed. The variable capacitor's capacitance value to compress level curve is factored into the determination of a weight force causing a current compression of the capacitor. If the capacitance value to compress level is fairly linear, then the capacitance value for a particular sample can be multiplied by a constant to obtain a weight force value. If the capacitance value to compress level is not linear, then a non-linear equation will be applied to the capacitance value to obtain a corresponding weight force value.

For this example, assume that the desired granulating for weight force changes is 0.5 kg, then, for a range of 0 to 825 kg, there are 1650 different values of capacitances that need to be measured. As such, a capacitance difference of 0.005 pF represents a 0.5 kg difference.

Continuing with the example and with respect to the drive sense circuit, a 50 mV (milli volt) sinusoidal signal having a frequency of 100 kHz is used as the reference signal, offset by the DC component. The impedance of a capacitor is expressed as:

$$z = \frac{1}{2\pi f C}$$

Where z is the impedance, f is the frequency of the reference signal, and C is the capacitance value. For the uncompressed capacitance value of 8.9 pF, the impedance is 179 K Ohms. Since I=V/Z, the current supplied by the drive sense circuit is 276 nA (nano Amps), yielding a power of 13.9 nW (nano Watts).

To sense a 0.5 kg change in the weight force, the drive sense circuit needs to detect a 0.0054 pF capacitance change, which, for the 50 mV reference signals, corresponds to a current change of 169 nA (e.g., $1.69*10^{-10}$ amps). The assignee's drive sense circuit has a signal-to-noise ration of at least 120 dB, which means in can detect a change at a ratio of 1 to $1*10^{12}$. As such, the assignee's drive sense circuit is more than sensitive enough to detect a 169 nA change.

With a 120 dB or more of signal to noise ratio, there is ample room to adjust capacitor size and shape, the magnitude of the reference signal, the number of capacitors in the force detection system, and so on. For example, the shape of the capacitor from a top perspective is a four, five, six, seven, eight, or more, sided polygon. The compression plate would have a corresponding shape from the top perspective. Examples of how the compression plate effects the capacitance values of the capacitors it compresses will be discussed with reference to one or more subsequent figures.

Figure 13:
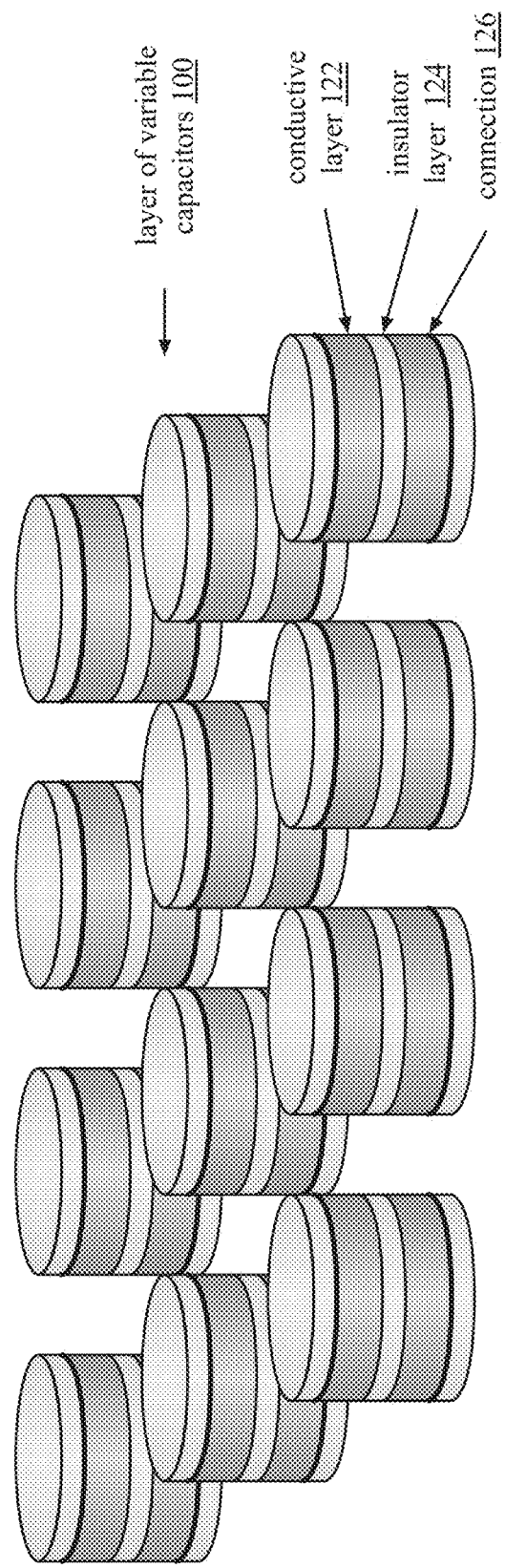
FIG. 13 is a schematic block diagram of another embodiment of a layer of variable capacitors FIG. 12 without a layer of compression plates of a force detection system.

FIG. 13 is a schematic block diagram of another embodiment of a layer of variable capacitors of FIG. 12 without a layer of compression plates. Within an area of the force detection system, a group of variable capacitors are arranged as rows and columns. The positioning of a variable capacitor in a group and variable capacitors and within the force detection system allows the forces it senses to be equated to a portion of a foot of a wearer.

FIGS. 14A-14C are schematic block diagrams of an example of a layer of variable capacitors 100 and a layer of compression plates 102 of a force detection system. FIG. 14A illustrates a top view of the layer of compression plates 102 only, which are represented by green circles. FIG. 14B illustrates a top view of the layer of variable capacitors 100 only, which are represented by blue circles. FIG. 14C illustrates a top view of the layer of compression plates 102 (i.e., partially translucent green circles) position over the layer of variable capacitors 100 (i.e., the blue circles). In this example, one compression plate overlaps three variable capacitors. When a force is applied to the compression plate, it transfers the force to the three variable capacitors. The force applied to each of the variable capacitors is measured and used to determine the magnitude and direction of the force on the compression plate.

FIGS. 15A-15E are schematic block diagrams of an example of a layer of variable capacitors 100 and a layer of compression plates 102 of a force detection system with and without compression of the capacitors. FIG. 15A illustrates the variable capacitors 100-1 in a non-compress state (i.e., no force is being applied to the compression plate 102-1) and FIG. 15B illustrates the variable capacitors 100-1 in a fully compressed state (i.e., maximum force is being applied to the compression plate 102-1).

The variable capacitors 100-1, with the blue conductive layers and the yellow insulating layers, are held in place by a capacitor (cap) holding structure 134. The cap holding structure 134 is comprised of a flexible material that allows the capacitors to expanding horizontally and they are compressed vertically while staying in place. For example, the cap holding structure 134 is comprised of one or more of rubber, silicon, EVA, PEVA, foam, a gel, etc.

The compression plates 102-1 (e.g., the green discs) are held in place by a plate holding structure 130. The plate holding structure 130 is comprised of a flexible material that allows for each compression plate to move freely and independently. The plate holding structure 130 is comprised of one or more of rubber, silicon, EVA, PEVA, foam, a gel, etc.

The variable capacitors 100-1, the cap holding structure 134, the compression plates 102-1, and the plate holding structure 130 are housed within a perimeter support structure 132. The perimeter support structure 132 is comprised of a rigid material and may house one or more sets of a compression plate and associated variable capacitors. As for the rigid material, it is one or more of a hard rubber, plastic, carbon fiber, etc.

In an example as shown in FIG. 15C, the perimeter support structure 132 houses one set of a compression plate and associated variable capacitors. In this example, the force detection system 20 would include a plurality of perimeter support structures 132. In another example as shown in FIG. 15D, the perimeter support structure 132 houses two sets of a compression plate and associated variable capacitors. In yet another example as shown in FIG. 15E, the perimeter support structure 132 houses three sets of a compression plate and associated variable capacitors.

Figure 16B:
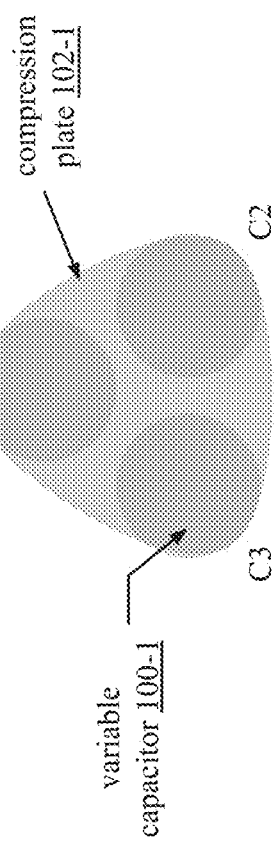
FIGS. 16A-16C are schematic block diagrams of examples of a geometric and electrical relationship between variable capacitors of a second layer and a compression plate of a first layer within a force detection system.
Figure 16A:
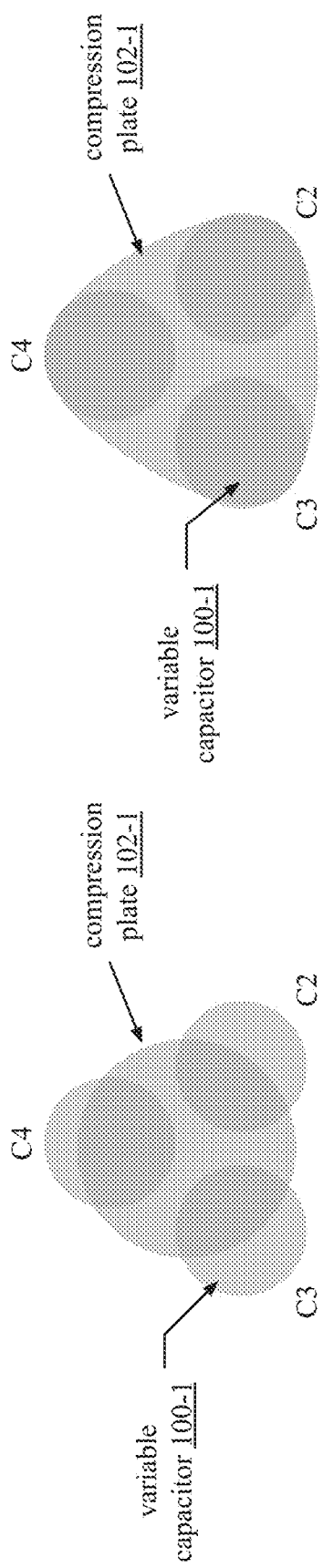
Figure 16C:
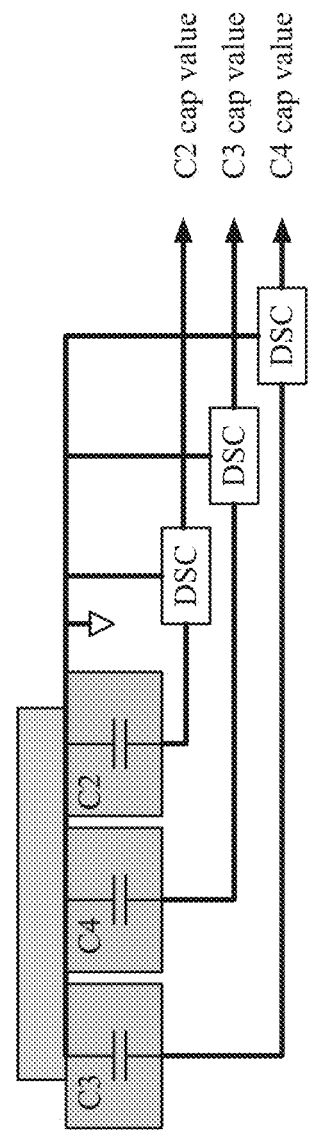

FIGS. 16A-16C are schematic block diagrams of examples of a geometric and electrical relationship between variable capacitors of a second layer and a compression plate of a first layer within a force detection system. FIG. 16A illustrates from a top view, a circular compression plate 102-1 that partially overlaps three variable capacitors 100-1 (e.g., C2, C3, and C4). FIG. 16B illustrates from a top view, a triangular compression plate 102-1 that substantially overlaps three variable capacitors 100-1 (e.g., C2, C3, and C4).

FIG. 16C illustrates a schematic block diagram of the three variable capacitors of FIGS. 16A and 16B coupled to respective drive sense circuits (DSC). One plate of each of the capacitors C2-C4 is coupled to a reference ground and the other plate is coupled to a respective DSC. The output of each drive sense circuit is a digital value, at a desired sampling rate, of the capacitance of the respective capacitor. For example, one of the DSCs outputs a digital value of the capacitance value for C2; another of the DSCs outputs a digital value of the capacitance value for C3; and third one of the DSCs outputs a digital value of the capacitance value for C4.

FIG. 17 is a schematic block diagram of an example of a graph that depicts capacitance variance with respect to compression of a of variable capacitor. In this example, as force is applied to a variable capacitor, the capacitance increases. When no force is applied, the capacitance is at a minimum capacitance value. The capacitance value increases with force until it reaches a maximum value. At this point, the variable capacitor is fully compressed and a further increase in force will not increase the capacitance.

For an ideal variable capacitor, its capacitance changes linearly with the force applied. For many variable capacitors, there is at least a range of capacitance values where the change in force is substantially linear. As such, the applied force can be accurately determined based on the measured capacitance for the range of capacitances.

In equation form, $C_0 = C_{min} + \Delta x * \Delta C$, where $C_0$ is the capacitance of the variable capacitor; $C_{min}$ is the capacitance of the variable capacitor with no compression, $\Delta x$ is the percentage of displacement with respect to a maximum displacement (i.e., compression), where $\Delta x = x_0/x_{max}$, and $\Delta C$ is the difference between $C_{max}$ and $C_{min}$. Also, the force to compress the variable capacitor is expressed as $F = k * x_0$, where F is the force, k is the compression factor of the variable capacitor, and x is the displacement. The compression factor "k" is a constant that reflects the stiffness of the variable capacitor (i.e., its resistance to compression).

Through substitution:

$$F = \frac{k * x_{max}}{\Delta C} * (C_0 - C_{min})$$

In this form, the applied force is readily calculated from a measured capacitance ($C_0$) of the variable capacitor on a per sampling rate basis. The forces measured by multiple variable capacitors can be used to determine the magnitude and direction of the force applied to a corresponding compression plate. Note that non-linearities between force and capacitance value can be factored into the above equation. In such non-linear applications, k is not a constant but a variable that represents the shape of the curve.

FIGS. 18A-18C are schematic block diagrams of examples of an impact force applied to a cell of a force detection system (e.g., a compression plate and three variable capacitors). In this example, the variable capacitors C2-C4 are substantially identical in terms of size, shape, compression factor (k), minimum capacitance, maximum displacement, and maximum capacitance. As such, when an equal force is applied to the variable capacitors, they each produce a capacitance value that are substantially identical (i.e., negligible differences).

FIGS. 18A and 18B illustrate a top view and a side view of a force being applied to the cell. The force is normal to the compression plate 102-1, which transfers the force equally among the variable capacitors C2-C4, as shown in FIG. 18C. FIG. 18C is also applicable for a cell embodiment that does not include a compression plate; it includes, for example the three variable capacitors provided that the wearer's foot makes contact with the variable capacitors.

With the force equally applied to the capacitors, they each have the same capacitance change. The force applied to each capacitor is then readily calculatable. The magnitude and direction of the applied force is then calculated from the forces detected by the capacitors. An example of the calculation will be discussed with reference to one or more of FIGS. 19A-24B.

FIGS. 18D-18F are schematic block diagrams of examples of an impact force applied to a cell of a force detection system (e.g., a first layer capacitor and three second layer capacitors). In this example, the top layer is another variable capacitor. In this instance, the magnitude of the applied force is calculable from the capacitance change of the first layer capacitor 108-1 and the direction is calculable from the capacitance change of the second layer capacitors 100.

Figure 19B:
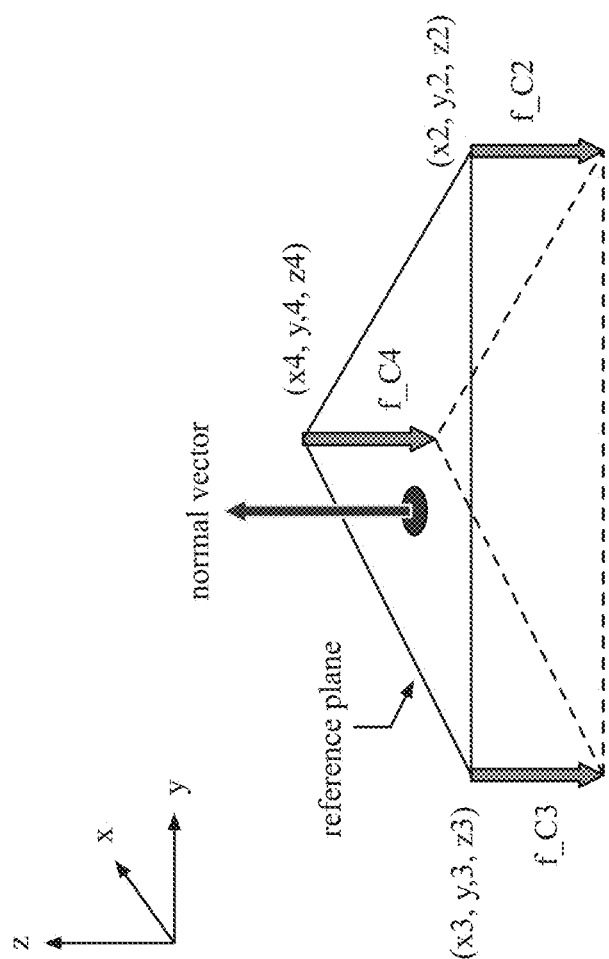
FIGS. 19A-19B are schematic block diagrams of an example of determining a normal vector of a reference plane of a cell of a force detection system in response to an impact force.
Figure 19A:
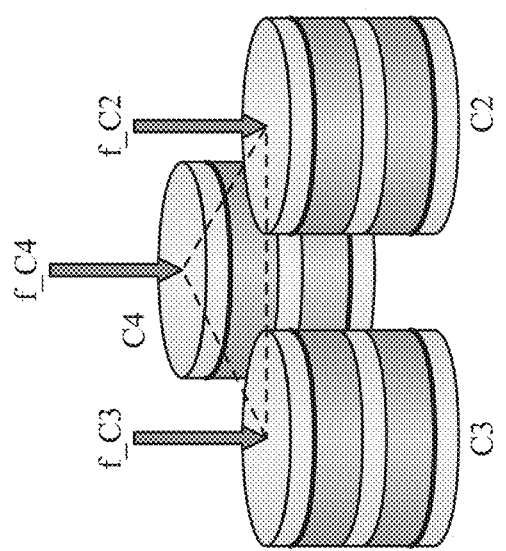

FIGS. 19A-19B are schematic block diagrams of an example of determining a normal vector of a reference plane of a cell of a force detection system in response to an impact force, wherein the normal vector corresponds to the impact force yielding x, y, and z direction force data. From the examples of FIGS. 18A-18F, the second layer of variable capacitors (C2-C4) yield a corresponding force vector f_C2 through f_C4 that are equal as shown in FIG. 19A.

The force vectors are used to create a reference plane as shown in FIG. 19B, which is then used to determine a normal vector that represents the magnitude and direction of the applied force. To calculate the reference plane, the force vectors f_C2 through f_C4 are mapped to a coordinate system (e.g., a Cartesian system or a polar system, this example is based on a Cartesian coordinate system). In this example, the x-y plane of the Cartesian coordinate system is parallel to the bottom of a shoe and the z direction is perpendicular to the bottom of the shoe.

As shown, f_C2 is mapped to a coordinate point of x2, y2, z2; f_C3 is mapped to a coordinate point of x3, y3, z3; and f_C4 is mapped to a coordinate point of x4, y4, z4. The three coordinate points are used to determine the reference plane. For example, the equation of a plane of $D=Ax+By+Cz$. Coefficients A, B, and C are determined such that each coordinate point (e.g., coordinate points of C2, C3, and C4) on the plane satisfies this equation.

As a specific example, assume that coordinate point C2 is 1, 1, 1; coordinate point C3 is 2, 3, 1; and coordinate point C4 is 4, 2, 1. From these coordinate points, three equations emerge.

1A+1B+1C=D for coordinate point C2;
2A+3B+1C=D for coordinate point C3; and
4A+2B+1C=D for coordinate point C4.

Solving the three equations yields A=0; B=0; and C=1. From the plane equation of D=(1)z, the normal vector of the plane is calculable. For example, equation for the normal vector (n)=Ai+Bj+Ck, where i is the unity vector in the x direction, j is the unity vector in the y direction, and k is the unity vector in the z direction. Thus, for this example the normal vector (n) (i.e., the applied force)=(1)k, which means that the applied force has a magnitude of 1 and a direction that is perpendicular to the x-y plane.

FIGS. 20A-20D are schematic block diagrams of another example of determining a normal vector of a reference plane of a cell of a force detection system. In this example, the applied force on a cell (e.g., a set of variable capacitors and a compression plate) is at angle from the z axis with respect to both the x and y. An example is shown the top view perspective of FIG. 20A. The impact force, as represented by the orange arrow includes an x force component that is represented by the red arrow and a y-force component that is represented by the yellow arrow.

FIG. 20B is a side view from an x-z plane of the cell that depicts it being impacted by the x-force (i.e., the red arrow). The x-force pushes on the compression plate causing it to slant in the direction of the x-force. This causes more compression of capacitor C2 than of capacitor C4, which compresses more that capacitor C3.

FIG. 20C is a side view from a y-z plane of the cell that depicts it being impacted by the y-force (i.e., the yellow arrow). The y-force is more vertical than the x-force, thus it pushes on the compression plate more perpendicularly, which causes a more even distribution of the force among the capacitors. Even so, there is a bit more force applied to capacitor C4 than capacitors C2 and C3. With respect to both FIGS. 20B and 20C, capacitor C2 has the more force applied to it than capacitor C4, which has more forced applied to it than capacitor C3. As such, the capacitance value for C2, will be higher than the value for C4, which will be higher than the value for C3.

FIG. 20D illustrates an example of a reference plane resulting from the impact force (e.g., the orange arrow). For this example, assume that coordinate point C2 is 1, 1, 4; coordinate point C3 is −1, 2, 1; and coordinate point C4 is 1, 2, 3. From these coordinate points, three equations emerge.

1A+1B+4C=D for coordinate point C2;
−1A+2B+1C=D for coordinate point C3; and
1A+2B+3C=D for coordinate point C4.

Solving the three equations yields A=−¼; B=¼; and C=¼. From the plane equation of 1=−(¼)x+(¼)y+(¼)z, the normal vector of the plane is calculable. For example, equation for the normal vector (n)=Ai+Bj+Ck, where i is the unity vector in the x direction, j is the unity vector in the y direction, and k is the unity vector in the z direction. Thus, for this example the normal vector (n) (i.e., the applied force)=−(¼)i+(¼)j+(¼)k. The impact force is equal to and opposite of the normal vector.

FIGS. 21A-21D are schematic block diagrams of another example of determining a normal vector of a reference plane of a cell of a force detection system. In this example, the applied force on a cell (e.g., a set of variable capacitors and a first layer capacitor) is at angle from the z axis with respect to both the x and y. An example is shown the top view perspective of FIG. 21A. The impact force, as represented by the orange arrow includes an x force component that is represented by the red arrow and a y-force component that is represented by the yellow arrow.

FIG. 21B is a side view from an x-z plane of the cell that depicts it being impacted by the x-force (i.e., the red arrow). The x-force pushes on the first layer capacitor 108-1 causing it to slant in the direction of the x-force. This causes more compression of capacitor C3 than of capacitor C4, which compresses more than capacitor C2. With the angle of the x-force, the compression of capacitor C3 is slightly greater than that of capacitor C4.

FIG. 21C is a side view from a y-z plane of the cell that depicts it being impacted by the y-force (i.e., the yellow arrow). The y-force has approximately the same angle as the x-force, thus it pushes on the first layer capacitor in a similar manner. This causes more compression of capacitor C4 than of capacitors C3 and C2. With the angle of the x-force, the compression of capacitors C3 and C2 are comparable.

With respect to both FIGS. 21B and 21C, capacitor C3 has the more force applied to it than capacitor C4, which has more forced applied to it than capacitor C3. As such, the capacitance value for C2, will be higher than the value for C4, which will be higher than the value for C3.

FIG. 21D illustrates an example of a reference plane resulting from the impact force (e.g., the orange arrow) through the first layer capacitor to the second layer of capacitors. The capacitance change of the first layer capacitor in combination with the second layer capacitors determines the magnitude and direction of the impact force. For this example, assume that coordinate point C2 is 2, 1, 1; coordinate point C3 is 0, 0, 5; and coordinate point C4 is 1, −1, 4. From these coordinate points, three equations emerge.

2A+1B+1C=D for coordinate point C2;
5C=D for coordinate point C3; and
1A+(−1)B+4C=D for coordinate point C4.

Solving the three equations yields A=⅓; B=2/15; and C=⅕. From the plane equation of 1=(⅓)x+(2/15)y+(⅕)z, the normal vector of the plane is calculable. For example, equation for the normal vector (n)=Ai+Bj+Ck, where i is the unity vector in the x direction, j is the unity vector in the y direction, and k is the unity vector in the z direction. Thus, for this example the normal vector (n) (i.e., the applied force)=(⅓)i+(2/15)j+(⅕)k. The direction of the impact force is opposite of the normal vector and its magnitude is the sum of the magnitude of the normal vector and the force determined from the compression of the top layer capacitor.

FIGS. 22A-22C are schematic block diagrams of an example of determining a plurality of normal vectors of a plurality of reference planes of a plurality of cells of a force detection system in response to an impact force. FIG. 22A illustrates twelve second layer variable capacitors (C1-C12) arranged in a pattern to form 12 triangles, which represent independent reference planes. In this example, the impact force is shown as an orange arrow that applies a force to the variable capacitors at different levels creating a force pattern as shown in FIG. 22B.

For each reference plane a normal force is determined as previously discussed. In an example, the magnitude and direction of the impact force is determined from resulting normal vectors. As a specific example, the normal vectors are added together to produce a final normal vector. The impact force is equal to and opposite of the final normal vector. In another example, the twelve normal vectors are used to determine twelve impact force components to produce an impact force gradient.

Figure 23:
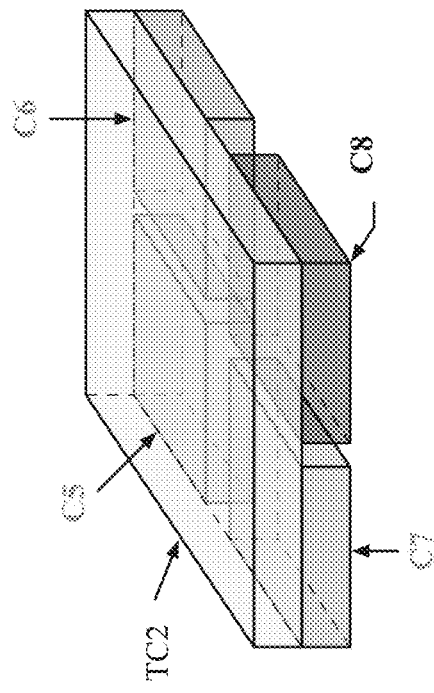
FIG. 23 is a schematic block diagram of an example of two cells, each having a top layer capacitor (TC) (light green) and a four lower layer capacitors (green, blue, red, black)

FIG. 23 is a schematic block diagram of an example of two cells for a force detection system. Each includes a top layer capacitor (TC) (light green) and four lower layer capacitors (green, blue, red, black). In the first cell, the top layer capacitor TC1 substantially overlaps the four lower layer capacitors (C1-C4), where C1 is the blue shaded capacitor, C2 is the red shaded capacitor, C3 is the green shaded capacitor, and C4 is the black shaded capacitor. In the second cell, the top layer capacitor TC2 substantially overlaps the four lower layer capacitors (C5-C8), where C5 is the blue shaded capacitor, C6 is the red shaded capacitor, C7 is the green shaded capacitor, and C8 is the black shaded capacitor. There is a gap of a few microns to a millimeter or more between the lower layer capacitors to allow for horizontal expansion from a vertical compression.

Figure 24A:
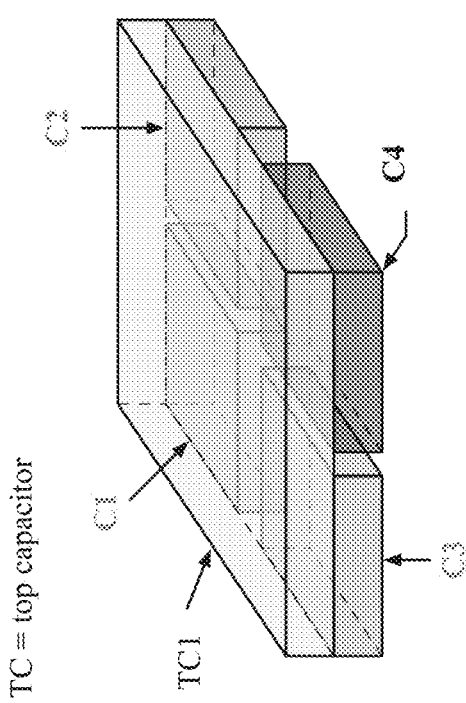
FIGS. 24A-24B are schematic block diagrams of examples of impact forces impacting a cell of FIG. 23.
Figure 24B:
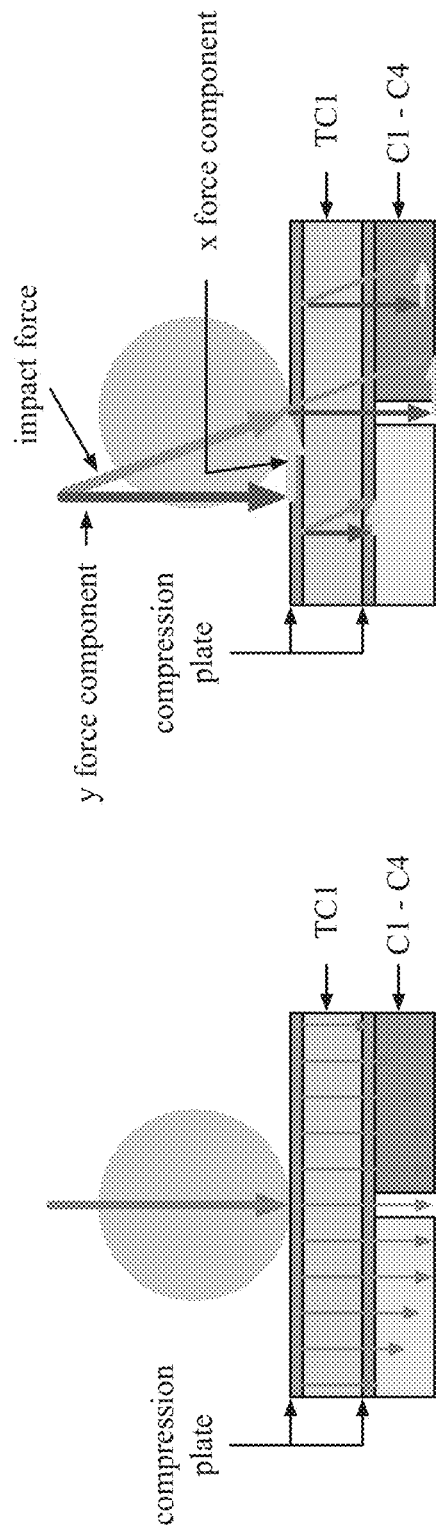

FIGS. 24A-24B are schematic block diagrams of examples of impact forces impacting a cell of FIG. 23. FIG. 24A is a front view of the first cell of FIG. 23. The cell is receiving a perpendicular force via an object. In this example, the object has a rounded outer shape resembling a cross section of a toe.

The top layer capacitor TCI is sandwiched between two compression plates. The first compression plate receives the impact force applied by the object. The impact area is small due to the shape of the object. The first compression plate transfers the impact force to the top layer capacitor TC1 in a three-dimension parabolic pattern. The force applied to the top layer capacitor TC1 is the largest and decreases in a parabolic manner the further away from the impact force area it gets. While this produces a nonlinear force gradient applied to the top layer capacitor TC1, the change is change in capacitance is measured as a single value to represent an average, or median, force.

The top layer capacitor TC1, as it is compressed, applies the parabolic force gradient to the second compression plate. The second compression plate transfers the parabolic force gradient to the lower layer capacitors (C1-C4). Each of the lower layer capacitors are compressed based on the force it receives. The capacitance change is used to determine the individual forces received by the lower layer capacitors. The combination of the capacitance changes to TC1 and to C1-C4 are used to determine the magnitude and direction of the impact force.

FIG. 24B is another front view of the first cell of FIG. 23. In this example, the top compression plate is receiving an impact force (e.g., the orange arrow) at an angle. As such, in this plane of view, the impact force includes an x force component (e.g., the yellow arrow) and a y force component (e.g., the red arrow). The impact force, and its x and y components, traverse through the cell. Due to the angle of the impact force, more force is transferred to C4 (e.g., the black shaded capacitor) than to C3 (the green shaded capacitor). As such, C4 will have a greater capacitance change than C3. The combination of capacitance changes of TC1 and C1 through C4 are used to calculate the magnitude and direction of the impact force as previously discussed.

As an alternative embodiment, a cell includes one compression plate and the four lower capacitors, omitting the top compression plate and the top layer capacitor. In another alterative embodiment, a cell includes the top layer capacitor and the four lower layer capacitors, omitting the compression plates.

Figure 25:
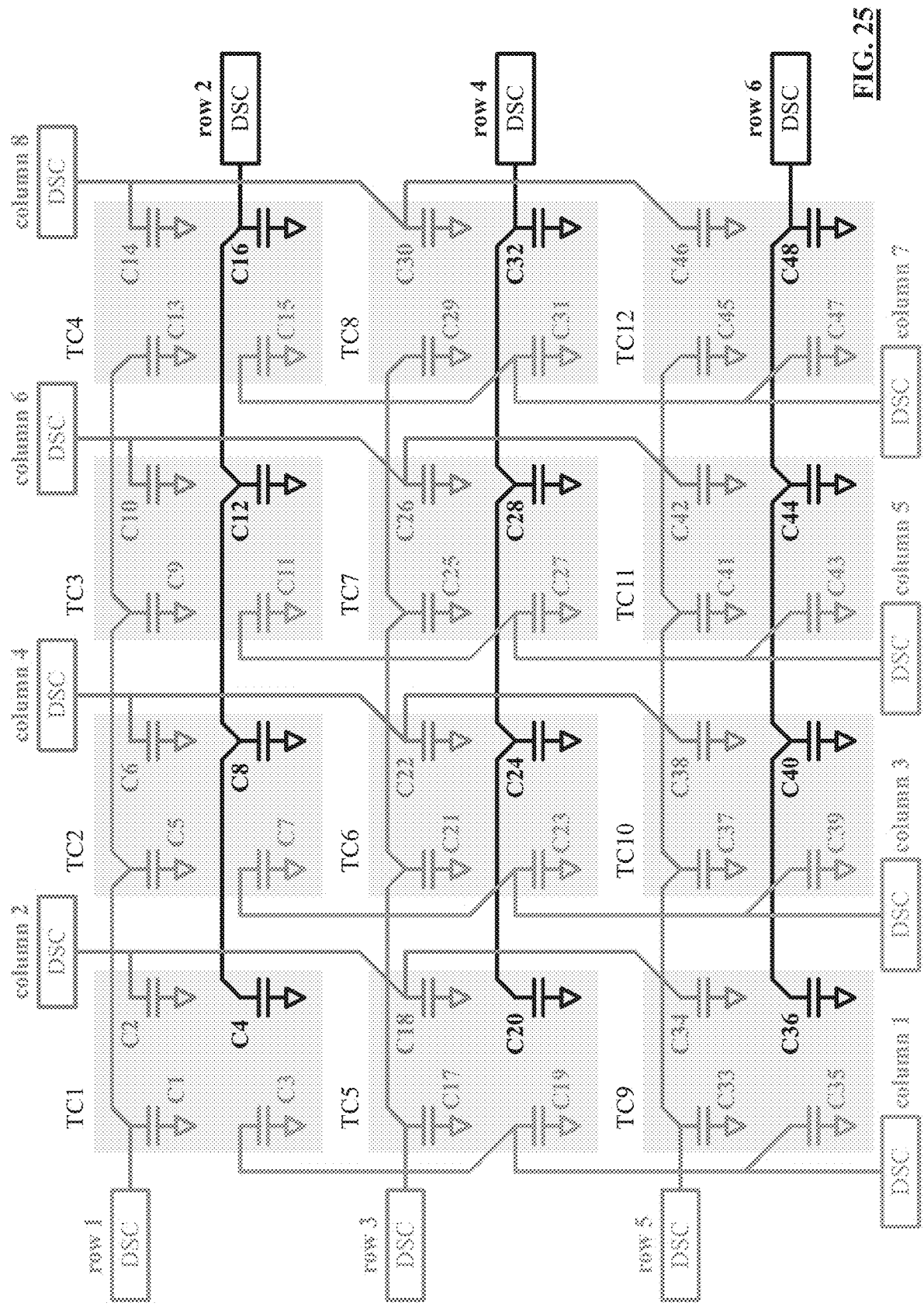
FIG. 25 is a schematic block diagram of an example of a plurality of cells.

FIG. 25 is a schematic block diagram of an example of a plurality of cells. Each cell includes three or more lower-level capacitors. Four shown in this example: C1=blue, C2=red, C3=green, and C4=black). The cell may further includes a top layer capacitor and/or one or more compression plates. In this example, the cell includes a top layer capacitor and two compression plates as shown in FIGS. 24A and 24B.

The cells are arranged in rows and columns. In this example, there are three rows and four columns of cells. From a capacitor perspective, there are six rows of capacitors and eight columns of capacitors. Each row and each column of capacitors is coupled to a drive sense circuit (DSC). For example, each blue capacitor of a cell in a row of cells (e.g., C1, C5, C9, C13) is coupled to a blue outlined drive sense circuit (DCS). The blue capacitors of the cells comprise rows 1, 3, and 5.

As another example, each black capacitor of a cell in a row of cells (e.g., C4, C8, C12, C16) is coupled to a block outlined drive sense circuit (DCS). The black capacitors of the cells comprise rows 2, 4, and 6.

As yet another example, each red capacitor of a cell in a column of cells (e.g., C2, C18, C34) is coupled to a red outlined drive sense circuit (DCS). The red capacitors of the cells comprise columns 2, 4, 6, and 8.

As a further example, each green capacitor of a cell in a column of cells (e.g., C3, C19, C35) is coupled to a green outlined drive sense circuit (DCS). The green capacitors of the cells comprise columns 1, 3, 5, and 7. In this example, there are forty-eight capacitors (c1-C48) and only fourteen drive sense circuits.

In an example, the row 1 DSC circuit drives and senses the blue capacitors in the first row of cells (C1, C5, C9, and C13). The blue capacitors are coupled in parallel, thus their collective capacitance with no compression is four times the minimum capacitance (assuming the capacitors are similar). If one or more of the capacitors is compressed, the collective capacitance of row 1 changes and is detected by the row 1 DSC. The row 1 DSC, however, cannot detect which of the four capacitors is experience the compression.

The same applies for each of the other row DSCs. For instance, the row 2 DSC drives and senses the collective capacitance of the black capacitors C4, C8, C12, and C16; the row 3 DSC drives and senses the collective capacitance of the blue capacitors C17, C21, C25, and C29; the row 4 DSC drives and senses the collective capacitance of the black capacitors C20, C24, C28, and C32; the row 5 DSC drives and senses the collective capacitance of the blue capacitors C33, C37, C41, and C45; and the row 6 DSC drives and senses the collective capacitance of the black capacitors C36, C40, C44, and C48.

Continuing with the example, the column 1 DSC circuit drives and senses the green capacitors in the first column of cells (C3, C19, and C35). The green capacitors are coupled in parallel, thus their collective capacitance with no compression is three times the minimum capacitance (assuming the capacitors are similar). If one or more of the capacitors is compressed, the collective capacitance of column 1 changes and is detected by the column 1 DSC. The column 1 DSC, however, cannot detect which of the three capacitors is experience the compression.

The same applies for each of the other column DSCs. For instance, the column 2 DSC drives and senses the collective capacitance of the red capacitors C2, C18, and C34; the column 3 DSC drives and senses the collective capacitance of the green capacitors C7, C23, and C39; the column 4 DSC drives and senses the collective capacitance of the red capacitors C6, C22, and C38; the column 5 DSC drives and senses the collective capacitance of the green capacitors C11, C27, and C43; the column 6 DSC drives and senses the collective capacitance of the red capacitors C10, C26, and C42; the column 7 DSC drives and senses the collective capacitance of the green capacitors C15, C31, and C47; and the column 8 DSC drives and senses the collective capacitance of the red capacitors C14, C30, and C46.

To identify a particular cell experiencing compression, capacitance changes for at least one of its rows and at least one of its columns are detected. For example, when row 1 DSC detects a capacitance change and column 4 DSC circuit detects a capacitance change, then it is determined that the cell labeled TC2 is experience compression. In particular, blue capacitor C5 and red capacitor C6 are being compressed. If row 1 and column 4 are the only capacitor row and capacitor column to experience a capacitance change, then the row capacitance change is attributable to capacitor C5 and the column capacitance change is attributable to capacitor C6.

If, however, row 1 and column 4 are not the only capacitor row and capacitor column to experience a capacitance change, then further processing is required to determine the capacitance change of each capacitor experiencing compression. FIGS. 26A-26D are schematic block diagrams of an example of such further processing.

Figure 26A:
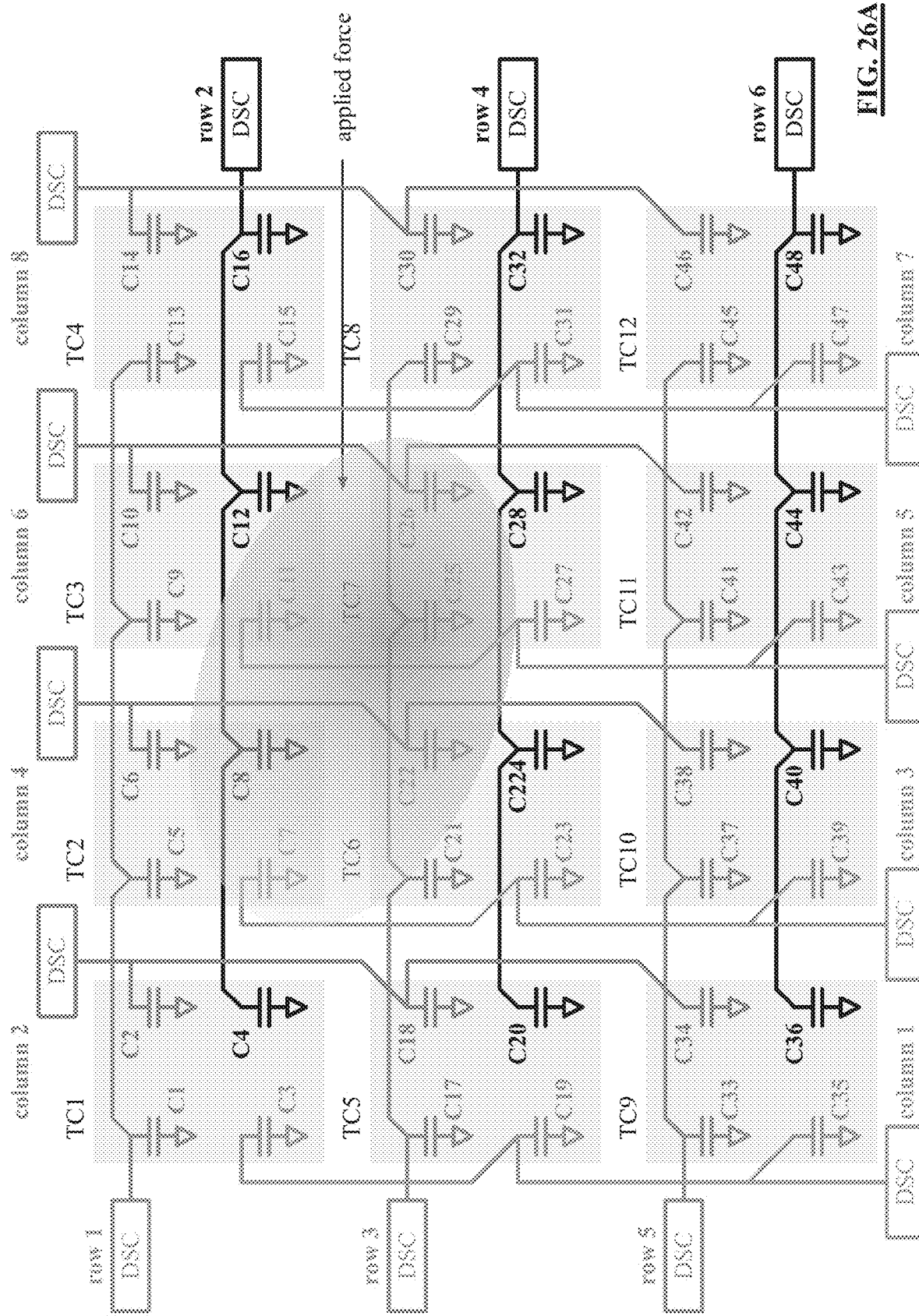

FIG. 26A illustrates an applied force overlapping cells TC2, TC3, TC6, and TC7. The applied force has a magnitude gradient, where more force is represented by the color red and less force by the color yellow. In an example, the shape of the applied force corresponds to the ball of foot or a big toe.

Figure 26B:
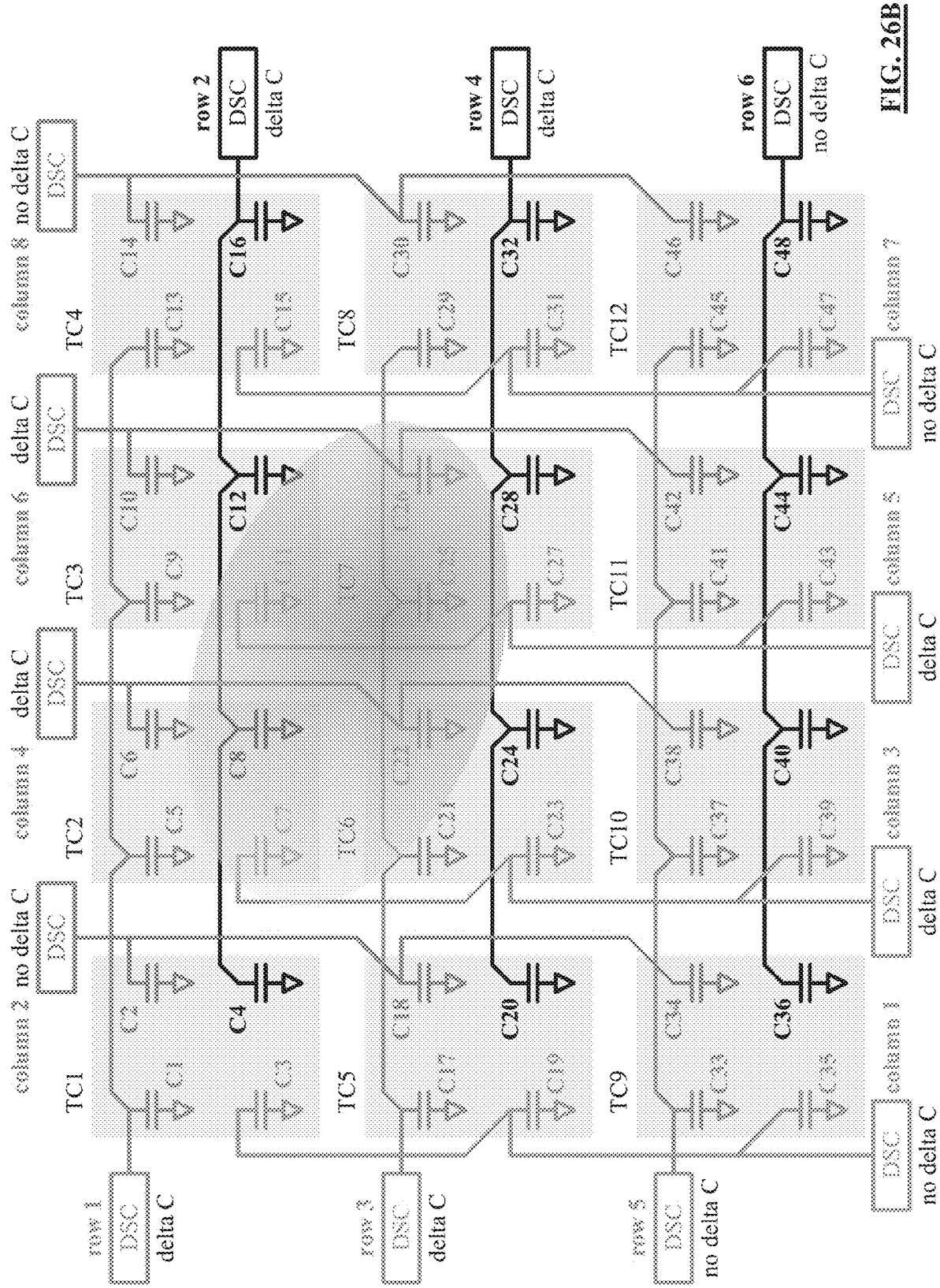

FIG. 26B illustrates which of the drive sense circuits (DSC) detects a capacitance as a result of the applied force. In this example, a capacitance change is represented as "delta C" and no capacitance change is represented as "no delta C". As shown, rows 1-4 and column 3-6 are experience a capacitance change and rows 5-8, columns 1, 2, 7, and 8 do not experience a capacitance change.

Figure 26C:
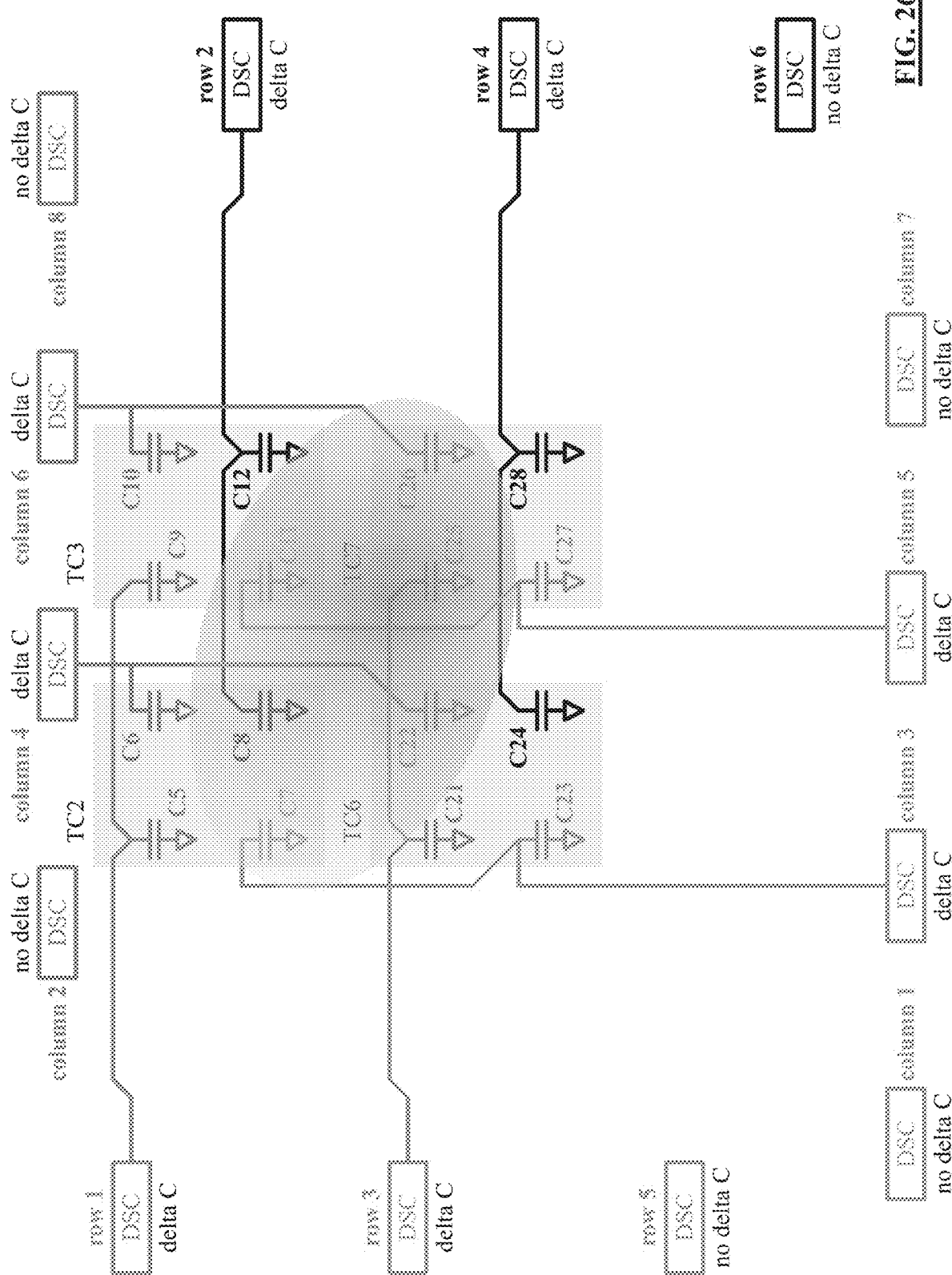

FIG. 26C illustrates the effected DSCs and capacitors of FIG. 26B. In this example, only capacitors C5 and C9 contribute to the capacitor change of row 1; only capacitors C8 and C12 contribute to the capacitor change of row 2; only capacitors C21 and C25 contribute to the capacitor change of row 3; and only capacitors C24 and C28 contribute to the capacitor change of row 4.

Also in this example, only capacitors C7 and C23 contribute to the capacitor change of column 3; only capacitors C6 and C22 contribute to the capacitor change of column 4; only capacitors C11 and C27 contribute to the capacitor change of column 5; and only capacitors C10 and C26 contribute to the capacitor change of column 7. The next processing task for each effected row and column is to determine the amount of change for each of the two effected capacitors. As an example, the next processing task is to determine the capacitance change of each of capacitors C5 and C9 for row 1.

As part of the next processing step, the capacitance changes on the row are ranked from lowest to highest and the capacitance changes on the columns are ranked from lowest to highest. For this example, row 3 has the highest capacitance change, then row 2, then row 4, and row 1 had the lowest capacitance change. For the columns, column 5 had the highest capacitance change, then column 4, then column 6, and column 3 had the lowest capacitance change.

FIG. 26D illustrates the row and column rankings for capacitive changes. The row and column rankings are used to establish a row-column intersect ranking. In this example, the row ranking is multiplied by the column ranking to establish a row-column intersect score. The lower the row-column intersect score, the higher the capacitance change, which equates to more applied force. In this example, the approximate center of the applied force is at the intersection row 3 and column 5 since it has the lowest row-column intersect score.

The row-column intersect scores are then processed to determine a cell score. For example, the score for cell TC2 is the sum of the relevant row-column scores, which are in red text in the table. The resulting score is 36. The score for TC3 is 24, which is blue text; the score for TC6 is 24, which is green text, and the score for TC7 is 16, which is in black text. The cell scores are used to determine a capacitance change ratio between the capacitances in an effected for and in an effected column.

For example, the capacitance change detected by a row DCS is $\Delta C\_total = A*\Delta Ci + B*\Delta Cj + C*\Delta Ck + D*\Delta Cl$, with four capacitors in the row. The coefficients A, B, C, and D are determined based on the corresponding cell scores. As a specific example, row 4 includes capacitor C20 in cell TC5, capacitor C24 in cell TC6, capacitor C28 in cell TC7, and capacitor C32 in cell TC8. The cell scores for TC5 and TC8 are zero. Thus, for row 4, the capacitance change equation is $\Delta C\_total = 0*\Delta Ci + B*\Delta Cj + C*\Delta Ck + 0*\Delta Cl$, which equals $B*\Delta Cj + C*\Delta Ck$.

The coefficients B and C are determined from the cell scores of TC6 and TC7. For instance, B=1−[TC6 score/(TC6 score+TC7 score) and coefficient C=1−[TC7 score/(TC6 score+TC7 score). Using the data of the table in FIG. 26D, B=1−(24/(24+16), which equals 0.4 and C=1−(16/(24+16), which equals 0.6. Thus, 40% of the total capacitance change detected by the row 4 DSC is attributable to C24 and 60% of the total capacitance change is attributable to C28. Similar functions are used to determine the individual capacitance changes of the capacitors in cells TC2, TC3, TC6, and TC7. With the individual capacitances determined, the corresponding force is calculable, then the reference plane, then the normal vector, and then the magnitude and direction of the applied impact force.

Note that the various calculations as discussed with reference to FIGS. 17 through 26D are performed by the processing module of the force detection system 20 and/or by the computing entity. In an embodiment, the force detection system stores impedance values of the variable capacitors per sampling interval. The computing entity functions to convert the impedance into a capacitance value and the capacitance value into a pressure value (e.g., force over the area of a capacitor). The computing entity then determines the reference plane and the normal vector.

Figure 27A:
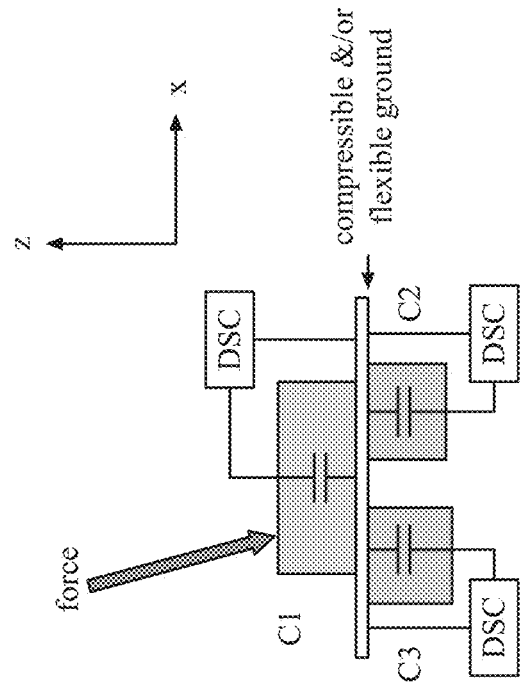
FIGS. 27A-27C are schematic block diagrams of an example of determining a normal vector of a cell of a force detection system in response to an impact force.
Figure 27B:
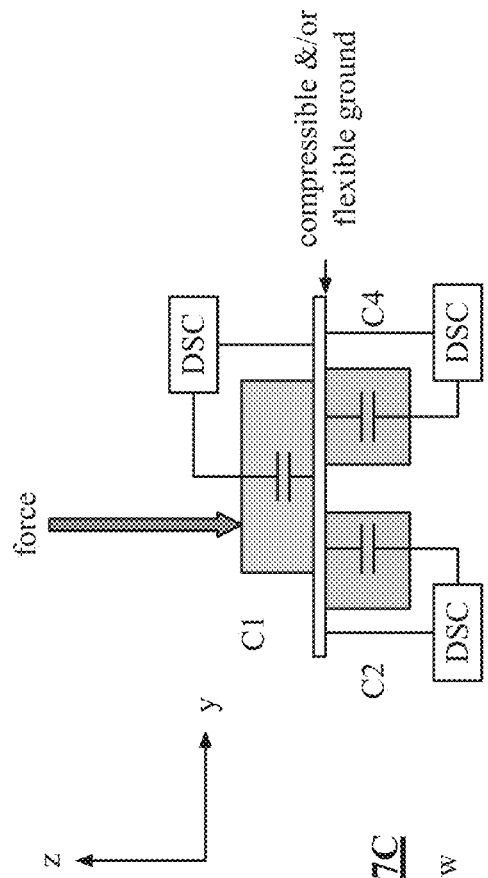
Figure 27C:
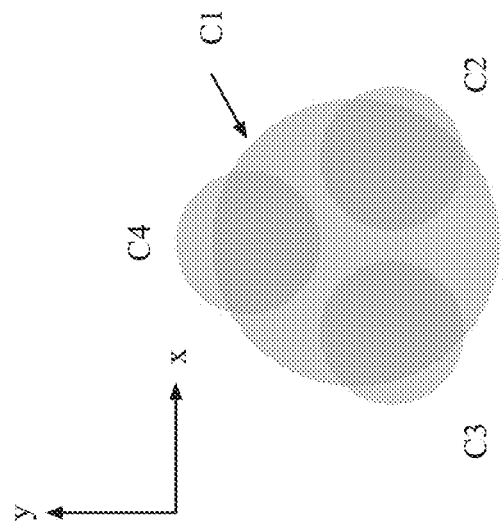

FIGS. 27A-27C are schematic block diagrams of an example of determining a normal vector of a cell of a force detection system in response to an impact force. In this example, the cell includes a top layer capacitor C1, a compressible and/or flexible ground plane, and three lower layer capacitors C2 and C3. FIG. 27A illustrates a top view of the cell where the top layer capacitor C1 substantially overlaps the three lower-level capacitors. FIGS. 27B and 27C illustrate side views of the cell. In this example, the cell is coupled to four drive sense circuits (DSC), one to each of the capacitors. The cell functions similarly to previously discussed cells.

Figure 28B:
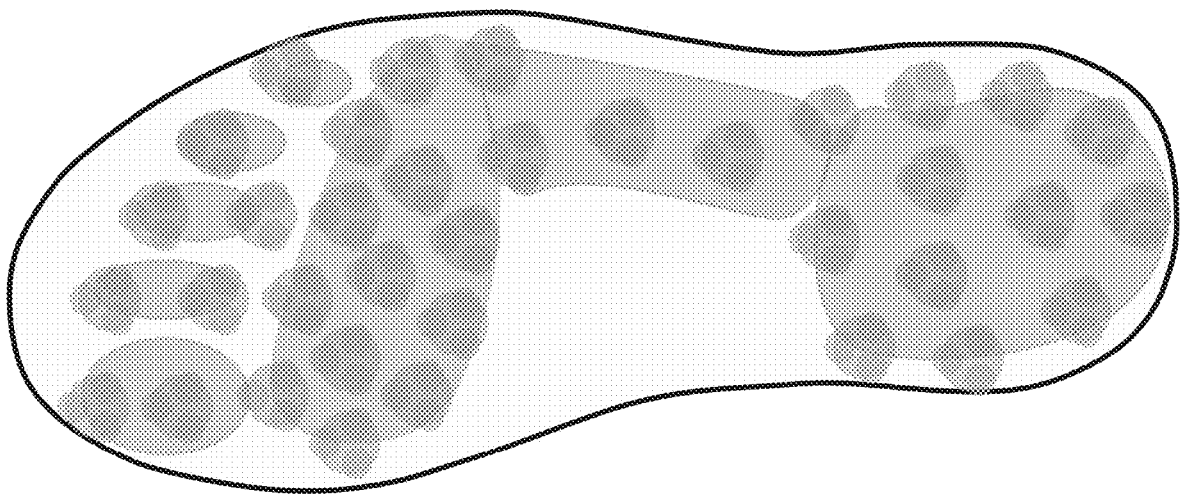
FIGS. 28A and 28B are schematic block diagrams of examples of placement of force cells within a sole of a shoe with respect to expected forces applied by a foot.
Figure 28A:
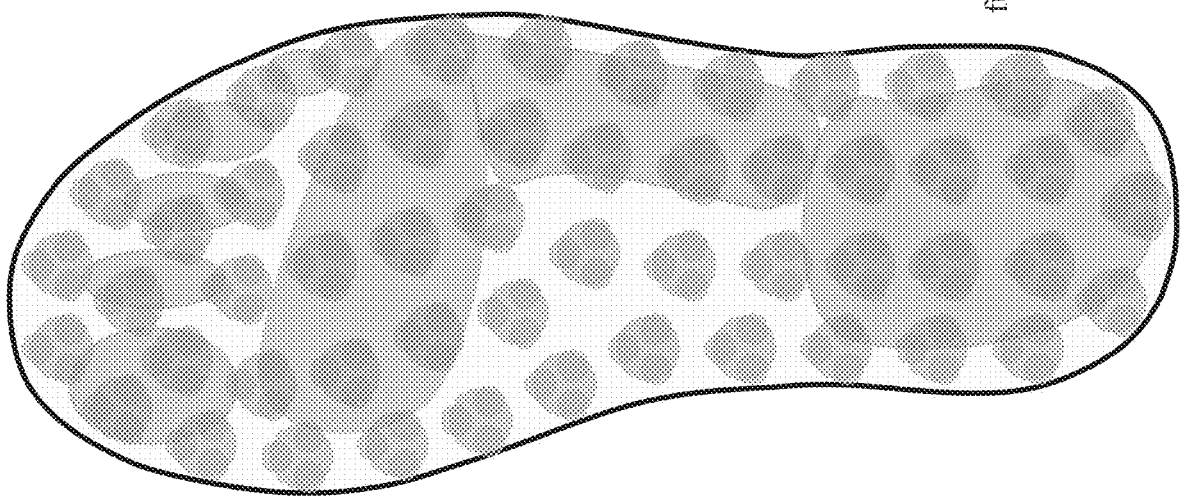

FIGS. 28A and 28B are schematic block diagrams of examples of placement of force cells within a sole of a shoe with respect to expected forces applied by a foot. FIG. 28A shows a full coverage cell placement pattern where the cells are substantially evenly distributed throughout the sole from a top view perspective. FIG. 28B shows the pressure sensor cells arranged in a toe zone, a ball of foot zone, a later midfoot zone, and a heal zone, wherein, within one of the zones, the pressure sensor cells are of approximately equal size. In another embodiment, the cells may be of different sizes. For example, a cell under the ball of foot is larger than a cell under a toe. In another embodiment, less cells are used in the selected coverage pattern.

Figure 29:
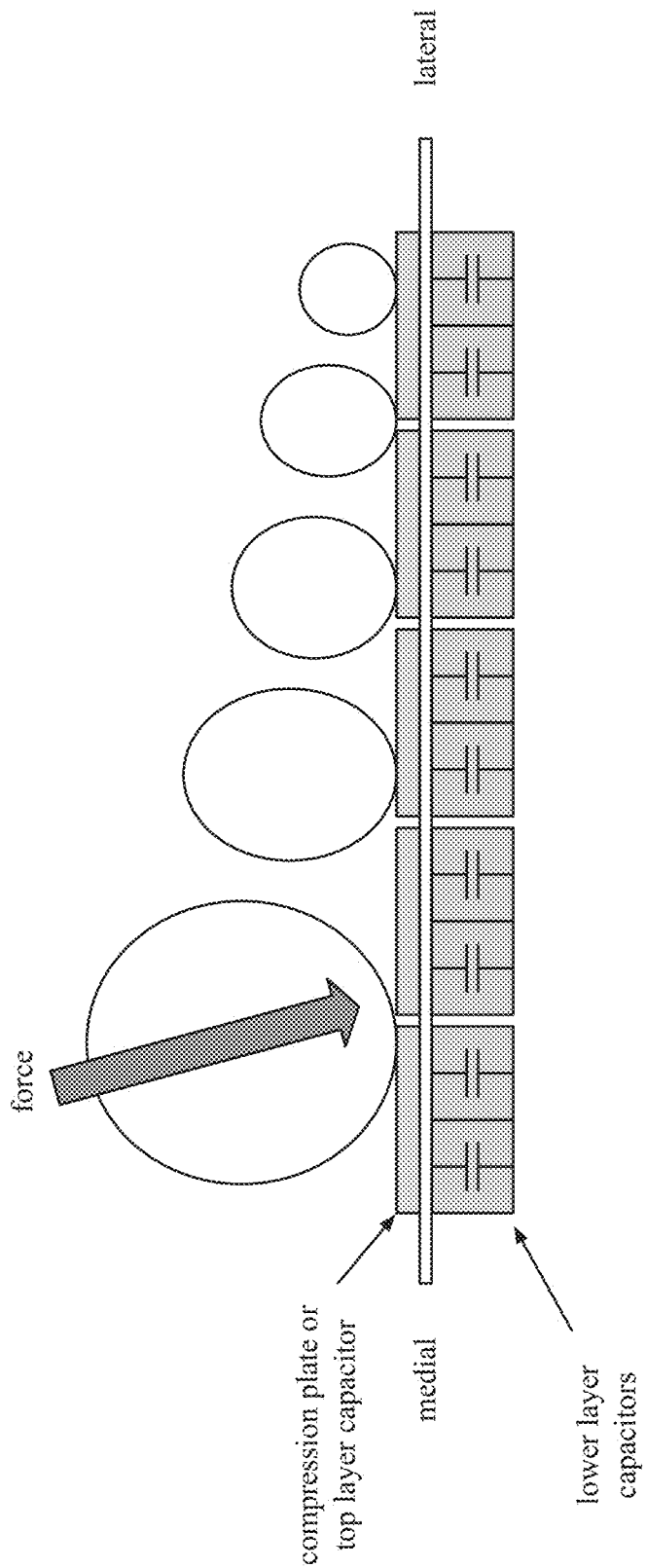
FIG. 29 is a schematic block diagram of an example of an angular impact force applied by a foot on the force detection system.

FIG. 29 is a schematic block diagram of an example of an angular impact force applied by a foot on the force detection system. In this example, a plurality of force cells is positioned from the medial side of a sole to the lateral side of the sole. As positioned, the cells are underneath the toes (from a front of the shoe perspective) and able to detect forces as previously described.

Figure 30:
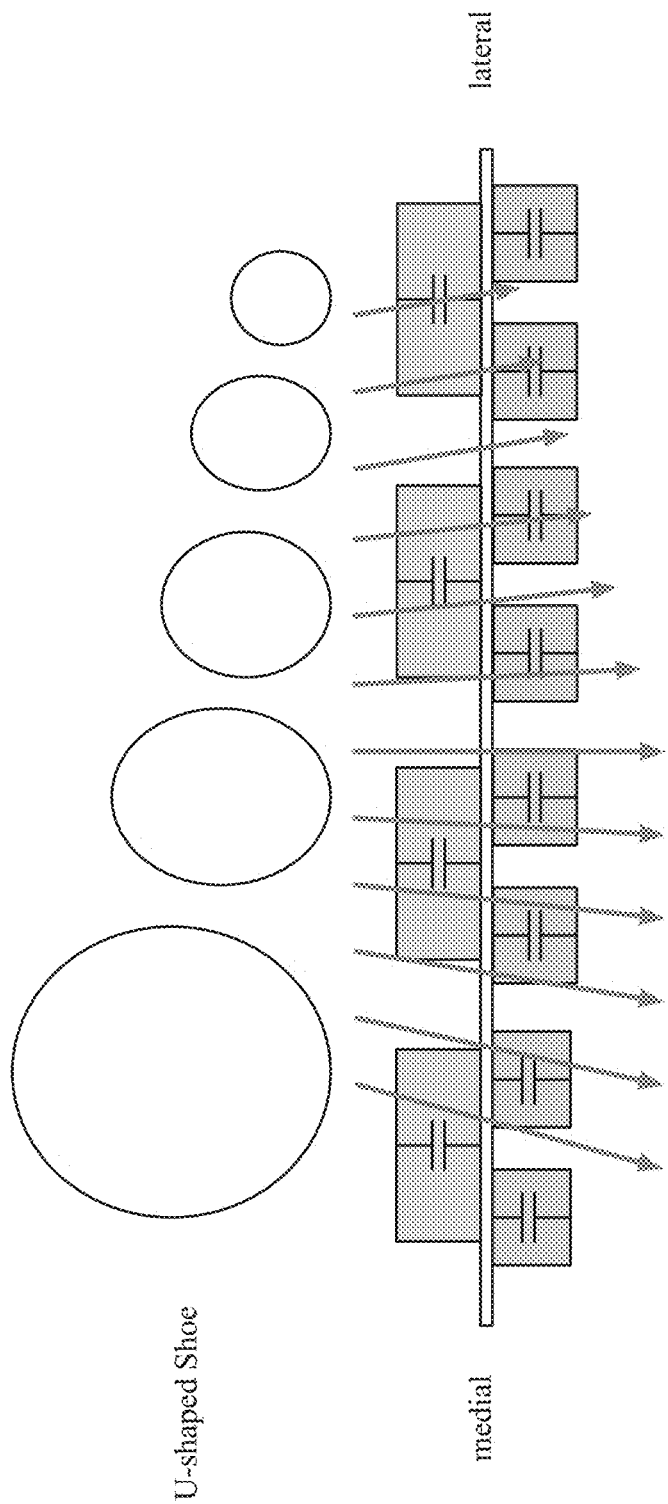
FIG. 30 is a schematic block diagram of another example of an angular impact force applied by a foot on the force detection system.

FIG. 30 is a schematic block diagram of another example of an angular impact force applied by a foot on the force detection system. In this example, the midsole has a U-shape, which causes the force to be radiated in a pattern has shown. This causes the ground reaction force to be angled away from the body, which adversely affects athletic performance. With the force detection system, such ground reaction force inefficiencies can be detected.

Figure 31:
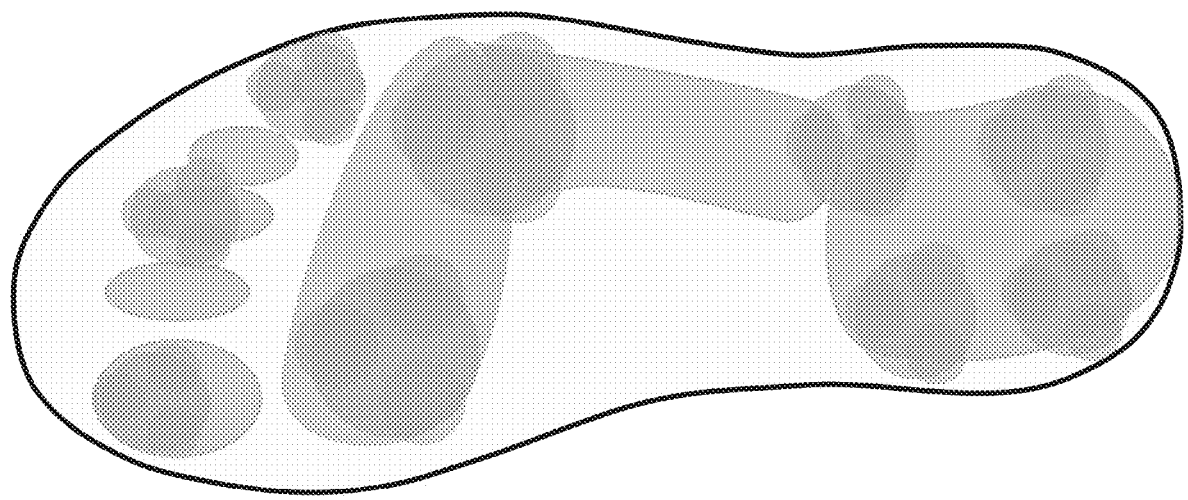
FIG. 31 is a schematic block diagram of another example of cell placement in a sole with respect to expected forces applied by a foot.

FIG. 31 is a schematic block diagram of another example of cell placement in a sole with respect to expected forces applied by a foot. In this example, nine cells are used and are of different sizes. Larger cells are positioned in the ball of foot area and smaller cells are positioned by the toes. The heal cells are smaller than the ball of foot cells but larger than the toe cells.

FIGS. 32A-32C are schematic block diagrams of another embodiment of force detection system 20. The force detection system 20 includes a layer of variable capacitors 200 and a circuitry section 104 in a sole of a shoe. The circuitry section 104 houses the circuitry of FIG. 3.

The layer of variable capacitors 200 includes variable capacitors that compress in the z-direction, variable capacitors that compress in the y-direction, and/or variable capacitors that compress in the x-direction. The different compression orientated variable capacitors may be on the same layer or in different layers. In an embodiment, the different compression orientated variable capacitors are in the same layer.

FIGS. 33A-33E are schematic block diagrams of an example of a cell of the force detection system of FIGS. 32A-32C. FIG. 33A is a top view of a force sensing cell that includes a z-direction compressible capacitor, y-direction compressible capacitors, x-direction compressible capacitors, and a cell housing. The cell may further include a compression plate.

The z-direction compressible capacitor changes its capacitance in accordance with a force in the z direction, but negligibly changes its capacitances as result of an x-direction force or a y-direction force. The y-direction compressible capacitor changes its capacitance in accordance with a force in the y direction, but negligibly changes its capacitances as result of an x-direction force or a z-direction force. The x-direction compressible capacitor changes its capacitance in accordance with a force in the x direction, but negligibly changes its capacitances as result of an z-direction force or a y-direction force.

Thus, when an applied impact force that includes x, y, and z components is applied to the cell, the z-direction compressible capacitor changes its capacitance based on the z component of the applied impact force; the y-direction compressible capacitor changes its capacitance based on the y component of the applied impact force; and the x-direction compressible capacitor changes its capacitance based on the x component of the applied impact force. As such, the capacitance change of the z-direction compressible capacitor represents the z component of the impact force; the capacitance change of the y-direction compressible capacitor represents the y component of the impact force; and the capacitance change of the x-direction compressible capacitor represents the x component of the impact force.

From the x, y, and z force components determined based on capacitance, the magnitude and direction of the impact force on the cell can be determined. In essence, it's a conversion from Cartesian coordinates to polar coordinates.

FIG. 33B is a side view of an embodiment of the cell of FIG. 33A. The cell includes the housing and the directional capacitors. In this side view, which is from the x-z plane, the z-direction compressible capacitor is between the two x-direction compressible capacitors. When an impact force is applied to the cell that includes an x and a z component, the z direction compressible capacitor changes its capacitance based on the z direction force component. With a positive x force component, the x-direction compressible capacitor in the positive x direction changes its capacitance based on the x direction force component. The x-direction compressible capacitor in the negative x direction does not change its capacitance assuming that when no force is applied, the capacitor is at its minimum (no compression) value.

In an embodiment, the x-direction compressible capacitors each have mid-point compression (e.g., 40% to 60% of full compression) when no impact force is applied to the cell. In this manner, when an x force is applied to the cell, one of the x-direction compressible capacitors compresses further and increases its capacitance while the other is compressed less and decreases its capacitance. The two changes are then used to determine the x force magnitude and direction.

The y-direction compressible capacitors function in a similar manner as the x-direction compressible capacitors, only in the y direction instead of x direction.

FIG. 33C is a side view of an embodiment of the cell of FIG. 33A. The cell includes the housing, the directional capacitors, and compression plate. In this side view, which is from the y-z plane, the z-direction compressible capacitor is below the compression plate, which is between the two y-direction compressible capacitors. When an impact force is applied to the cell that includes a y and a z component, the z direction compressible capacitor changes its capacitance based on the z direction force component. With a positive y force component, the y-direction compressible capacitor in the positive y direction changes its capacitance based on the y direction force component. The y-direction compressible capacitor in the negative y direction does not change its capacitance assuming that when no force is applied, the capacitor is at its minimum (no compression) value.

In an embodiment, the y-direction compressible capacitors each have mid-point compression (e.g., 40% to 60% of full compression) when no impact force is applied to the cell. In this manner, when a y force is applied to the cell, one of the y-direction compressible capacitors compresses further and increases its capacitance while the other is compressed less and decreases its capacitance. The two changes are then used to determine the y force magnitude and direction.

FIG. 33D is a top view of a force sensing cell that includes a z-direction compressible capacitor, x-direction compressible capacitors, and a cell housing. The cell may further include a compression plate. The compressible capacitors function as previously described. Such a force sensing cell is used in the force detection system where there is a z force component and an x force component and a negligible y force component. For example, the cell is used for medial to lateral force detection in a shoe where there will be negligible toe to heal force.

FIG. 33E is a top view of a force sensing cell that includes a z-direction compressible capacitor, y-direction compressible capacitors, and a cell housing. The cell may further include a compression plate. The compressible capacitors function as previously described. Such a force sensing cell is used in the force detection system where there is a z force component and a y force component and a negligible x force component. For example, the cell is used for in the toe area.

It is noted that terminologies as may be used herein such as bit stream, stream, signal sequence, etc. (or their equivalents) have been used interchangeably to describe digital information whose content corresponds to any of a number of desired types (e.g., data, video, speech, text, graphics, audio, etc. any of which may generally be referred to as 'data').

As may be used herein, the terms "substantially" and "approximately" provide an industry-accepted tolerance for its corresponding term and/or relativity between items. For some industries, an industry-accepted tolerance is less than one percent and, for other industries, the industry-accepted tolerance is 10 percent or more. Other examples of industry-accepted tolerance range from less than one percent to fifty percent. Industry-accepted tolerances correspond to, but are not limited to, component values, integrated circuit process variations, temperature variations, rise and fall times, thermal noise, dimensions, signaling errors, dropped packets, temperatures, pressures, material compositions, and/or performance metrics. Within an industry, tolerance variances of accepted tolerances may be more or less than a percentage level (e.g., dimension tolerance of less than +/−1%). Some relativity between items may range from a difference of less than a percentage level to a few percent. Other relativity between items may range from a difference of a few percent to magnitude of differences.

As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to".

As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may be used herein, one or more claims may include, in a specific form of this generic form, the phrase "at least one of a, b, and c" or of this generic form "at least one of a, b, or c", with more or less elements than "a", "b", and "c". In either phrasing, the phrases are to be interpreted identically. In particular, "at least one of a, b, and c" is equivalent to "at least one of a, b, or c" and shall mean a, b, and/or c. As an example, it means: "a" only, "b" only, "c" only, "a" and "b", "a" and "c", "b" and "c", and/or "a", "b", and "c".

As may also be used herein, the terms "processing module", "processing circuit", "processor", "processing circuitry", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, processing circuitry, and/or processing unit may be, or further include, memory and/or an integrated memory element, which may be a single memory device, a plurality of memory devices, and/or embedded circuitry of another processing module, module, processing circuit, processing circuitry, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, processing circuitry, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, processing circuitry and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, processing circuitry and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with one or more other routines. In addition, a flow diagram may include an "end" and/or "continue" indication. The "end" and/or "continue" indications reflect that the steps presented can end as described and shown or optionally be incorporated in or otherwise used in conjunction with one or more other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

While transistors may be shown in one or more of the above-described figure(s) as field effect transistors (FETs), as one of ordinary skill in the art will appreciate, the transistors may be implemented using any type of transistor structure including, but not limited to, bipolar, metal oxide semiconductor field effect transistors (MOSFET), N-well transistors, P-well transistors, enhancement mode, depletion mode, and zero voltage threshold (VT) transistors.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid-state memory, a hard drive memory, cloud memory, thumb drive, server memory, computing device memory, and/or other physical medium for storing digital information.

As applicable, one or more functions associated with the methods and/or processes described herein can be implemented via a processing module that operates via the non-human "artificial" intelligence (AI) of a machine. Examples of such AI include machines that operate via anomaly detection techniques, decision trees, association rules, expert systems and other knowledge-based systems, computer vision models, artificial neural networks, convolutional neural networks, support vector machines (SVMs), Bayesian networks, genetic algorithms, feature learning, sparse dictionary learning, preference learning, deep learning and other machine learning techniques that are trained using training data via unsupervised, semi-supervised, supervised and/or reinforcement learning, and/or other AI. The human mind is not equipped to perform such AI techniques, not only due to the complexity of these techniques, but also due to the fact that artificial intelligence, by its very definition—requires "artificial" intelligence—i.e., machine/non-human intelligence.

As applicable, one or more functions associated with the methods and/or processes described herein can be implemented as a large-scale system that is operable to receive, transmit and/or process data on a large-scale. As used herein, a large-scale refers to a large number of data, such as one or more kilobytes, megabytes, gigabytes, terabytes or more of data that are received, transmitted and/or processed. Such receiving, transmitting and/or processing of data cannot practically be performed by the human mind on a large-scale within a reasonable period of time, such as within a second, a millisecond, microsecond, a real-time basis or other high speed required by the machines that generate the data, receive the data, convey the data, store the data and/or use the data.

As applicable, one or more functions associated with the methods and/or processes described herein can require data to be manipulated in different ways within overlapping time spans. The human mind is not equipped to perform such different data manipulations independently, contemporaneously, in parallel, and/or on a coordinated basis within a reasonable period of time, such as within a second, a millisecond, microsecond, a real-time basis or other high speed required by the machines that generate the data, receive the data, convey the data, store the data and/or use the data.

As applicable, one or more functions associated with the methods and/or processes described herein can be implemented in a system that is operable to electronically receive digital data via a wired or wireless communication network and/or to electronically transmit digital data via a wired or wireless communication network. Such receiving and transmitting cannot practically be performed by the human mind because the human mind is not equipped to electronically transmit or receive digital data, let alone to transmit and receive digital data via a wired or wireless communication network.

As applicable, one or more functions associated with the methods and/or processes described herein can be implemented in a system that is operable to electronically store digital data in a memory device. Such storage cannot practically be performed by the human mind because the human mind is not equipped to electronically store digital data.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A low power force detection system comprises:
   a plurality of variable capacitors, wherein a variable capacitor of the plurality of variable capacitors includes:
      two plates;
      one or more conductive layers; and
      one or more insulating layers when the variable capacitor includes more than one conductive layer;
   a drive sense module operably coupled to the plurality of variable capacitors, wherein a drive sense circuit of the drive sense module is coupled to one or more variable capacitors of the plurality of capacitors, and wherein the drive sense circuit is operable to:
      provide an analog and frequency domain signal to the one or more variable capacitors;
      detect a characteristic of the one or more variable capacitors based on the analog and frequency domain signal; and
      generate a representative signal of the characteristic; and
   a processing module operable to the drive sense module, wherein the processing module is operable to:
      generate a digital value based on the representative; and
      write the digital value to memory.

2. The low power force detection system of claim 1, wherein the analog and frequency domain signal comprises:
   a DC signal component; and
   an oscillating signal component that has a frequency and a magnitude.

3. The low power force detection system of claim 1, wherein the characteristic comprises:
   an impedance based on a current and a voltage, wherein one of the current and the voltage is regulated and the other is a reference.

4. The low power force detection system of claim 1 further comprises:
   the drive sense circuit being including:
      an operational amplifier operable to generate an analog signal representing impedance of the one or more variable capacitors; and
      an analog to digital converter operable to generate the representative signal as an unfiltered digital representation of the representing impedance of the one or more variable capacitors;
   the processing module being further operable to:
      digitally filter the representative signal to produce a high-resolution digital value of the impedance of the one or more variable capacitors.

5. The low power force detection system of claim 1 further comprises:
   a clock circuit operable to generate a sampling clock and a digital clock, wherein a sampling rate for sampling impedance of the one or more variable capacitors is derived from the sampling clock and wherein the writing the digital value to the memory is done a write rate that is derived from the digital clock.

6. The low power force detection system of claim 5, wherein the clock circuit is further operable to:
generate a real-time clock, wherein the processing module time stamps the digital value in accordance with the real-time clock as part of writing the digital value to the memory.

7. The low power force detection system of claim 1 further comprises:
a communication circuit operably coupled to the processing module and to the memory, wherein the communication circuit communicates with a computing entity to download stored digital values to the computing entity.

8. The low power force detection system of claim 1 further comprises:
a power source circuit operable to provide power to the low power force detection system, wherein the power source circuit includes one or more of:
a battery;
a battery charger;
a linear regulator;
a power supply; and
a power harvesting circuit.

9. The low power force detection system of claim 1, wherein the processing module is further operable to generate the digital value by:
converting the representative signal of the characteristic into an impedance value as the digital value.

10. The low power force detection system of claim 1, wherein the processing module is further operable to generate the digital value by:
converting the representative signal of the characteristic into an impedance value; and
converting the impedance value into a capacitance value as the digital value.

11. The low power force detection system of claim 1, wherein the processing module is further operable to generate the digital value by:
converting the representative signal of the characteristic into an impedance value;
converting the impedance value into a capacitance value; and
converting the capacitance value into a pressure value as the digital value.

12. A low power force detection system comprises:
a plurality of pressure sensor cells arranged in a pattern within a sole of a shoe, wherein a pressure sensor cell of the plurality of pressure sensor cells includes a set of variable capacitors, wherein a variable capacitor of the set of variable capacitors includes:
two plates;
one or more conductive layers; and
one or more insulating layers when the variable capacitor includes more than one conductive layer;
a plurality of drive sense modules operably coupled to the plurality of pressure sensor cells, wherein a drive sense module of the plurality of drive sense modules includes a set of drive sense circuits, wherein a drive sense circuit of the set of drive sense circuits is coupled to a variable capacitor of the set of variable capacitors, and wherein the drive sense circuit is operable to:
provide an analog and frequency domain signal to the variable capacitor;
detect a characteristic of the variable capacitor based on the analog and frequency domain signal; and
generate a representative signal of the characteristic; and a processing module operable to the drive sense module, wherein the processing module is operable to:
generate a digital value based on the representative; and
write the digital value to memory.

13. The low power force detection system of claim 12, wherein the pattern comprises:
the plurality of pressure sensor cells distributed substantially evenly throughout the sole from a top view perspective, wherein the plurality of pressure sensor cells is of approximately equal size.

14. The low power force detection system of claim 12, wherein the pattern comprises:
the plurality of pressure sensor cells arranged in a toe zone, a ball of foot zone, a later midfoot zone, and a heal zone, wherein, within one of the zones, the pressure sensor cells are of approximately equal size.

15. The low power force detection system of claim 12, wherein the pattern comprises:
a first set of a first size pressure sensor cells in a toe area of the shoe;
a second set of a second size pressure sensor cells in a ball of foot area of the shoe; and
a third set of a third size pressure sensor cells in a heal area of the shoe, wherein the second size is greater than the third size, which is greater than the first size.

16. The low power force detection system of claim 12 further comprises:
the drive sense circuit being including:
an operational amplifier operable to generate an analog signal representing impedance of the variable capacitor; and
an analog to digital converter operable to generate the representative signal as an unfiltered digital representation of the representing impedance of the variable capacitor;
the processing module being further operable to:
digitally filter the representative signal to produce a high-resolution digital value of the impedance of the variable capacitor.

17. The low power force detection system of claim 12 further comprises:
a clock circuit operable to generate a sampling clock and a digital clock, wherein a sampling rate for sampling impedance of the variable capacitor is derived from the sampling clock and wherein the writing the digital value to the memory is done a write rate that is derived from the digital clock.

18. The low power force detection system of claim 17, wherein the clock circuit is further operable to:
generate a real-time clock, wherein the processing module time stamps the digital value in accordance with the real-time clock as part of writing the digital value to the memory.

19. The low power force detection system of claim 12 further comprises:
a communication circuit operably coupled to the processing module and to the memory, wherein the communication circuit communicates with a computing entity to download stored digital values to the computing entity.

20. The low power force detection system of claim 12 further comprises:
a power source circuit operable to provide power to the low power force detection system, wherein the power source circuit includes one or more of:
a battery;
a battery charger;

a linear regulator;
a power supply; and
a power harvesting circuit.

21. The low power force detection system of claim 12, wherein the processing module is further operable to generate the digital value by:
   converting the representative signal of the characteristic into an impedance value as the digital value.

22. The low power force detection system of claim 12, wherein the processing module is further operable to generate the digital value by:
   converting the representative signal of the characteristic into an impedance value; and
   converting the impedance value into a capacitance value as the digital value.

23. The low power force detection system of claim 12, wherein the processing module is further operable to generate the digital value by:
   converting the representative signal of the characteristic into an impedance value;
   converting the impedance value into a capacitance value; and
   converting the capacitance value into a pressure value as the digital value.

* * * * *